United States Patent
Hu et al.

(10) Patent No.: US 10,112,939 B2
(45) Date of Patent: Oct. 30, 2018

(54) TIED-BACK BENZAMIDE DERIVATIVES AS POTENT ROCK INHIBITORS

(71) Applicant: Bristol-Myers Squibb Company, Princeton, NJ (US)

(72) Inventors: Zilun Hu, Jamison, PA (US); Doree F. Sitkoff, Dresher, PA (US); Mimi L. Quan, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/503,419

(22) PCT Filed: Aug. 20, 2015

(86) PCT No.: PCT/US2015/046032
§ 371 (c)(1),
(2) Date: Feb. 13, 2017

(87) PCT Pub. No.: WO2016/028971
PCT Pub. Date: Feb. 25, 2016

(65) Prior Publication Data
US 2017/0226105 A1    Aug. 10, 2017

Related U.S. Application Data

(60) Provisional application No. 62/040,044, filed on Aug. 21, 2014.

(51) Int. Cl.
| | |
|---|---|
| C07D 401/10 | (2006.01) |
| C07D 401/14 | (2006.01) |
| C07D 403/10 | (2006.01) |
| C07D 403/14 | (2006.01) |
| C07D 405/14 | (2006.01) |
| C07D 409/14 | (2006.01) |
| C07D 471/04 | (2006.01) |
| C07D 231/12 | (2006.01) |
| C07D 413/14 | (2006.01) |

(52) U.S. Cl.
CPC ......... *C07D 471/04* (2013.01); *C07D 231/12* (2013.01); *C07D 401/10* (2013.01); *C07D 401/14* (2013.01); *C07D 403/10* (2013.01); *C07D 403/14* (2013.01); *C07D 405/14* (2013.01); *C07D 409/14* (2013.01); *C07D 413/14* (2013.01)

(58) Field of Classification Search
CPC .. C07D 401/10; C07D 401/14; C07D 403/10; C07D 403/14; C07D 405/14; C07D 409/14
See application file for complete search history.

(56) References Cited

U.S. PATENT DOCUMENTS

| 7,601,716 B2 | 10/2009 | Dorsey et al. |
| 2008/0161297 A1 | 7/2008 | Bosanac et al. |
| 2009/0312327 A1 | 12/2009 | Bissantz et al. |
| 2010/0041645 A1 | 2/2010 | Dahmann et al. |
| 2012/0122842 A1 | 5/2012 | Curtin et al. |

FOREIGN PATENT DOCUMENTS

| CN | 103664878 A | 3/2014 |
| EP | 0 533 267 A1 | 3/1993 |
| EP | 1 553 089 A1 | 7/2005 |
| EP | 2 687 528 A1 | 1/2014 |
| EP | 2 743 256 A1 | 6/2014 |
| JP | 02059559 A | 2/1990 |
| WO | WO1995/06637 A1 | 3/1995 |
| WO | WO1995/11243 A1 | 4/1995 |
| WO | WO2000/06085 A2 | 2/2000 |
| WO | WO2000/09480 A1 | 2/2000 |
| WO | WO2000/66558 A1 | 11/2000 |
| WO | WO2001/70673 A2 | 9/2001 |
| WO | WO2001/77087 A1 | 10/2001 |
| WO | WO2001/81310 A1 | 11/2001 |
| WO | WO2002/064545 A1 | 8/2002 |
| WO | WO2003/029245 A1 | 4/2003 |
| WO | WO2003/068749 A1 | 8/2003 |
| WO | WO2003/087057 A1 | 10/2003 |

(Continued)

OTHER PUBLICATIONS

Chemical Abstracts Registry No. 207799-24-4, indexed in the Registry file on STN CAS Online on Jul. 1, 1998.*
CAS Registry No. 1062122-67-1 (Oct. 16, 2008).
CAS Registry No. 1453004-24-4 (Sep. 22, 2013).
CAS Registry No. 1436085-88-9 (Jun. 9, 2013).
CAS Registry No. 1434957-39-7 (Jun. 5, 2013).
CAS Registry No. 1434526-52-9 (Jun. 5, 2013).
CAS Registry No. 1422913-79-8 (Mar. 11, 2013).
CAS Registry No. 1394590-53-4 (Sep. 18, 2012).
CAS Registry No. 1394544-02-5 (Sep. 18, 2012).

(Continued)

*Primary Examiner* — Laura L Stockton
(74) *Attorney, Agent, or Firm* — Hong Liu

(57) ABSTRACT

The present invention provides compounds of Formula (I) or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

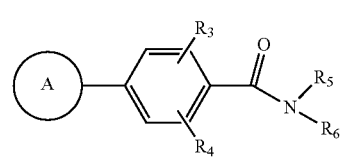

(I)

7 Claims, No Drawings

(56) References Cited

FOREIGN PATENT DOCUMENTS

| | | |
|---|---|---|
| WO | WO2004/054974 A1 | 7/2004 |
| WO | WO2004/056774 A2 | 7/2004 |
| WO | WO2004/072025 A2 | 8/2004 |
| WO | WO2004/076412 A2 | 9/2004 |
| WO | WO2004/078756 A2 | 9/2004 |
| WO | WO2005/074643 A2 | 8/2005 |
| WO | WO2005/097740 A1 | 10/2005 |
| WO | WO2006/123725 A1 | 11/2006 |
| WO | WO2006/127587 A1 | 11/2006 |
| WO | WO2007/002559 A1 | 1/2007 |
| WO | WO2007/009741 A1 | 1/2007 |
| WO | WO2007/084667 A2 | 7/2007 |
| WO | WO2007/120096 A1 | 10/2007 |
| WO | WO2007/130468 A2 | 11/2007 |
| WO | WO2008/029825 A1 | 3/2008 |
| WO | WO2008/133955 A1 | 11/2008 |
| WO | WO2009/019163 A1 | 2/2009 |
| WO | WO2009/027392 A1 | 3/2009 |
| WO | WO2009/072643 A1 | 6/2009 |
| WO | WO2009/073545 A2 | 6/2009 |
| WO | WO2010/005783 A1 | 1/2010 |
| WO | WO2010/023161 A1 | 3/2010 |
| WO | WO2010/040663 A1 | 4/2010 |
| WO | WO2010/077624 A1 | 7/2010 |
| WO | WO2010/086259 A1 | 8/2010 |
| WO | WO2010/106081 A1 | 9/2010 |
| WO | WO2010/122069 A1 | 10/2010 |
| WO | WO2010/137738 A1 | 12/2010 |
| WO | WO2010/142752 A1 | 12/2010 |
| WO | WO2011/047319 A2 | 4/2011 |
| WO | WO2011/073376 A1 | 6/2011 |
| WO | WO2011/092198 A1 | 8/2011 |
| WO | WO2012/004207 A1 | 1/2012 |
| WO | WO2012/006202 A1 | 1/2012 |
| WO | WO2013/153539 A1 | 10/2013 |
| WO | WO2013/155338 A2 | 10/2013 |
| WO | WO2014/001464 A1 | 1/2014 |
| WO | WO-2014/008197 A1 * | 1/2014 |
| WO | WO2014/012614 A1 | 1/2014 |
| WO | WO2014/055996 A2 | 4/2014 |
| WO | WO2014/113620 A2 | 7/2014 |
| WO | WO2014/134388 A1 | 9/2014 |
| WO | WO2014/134391 A1 | 9/2014 |

OTHER PUBLICATIONS

CAS Registry No. 1394482-78-0 (Sep. 18, 2012).
CAS Registry No. 1394460-12-8 (Sep. 18, 2012).
CAS Registry No. 1355772-96-1 (Feb. 8, 2012).
CAS Registry No. 1317357-70-2 (Aug. 14, 2011).
CAS Registry No. 1316743-65-3 (Aug. 12, 2011).
CAS Registry No. 1302160-93-5 (May 29, 2011).
CAS Registry No. 1300287-42-6 (May 25, 2011).
CAS Registry No. 1296169-39-5 (May 17, 2011).
CAS Registry No. 1289324-16-8 (May 3, 2011).
CAS Registry No. 1289279-08-8 (May 3, 2011).
CAS Registry No. 1278876-16-6 (Apr. 12, 2011).
CAS Registry No. 1119212-84-8 (Mar. 11, 2009).
CAS Registry No. 1090819-33-2 (Dec. 28, 2008).
CAS Registry No. 1016334-55-6 (Apr. 22, 2008).
CAS Registry No. 1015953-30-6 (Apr. 21, 2008).
CAS Registry No. 1015659-02-5 (Apr. 18, 2008).
CAS Registry No. 1015629-30-7 (Apr. 18, 2008).
CAS Registry No. 1011159-56-0 (Mar. 31, 2008).
CAS Registry No. 1011118-73-2 (Mar. 31, 2008).
Huber, John. D. et al., "Indentification of a Potent Sodium Hydrogen Exchanger Isoform 1 (NHE1) Inhibitor with a Suitable Profile for Chronic Dosing and Demonstrated Cardioprotective effects in a Preclinical Model of Myocardial Infarction in the Rat", J. of Medicinal Chemistry, vol. 55, pp. 7114-7140 (2012.
Miduturu, Chandrasekhar V. et al., "High-Throughput Kinase Profiling: A More Efficient Approach towards the Discovery of New Kinase Inhibitors", Chem Biology, vol. 18(7), pp. 868-879 (2011).
Yu, Ming et al., "Identification of piperazine-bisamide GHSR antagonists for the treatment of obesity", Bioorganic & Medicinal Chemistry Letters, vol. 20, pp. 1758-1762 (2010).
CAS Registry report (4AA-5AJ) on this 1449 , 2014.

* cited by examiner

TIED-BACK BENZAMIDE DERIVATIVES AS POTENT ROCK INHIBITORS

CROSS REFERENCE TO RELATED APPLICATIONS

This application is a 371 application of PCT/US2015/046032 filed Aug. 20, 2015, which is entitled to priority pursuant to 35 U.S.C. § 119(e) to U.S. provisional patent application No. 62/040,044, filed on Aug. 21, 2014, each of which is fully incorporated herein in its entirety.

FIELD OF THE INVENTION

The present invention relates generally to novel benzamides and their analogues thereof, which are inhibitors of Rho kinases, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as actin organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example, angiotensin II (Yamakawa, T. et al., *Hypertension*, 35:313-318 (2000)), urotensin II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovasc. Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovasc. Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol Ther.*, 18:67-74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., *Int. J. Mol.*

Sci., 13:8293-8307 (2012); Zhou, L. et al., Am. J. Nephrol., 34:468-475 (2011)), as well as neurological disorders, such as spinal-cord injury, Alzheimer's disease, multiple sclerosis, stroke and neuropathic pain (Mueller, B. K. et al., Nat. Rev. Drug Disc., 4:387-398 (2005); Sun, X. et al., J. Neuroimmunol., 180:126-134 (2006)).

There remains an unmet medical need for new drugs to treat cardiovascular disease. In the 2012 update of Heart Disease and Stroke Statistics from the American Heart Association (Circulation, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, US 2012/0122842, US 2010/0041645, US 2008/0161297, WO 2014/055996, WO 2014/113620, WO 2014/134388, WO 2014/134391 and Hu, E. et al., Exp. Opin. Ther. Targets, 9:715-736 (2005)), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel benzamides, their analogues, including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

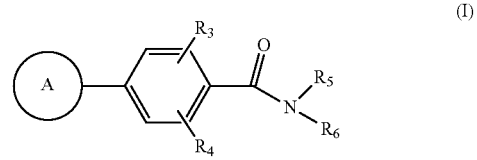

or stereoisomers, tautomers, pharmaceutically acceptable salts, solvates, or prodrugs thereof, wherein:

Ring A is independently selected from

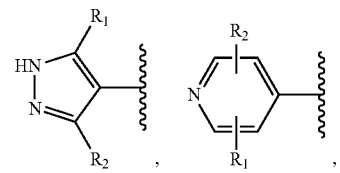

and

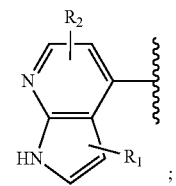

;

R₁ is independently selected from H, F, Cl, Br, OH, CN, NR$_a$R$_a$, —OC$_{1-4}$ alkyl substituted with 0-3 R$_e$, and C$_{1-4}$ alkyl substituted with 0-3 R$_e$;

R₂ is independently selected from H, —(CH₂)$_r$OR$_b$, (CH₂)$_r$S(O)$_p$R$_c$, —(CH₂)$_r$C(=O)R$_b$, —(CH₂)$_r$NR$_a$R$_a$, —(CH₂)$_r$C(=O)NR$_a$R$_a$, —(CH₂)$_r$C(=O)(CH₂)$_r$NR$_a$R$_a$, —(CH₂)$_r$CN, —(CH₂)$_r$NR$_a$C(=O)R$_b$, —(CH₂)$_r$NR$_a$C(=O)OR$_b$, —(CH₂)$_r$OC(=O)NR$_a$R$_a$, —(CH₂)$_r$NR$_a$C(=O)NR$_a$R$_a$, —(CH₂)$_r$C(=O)OR$_b$, —(CH₂)$_r$S(O)$_p$NR$_a$R$_a$, —(CH₂)$_r$NR$_a$S(O)$_p$NR$_a$R$_a$, —(CH₂)$_r$NR$_a$S(O)$_p$R$_c$, (CH₂)$_r$—C$_{3-6}$ carbocyclyl substituted with 0-3 R$_e$, and —(CH₂)$_r$-heterocyclyl substituted with 0-3 R$_e$;

R₃ is independently selected from H, F, Cl, Br, CN, C$_{1-4}$ alkyl substituted with 0-3 R$_e$, —(CH₂)$_r$OR$_b$, (CH₂)$_r$S(O)$_p$R$_c$, —(CH₂)$_r$C(=O)R$_b$, —(CH₂)$_r$NR$_a$R$_a$, —(CH₂)$_r$C(=O)NR$_a$R$_a$, —(CH₂)$_r$C(=O)(CH₂)$_r$NR$_a$R$_a$, —(CH₂)$_r$CN, —(CH₂)$_r$NR$_a$C(=O)R$_b$, —(CH₂)$_r$NR$_a$C(=O)OR$_b$, —(CH₂)$_r$OC(=O)NR$_a$R$_a$, —(CH₂)$_r$NR$_a$C(=O)NR$_a$R$_a$, —(CH₂)$_r$C(=O)OR$_b$, —(CH₂)$_r$S(O)$_p$NR$_a$R$_a$, —(CH₂)$_r$NR$_a$S(O)$_p$NR$_a$R$_a$, —(CH₂)$_r$NR$_a$S(O)$_p$R$_c$, (CH₂)$_r$—C$_{3-6}$ carbocyclyl substituted with 0-3 R$_e$, and —(CH₂)$_r$-heterocyclyl substituted with 0-3 R$_e$;

R₄ is independently selected from H, F, Cl, Br, OH, CN, OC$_{1-4}$ alkyl substituted with 0-3 R$_e$, and C$_{1-4}$ alkyl substituted with 0-3 R$_e$;

R₅ is independently selected from H and C$_{1-4}$ alkyl substituted with 0-3 R$_e$;

R₆ is independently selected from bicyclic carbocyclyl substituted with 0-3 R$_8$, and heterocyclyl comprising carbon atoms and 1-3 hetero atoms selected from N, NR$_7$, O, and S(O)$_p$ and substituted with 1-3 R$_8$;

alternatively, R₅ and R₆ together with the nitrogen atom to which they are both attached form a heterocyclyl comprising carbon atoms and 1-3 hetero atoms selected from N, NR$_7$, O, and S(O)$_p$ and substituted with 1-5 R$_8$;

R₇ is independently selected from H, C$_{1-4}$alkyl substituted with 0-4 R$_e$, —C(=O)R$_b$, —C(=O)NR$_a$R$_a$, —C(=O)(CH₂)$_r$NR$_a$R$_a$, —C(=O)OR$_b$, —(CH₂)$_r$—C$_{3-6}$ carbocyclyl substituted with 0-3 R$_e$, and —(CH₂)$_r$-heterocyclyl substituted with 0-3 R$_e$;

R₈ is independently selected from F, Cl, Br, CN, C$_{1-4}$ alkyl substituted with 0-3 R$_e$, —(CH₂)$_r$OR$_b$, (CH₂)$_r$S(O)$_p$R$_c$, —(CH₂)$_r$C(=O)R$_b$, —(CH₂)$_r$NR$_a$R$_a$, —(CH₂)$_r$C(=O)NR$_a$R$_a$, —(CH₂)$_r$C(=O)(CH₂)$_r$NR$_a$R$_a$, —(CH₂)$_r$CN, —(CH₂)$_r$NR$_a$C(=O)R$_b$, —(CH₂)$_r$NR$_a$C(=O)OR$_b$, —(CH₂)$_r$OC(=O)NR$_a$R$_a$, —(CH₂)$_r$NR$_a$C(=O)NR$_a$R$_a$, —(CH₂)$_r$C(=O)OR$_b$, —(CH₂)$_r$S(O)$_p$NR$_a$R$_a$, —(CH₂)$_r$NR$_a$S(O)$_p$NR$_a$R$_a$, —(CH₂)$_r$NR$_a$S(O)$_p$R$_c$, —(CH₂)$_r$-aryl, —(CH₂)$_r$-heterocycle, and bicyclic heterocycle, each substituted with 0-5 R$_9$;

R₉ is independently selected from F, Cl, Br, C$_{1-4}$alkyl, C$_{2-4}$alkenyl, C$_{2-4}$alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

alternatively, two adjacent R₉ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH₂)$_r$—C$_{3-10}$carbocyclyl substituted with 0-5 R$_e$, and —(CH₂)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH₂)$_r$—C$_{3-10}$carbocyclyl substituted with 0-5 R$_e$, and —(CH₂)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH₂)$_r$—C$_{3-6}$ cycloalkyl, —(CH₂)$_r$-aryl, F, Cl, Br, CN, NO₂, =O, CO₂H, —(CH₂)$_r$OR$_f$, S(O)$_p$R$_f$, C(=O)NR$_f$R$_f$, S(O)$_p$NR$_f$R$_f$, and —(CH₂)$_r$NR$_f$R$_f$;

R$_f$, at each occurrence, is independently selected from H, F, Cl, Br, CN, OH, C$_{1-5}$alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4; provided (1) when Ring A is

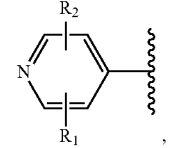

R₃ is not H;

(2) when Ring A is

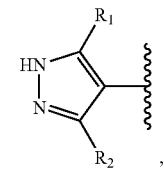

R₃ is not H, Cl, or OPh; and (3) when Ring A is

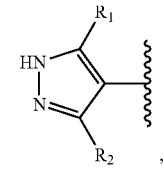

R₅ and R₆ together with the nitrogen atom to which they are both attached does not form a spiro heterocyclyl.

In another aspect, the present invention provides compounds of Formula (I) or stereoisomers, tautomers, pharmaceutically acceptable salts, solvates, or prodrugs thereof, wherein:

$R_3$ is independently selected from H, F, Cl, Br, CN, $C_{1-4}$ alkyl substituted with 0-3 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, and $C_{1-4}$ alkyl substituted with 0-3 $R_e$;

$R_5$ and $R_6$ together with the nitrogen atom to which they are both attached form a heterocyclyl comprising carbon atoms and 1-3 hetero atoms selected from N, $NR_7$, O, and $S(O)_p$ and substituted with 1-5 $R_8$;

$R_7$ is independently selected from H, $C_{1-4}$alkyl substituted with 0-4 $R_e$, —$C(=O)R_b$, —$C(=O)NR_aR_a$, —$C(=O)(CH_2)_rNR_aR_a$, —$C(=O)OR_b$, —$(CH_2)_r$—$C_{3-6}$ carbocyclyl substituted with 0-3 $R_e$, and —$(CH_2)_r$-heterocyclyl substituted with 0-3 $R_e$;

$R_8$ is independently selected from F, Cl, Br, CN, $C_{1-4}$ alkyl substituted with 0-3 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rCN$, —$(CH_2)_rNR_aC(=O)R_b$, —$(CH_2)_rNR_aC(=O)OR_b$, —$(CH_2)_rC(=O)OR_b$, —$(CH_2)_rS(O)_pNR_aR_a$, —$(CH_2)$-aryl, heteroaryl, and bicyclic heterocycle, each substituted with 0-3 $R_9$; and $R_9$ is independently selected from F, Cl, Br, $C_{1-4}$alkyl, nitro, —$(CHR_d)_rS(O)_pR_c$, —$(CHR_d)_rS(O)_pNR_aR_a$, —$(CHR_d)_rNR_aS(O)R$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_r$ $OC(=O)R_b$, —$(CHR_d)_rC(=O)NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$; and other variables are as defined in Formula (I) above.

In another aspect, the present invention provides compounds of Formula (II):

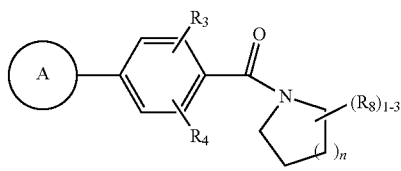

(II)

or stereoisomers, tautomers, pharmaceutically acceptable salts, solvates, or prodrugs thereof, wherein:

Ring A is independently selected from

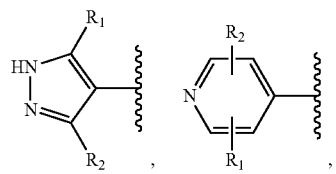

and

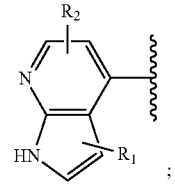

;

$R_1$ is independently selected from H, F, Cl, Br, CN, and $C_{1-4}$alkyl substituted with 0-4 $R_e$;

$R_2$ is independently selected from H, F, Cl, Br, OH, CN, $NR_aR_a$, and $C_{1-4}$alkyl substituted with 0-4 $R_e$;

$R_3$ is independently selected from H, F, Cl, Br, CN, $C_{1-4}$ alkyl substituted with 0-3 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_8$ is independently selected from F, $C_{1-4}$ alkyl substituted with 0-3 $R_e$, —$(CH_2)_rOR_b$, —$(CH_2)_rC(=O)R_b$, —$NR_aR_a$, —$C(=O)NR_aR_a$, —$C(=O)OR_b$, aryl, heteroaryl, and bicyclic heterocycle, each substituted with 0-5 $R_9$;

$R_9$ is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n, at each occurrence, is independently selected from 1, 2, and 3;

p, at each occurrence, is independently selected from zero, 1, and 2; and r, at each occurrence, is independently selected from zero, 1, 2, 3, and 4.

In another aspect, the present invention provides compounds of Formula (II) or stereoisomers, tautomers, pharmaceutically acceptable salts, solvates, or prodrugs thereof, wherein:

$R_8$ is independently selected from F, $C_{1-4}$ alkyl substituted with 0-3 $R_e$, —$(CH_2)_rOR_b$, —$(CH_2)_rC(=O)R_b$, —$NR_aR_a$, —$C(=O)NR_aR_a$, —$C(=O)OR_b$, aryl and bicyclic heterocycle selected from

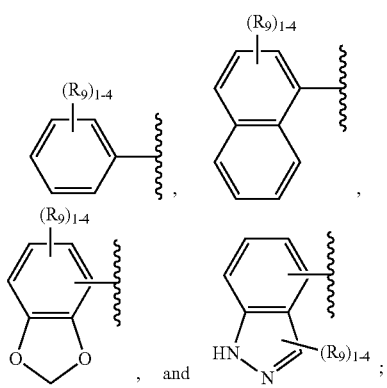

, and $R_9$ is selected independently from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, —$(CH_2)_r$—$C_{3-10}$ cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n, at each occurrence, is independently selected from 1, 2, and 3;

p, at each occurrence, is independently selected from zero, 1, and 2; and r, at each occurrence, is independently selected from zero, 1, 2, 3, and 4; and other variables are as defined in Formula (I) above.

In another aspect, the present invention provides compounds of Formula (III):

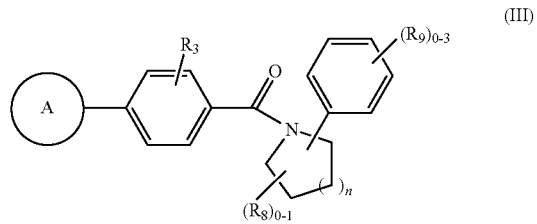

(III)

or stereoisomers, tautomers, pharmaceutically acceptable salts, solvates, or prodrugs thereof, wherein:

Ring A is independently selected from

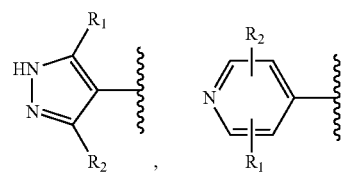

and

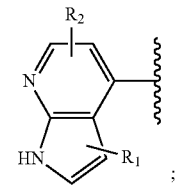

;

$R_1$ is independently selected from H, F, Cl, Br, CN, and $C_{1-4}$alkyl substituted with 0-4 $R_e$;

$R_2$ is independently selected from H, F, Cl, Br, OH, CN, $NR_aR_a$, and $C_{1-4}$alkyl substituted with 0-4 $R_e$;

$R_3$ is independently selected from H, F, Cl, Br, CN, $C_{1-4}$ alkyl substituted with 0-3 $R_e$, —$OR_b$, —$S(O)_pR_e$, —$C(=O)R_b$, —$NR_aR_a$, —$C(=O)NR_aR_a$, —$NR_aC(=O)R_b$, —$OC(=O)NR_aR_a$, —$NR_aC(=O)NR_aR_a$, —$C(=O)OR_b$, and —$S(O)_pNR_aR_a$;

$R_8$ is independently selected from F, $C_{1-4}$ alkyl substituted with 0-3 $R_e$, —$(CH_2)_rOR_b$, —$(CH_2)_rC(=O)R_b$, —$NR_aR_a$, —$C(=O)NR_aR_a$, and —$C(=O)OR_b$;

$R_9$ is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n, at each occurrence, is independently selected from 1, and 2;

p, at each occurrence, is independently selected from zero, 1, and 2; and r, at each occurrence, is independently selected from zero, 1, 2, 3, and 4.

In another aspect, the present invention provides compounds of Formula (IV):

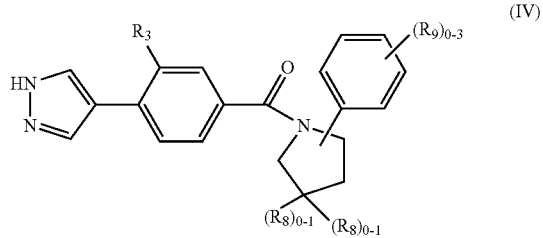

(IV)

or stereoisomers, tautomers, pharmaceutically acceptable salts, solvates, or prodrugs thereof, wherein:

$R_3$ is independently selected from CN, $C_{1-4}$ alkyl substituted with 0-3 $R_e$, and —$OR_b$;

$R_8$ is independently selected from F, $C_{1-4}$ alkyl substituted with 0-3 $R_e$, —$(CH_2)_rOR_b$, —$(CH_2)_rC(=O)R_b$, —$NR_aR_a$, —$C(=O)NR_aR_a$, and —$C(=O)OR_b$;

$R_9$ is independently selected from F, Cl, Br, $C_{1-4}$ alkyl, nitro, —$S(O)_pR_c$, —$S(O)_pNR_aR_a$, —$OR_b$, —$NR_aR_a$, —$C(=O)OR_b$, —$(CH_2)_rC(=O)R_b$, —$C(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (IV) or stereoisomers, tautomers, pharmaceutically acceptable salts, solvates, or prodrugs thereof, wherein:

$R_9$ is independently selected from F, Cl, Br, $C_{1-4}$ alkyl, nitro, —$S(O)R_e$, —$S(O)_pNR_aR_a$, —$OR_b$, —$NR_aR_a$, —$C(=O)OR_b$, —$(CH_2)_rC(=O)R_b$, —$C(=O)NR_aR_a$, —$(CH_2)_r$-cycloalkyl, —$(CH_2)_r$-heterocyclyl, —$(CH_2)_r$-aryl, and —$(CH_2)_r$-heteroaryl selected from

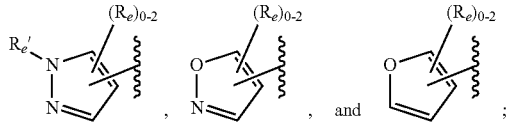

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$; and $R_e'$ is independently selected from H and $C_{1-4}$ alkyl substituted with 0-5 $R_f$; and other variables are as defined in Formula (IV) above.

In another aspect, the present invention provides compounds of Formula (IV) or stereoisomers, tautomers, pharmaceutically acceptable salts, solvates, or prodrugs thereof, wherein:

$R_9$ is —$C(=O)NR_aR_a$;

$R_a$, at each occurrence, is independently selected from H, CN, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl independently selected from

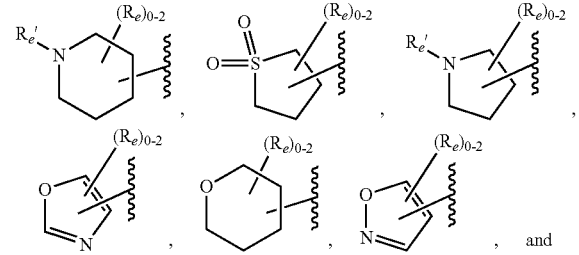

-continued

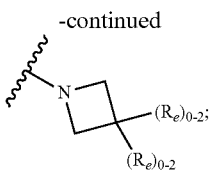

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_e'$ is independently selected from H and $C_{1-4}$ alkyl substituted with 0-5 $R_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4; and other variables are as defined in Formula (IV) above.

In still another aspect, the present invention provides compounds of Formula (V):

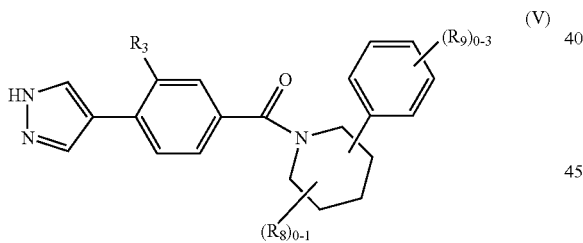

or stereoisomers, tautomers, pharmaceutically acceptable salts, solvates, or prodrugs thereof, wherein:

$R_3$ is independently selected from CN, $C_{1-4}$ alkyl substituted with 0-3 $R_e$, and —$OR_b$;

$R_8$ is independently selected from F, $C_{1-4}$ alkyl substituted with 0-3 $R_e$, —$(CH_2)_rOR_b$, —$(CH_2)_rC(=O)R_b$, —$NR_aR_a$, —$C(=O)NR_aR_a$, and —$C(=O)OR_b$;

$R_9$ is independently selected from F, Cl, Br, $C_{1-4}$ alkyl, nitro, —$S(O)_pR_c$, —$S(O)_pNR_aR_a$, —$OR_b$, —$NR_aR_a$, —$C(=O)OR_b$, —$(CH_2)_rC(=O)R_b$, —$C(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, —$(CH_2)_r$—$C_{3-6}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In still another aspect, the present invention provides compounds of Formula (VI):

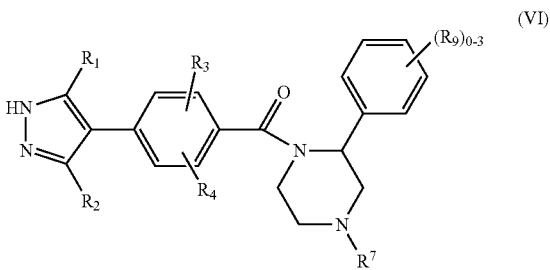

or stereoisomers, tautomers, pharmaceutically acceptable salts, solvates, or prodrugs thereof, wherein:

$R_3$ is independently selected from F, Cl, $C_{1-4}$ alkyl substituted with 0-3 $R_e$, —$OR_b$ and $S(O)_2R_e$;

$R_4$ is independently selected from H, F, methyl, and ethyl;

$R_7$ is independently selected from H, $C_{1-4}$alkyl substituted with 0-4 $R_e$, —$C(=O)R_b$, —$C(=O)NR_aR_a$, —$C(=O)(CH_2)_rNR_aR_a$, and —$C(=O)OR_b$;

$R_9$ is independently selected from F, Cl, Br, $C_{1-4}$ alkyl, $S(O)R_e$, —$OR_b$, —$(CHR_d)_rC(=O)OR_b$, —$(CHR_d)_rC(=O)R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_r OR_f$, and —$(CH_2)_r NR_f R_f$;

$R_f$, at each occurrence, is independently selected from H, F, Cl, Br, CN, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl; and r, at each occurrence, is independently selected from zero, 1, 2, 3, and 4.

In another aspect, the present invention provides compounds of Formula (I) or stereoisomers, tautomers, pharmaceutically acceptable salts, solvates, or prodrugs thereof, wherein:

$R_3$ is independently selected from F, Cl, $C_{1-4}$ alkyl, —$OC_{1-3}$ alkyl and $S(O)_2Me$;

$R_4$ is H;

$R_5$ is independently selected from H and $C_{1-4}$ alkyl;

$R_6$ is independently selected from bicyclic carbocyclyl substituted with 0-3 $R_8$, and heterocyclyl comprising carbon atoms and 1-3 hetero atoms selected from N, $NC_{1-4}$, O, and $S(O)_p$ and substituted with 1-3 $R_8$;

$R_8$ is heteroaryl substituted with 0-5 $R_9$;

$R_9$ is independently selected from F, Cl, Br, $C_{1-4}$ alkyl, $S(O)_p R_c$, —$OR_b$, —$(CHR_d)_r C(=O)OR_b$, —$(CHR_d)_r C(=O)R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_r OR_f$, and —$(CH_2)_r NR_f R_f$;

$R_f$, at each occurrence, is independently selected from H, F, Cl, Br, CN, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl; and r, at each occurrence, is independently selected from zero, 1, 2, 3, and 4.

In another aspect, the present invention provides a compound selected from any subset list of compounds exemplified in the present application.

In another embodiment, the compounds of the present invention have ROCK $IC_{50}$ values ≤10 μM.

In another embodiment, the compounds of the present invention have ROCK $IC_{50}$ values ≤1 μM.

In another embodiment, the compounds of the present invention have ROCK $IC_{50}$ values ≤0.1 μM.

In another embodiment, the compounds of the present invention have ROCK $IC_{50}$ values ≤0.05 μM.

In another embodiment, the compounds of the present invention have ROCK $IC_{50}$ values ≤0.01 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a patient that has not yet presented with a clinical disease state, whereas secondary prevention is defined as preventing a second occurrence of the same or similar clinical disease state. In another embodiment, the present invention provides a combined preparation of a compound of the present invention and additional therapeutic agent(s) for simultaneous, separate or sequential use in therapy.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example, trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology,* 112:309-396, Academic Press (1985);
b) Bundgaard, H., Chapter 5, "Design and Application of Prodrugs", *A Textbook of Drug Design and Development,* pp. 113-191, Krosgaard-Larsen, P. et al., eds., Harwood Academic Publishers (1991);
c) Bundgaard, H., *Adv. Drug Deliv. Rev.,* 8:1-38 (1992);
d) Bundgaard, H. et al., *J. Pharm. Sci.,* 77:285 (1988); and
e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or S(O)H group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.
Me Methyl Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonylmethanimidate
CBz Carbobenzyloxy
$CH_2Cl_2$ Dichloromethane
$CH_3CN$ or ACN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or Hunig's base diisopropylethylamine
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH Ethanol
GMF glass microfiber filter
Grubbs (II) (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH Methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ Ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
i-PrOH or IPA isopropanol
PS polystyrene
SEM-Cl 2-(trimethysilyl)ethoxymethyl chloride
$SiO_2$ silica oxide
$SnCl_2$ tin(II) chloride
TBAI tetra-n-butylammonium iodide
TEA triethylamine
TFA trifluoroacetic acid
THF tetrahydrofuran
$TMSCHN_2$ trimethylsilyldiazomethane
T3P® propane phosphonic acid anhydride
TRIS tris (hydroxymethyl) aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL assay containing 20 mM HEPES, pH 7.5, 20 mM $MgCl_2$, 0.015% Brij-35, 4 mM DTT, 5 μM ATP and 1.5 μM peptide substrate (FITC-AHA-AKRRRLSSLRA-OH). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the $IC_{50}$, i.e., the concentration of compound required to inhibit 50% of kinase activity.

Representative Examples were tested in the ROCK assay described above and found having ROCK inhibitory activity. A range of ROCK inhibitory activity ($IC_{50}$ values) of ≤50 μM (50000 nM) was observed. Table A below lists the ROCK $IC_{50}$ values measured for the following examples.

TABLE A

| Example No. | ROCK2 $IC_{50}$ (nM) |
|---|---|
| 1 | 789 |
| 2 | 355 |
| 3 | 1340 |
| 4 | 31.8 |
| 5 | 32.2 |
| 6 | 511 |
| 7 | 1430 |
| 8 | 85.8 |
| 9 | 673 |
| 10 | 114 |
| 11 | 1630 |
| 12 | 12.6 |
| 13 | 800 |
| 14 | 183 |
| 15 | 31.0 |
| 16 | 3.57 |
| 17 | 1280 |
| 18 | 2.79 |
| 19 | 41.4 |
| 20 | 14.7 |
| 21 | 2.74 |
| 22 | 125 |
| 23 | 215 |
| 24 | 1100 |
| 25 | 331 |
| 26 | 50.5 |
| 27 | 61.4 |
| 28 | 15.8 |
| 29 | 68.3 |
| 30 | 75.3 |
| 31 | 11.6 |
| 32 | 5.83 |
| 33 | 151 |
| 34 | 4.49 |
| 35 | 4.89 |
| 36 | 1.53 |
| 37 | 751 |
| 38 | 2.13 |
| 39 | 4.52 |
| 40 | 725 |
| 41 | 5.53 |
| 42 | 4.59 |
| 43 | 54.4 |
| 44 | 49.7 |
| 45 | 8.29 |
| 46 | 18.2 |
| 47 | 7.29 |
| 48 | 5.32 |
| 49 | 43.4 |
| 50 | 5.10 |
| 51 | 2.71 |
| 52 | 6.68 |
| 53 | 102 |
| 54 | 5.09 |
| 55 | 2.50 |
| 56 | 7.17 |
| 57 | 43.4 |
| 58 | 5.32 |
| 59 | 1.80 |
| 60 | 4.08 |
| 61 | 102 |
| 62 | 316 |
| 63 | 5.25 |
| 64 | 204 |
| 65 | 91.4 |
| 66 | 4.35 |
| 67 | 293 |

TABLE A-continued

| Example No. | ROCK2 $IC_{50}$ (nM) |
|---|---|
| 68 | 60.2 |
| 69 | 3.59 |
| 70 | 1.28 |
| 71 | 54.9 |
| 72 | 1600 |
| 73 | 1530 |
| 74 | 901 |
| 75 | 1570 |
| 76 | 320 |
| 77 | 887 |
| 78 | 4.70 |
| 79 | 24.3 |
| 80 | 5.40 |
| 81 | 158 |
| 82 | 56.8 |
| 83 | 153 |
| 84 | 24.1 |
| 86 | 5.42 |
| 87 | 461 |
| 88 | 10.6 |
| 89 | 784 |
| 90 | 86.0 |
| 91 | 55.0 |
| 92 | 8.03 |
| 93 | 4.52 |
| 94 | 73.3 |
| 95 | 44.1 |
| 95 | 28.4 |
| 96 | 667 |
| 97 | 721 |
| 98 | 723 |
| 99 | 614 |
| 100 | 228 |
| 101 | 65.1 |
| 102 | 411 |
| 103 | 62.0 |
| 104 | 1390 |
| 105 | 278 |
| 106 | 0.87 |
| 107 | 1.65 |
| 108 | 7.65 |
| 109 | 902 |
| 110 | 463 |
| 111 | 504 |
| 112 | 15.2 |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example, as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimenter or the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 4th Edition, Wiley-Interscience (2006)).

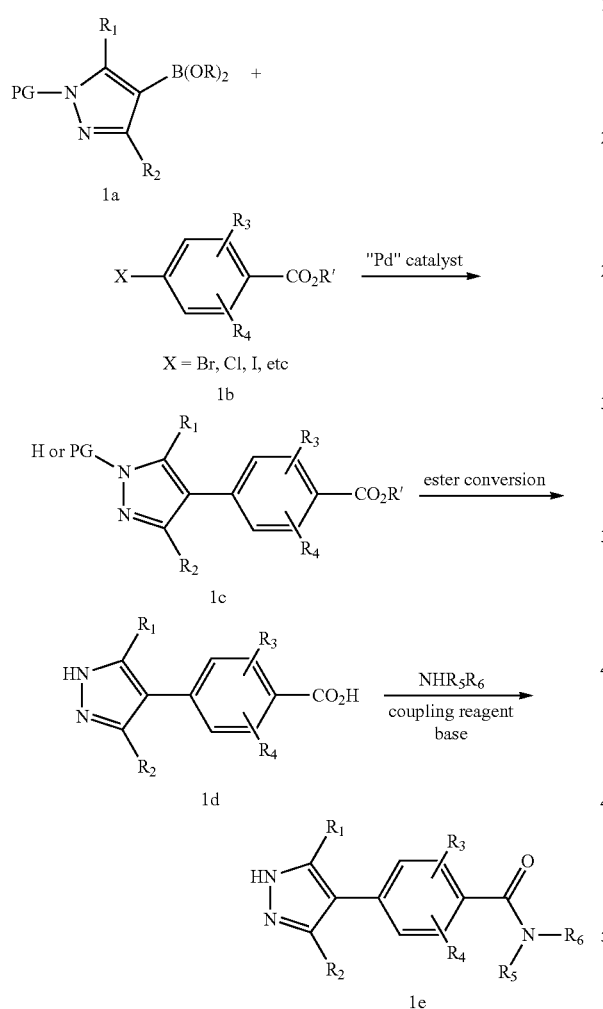

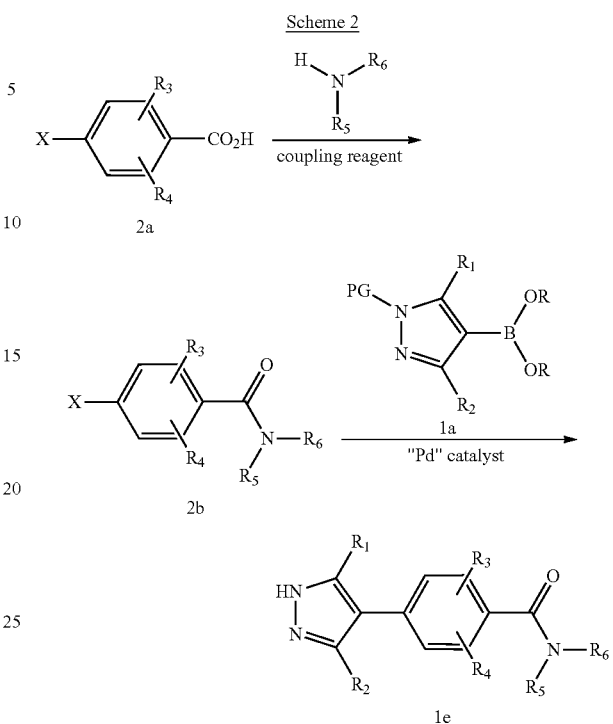

Alternatively, compounds with generic structure 1e can be prepared as shown in Scheme 2. Amide coupling between substituted aryl carboxylic acids 2a with amines affords 2b under amide formation conditions, such as using HATU or EDC as the coupling reagent with a base such as DIEA or TEA. Suzuki-Miyaura coupling between aryl halides 2b and pyrazole boronic acid derivatives 1a in the presence of a base such as $K_3PO_4$ and a catalyst such as $PdCl_2(dppf)$ affords target compounds 1e.

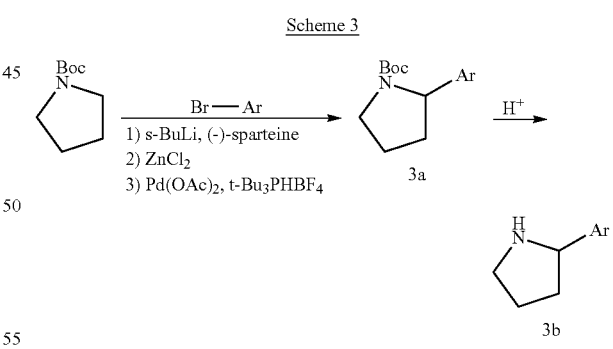

Scheme 1 shows the synthesis of generic compound 1e from the common intermediate 1d. Suzuki-Miyaura coupling between pyrazole boronic acid or boronate 1a and aryl halide, or other Suzuki coupling reaction partners 1b, in the presence of a base such as $K_3PO_4$, and a Pd catalyst such as $PdCl_2(dppf)$, affords intermediate 1c. Ester 1c is converted to acid intermediate 1d under basic, such as LiOH (R'=Me, Et, etc.), or acidic, such as TFA (R'=tert-Bu), or hydrogenation conditions (R'=Bn). Amide formation provides target 1e by coupling intermediate 1d with an appropriate amine in the presence of a coupling reagent, such as HATU or EDC, and a base such as DIEA.

General structure of 2-arylpyrrolidine derivatives 3b can be prepared according to Scheme 3 by following a similar procedure as described in literature (*JACS*, 128:3538 (2006)). When N-Boc pyrrolidine is treated with s-BuLi at the presence of (−)-sparteine, followed by addition of $ZnCl_2$, then coupled with aryl bromides with the catalysis of a palladium catalyst, such as $Pd(OAc)_2$, with a phosphine ligand such as $t-Bu_3PHBF_4$, 2-Aryl pyrrolidine derivative 3a is provided. Removal of the Boc protecting group using an acid, such as TFA, provides amine 3b.

Scheme 4

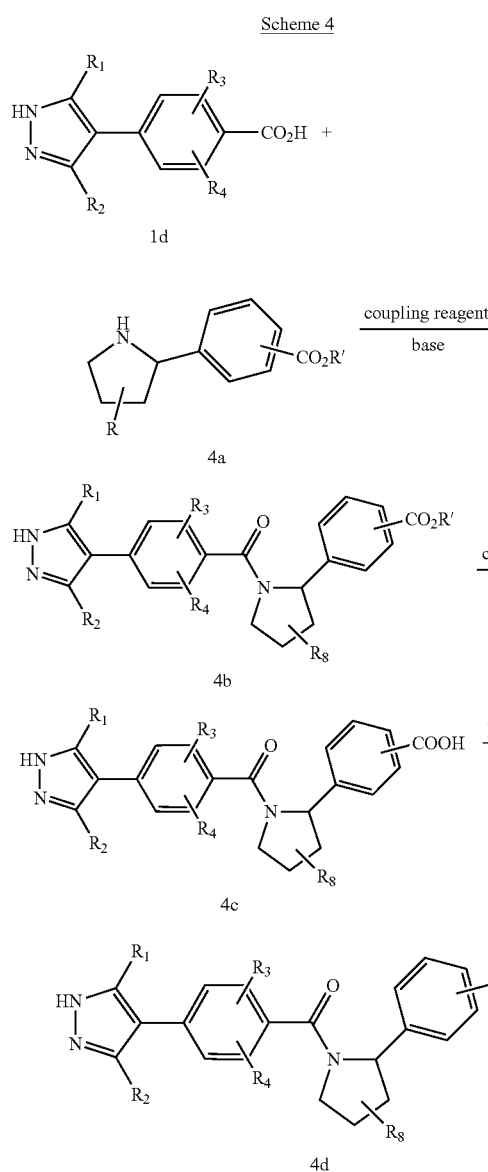

Compounds with general structure 4d can be prepared according to Scheme 4. Amide coupling of 1d with 4a provides amide 4b. Ester in 4b is converted to acid 4c using base or acid hydrolysis to provide 4c. Amide formation provides target 4d by coupling intermediate 4c with an appropriate amine in the presence of a coupling reagent, such as HATU or EDC, and a base such as DIEA.

Scheme 5

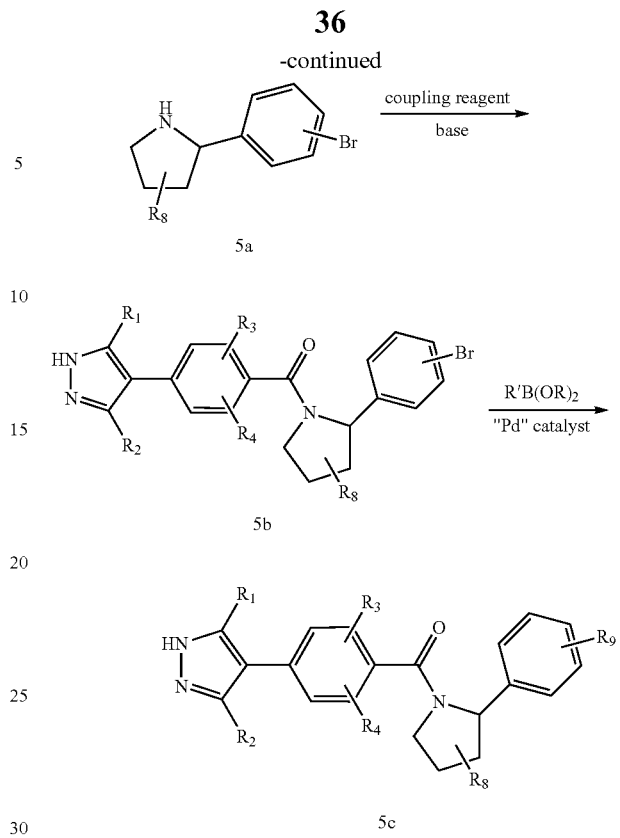

Compounds with general structure 5c can be prepared according to Scheme 5. Amide coupling of 1d with 5a provides amide 5b. Suzuki-Miyaura coupling between 5b and boronic acid derivatives in the presence of a base, such as $K_3PO_4$, and a catalyst such as $PdCl_2(dppf)$, affords target compounds 5c.

Scheme 6

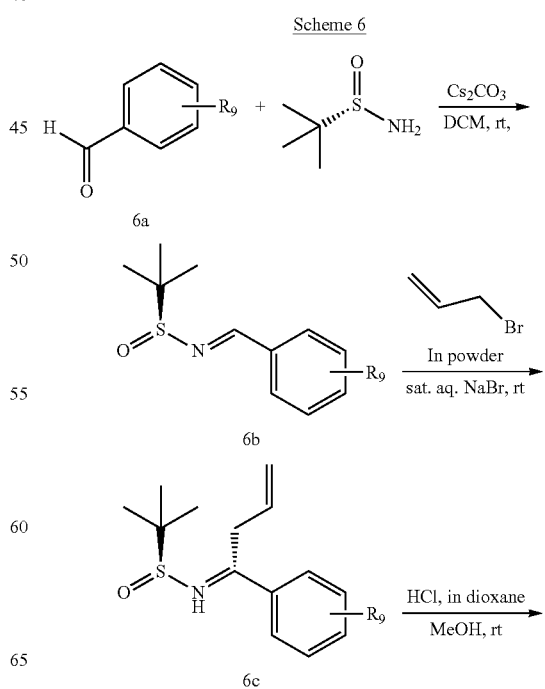

Scheme 7

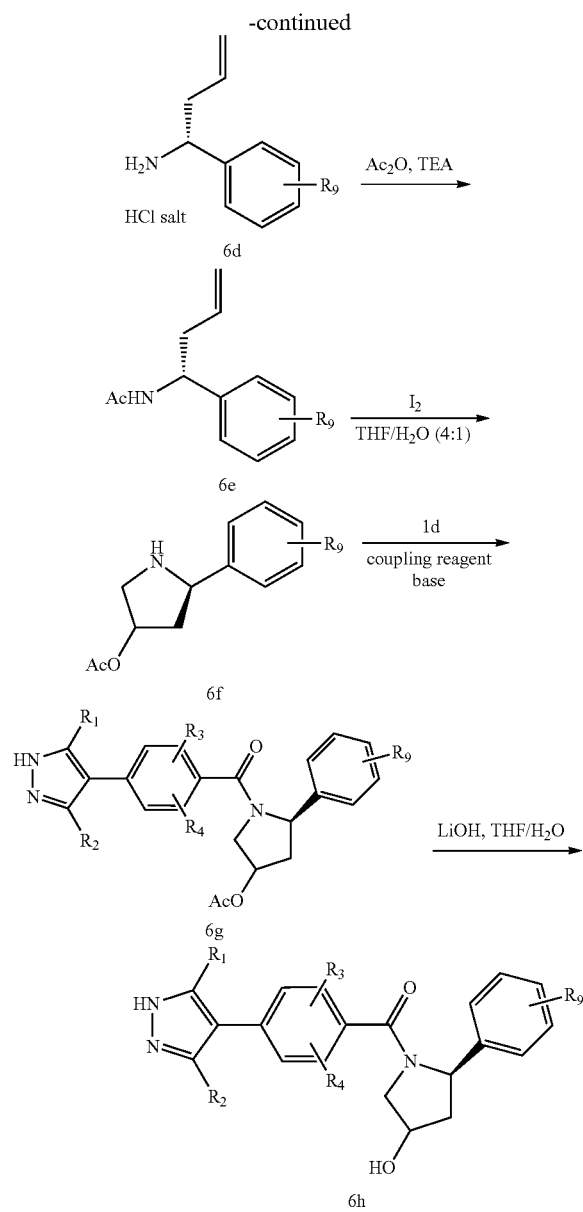

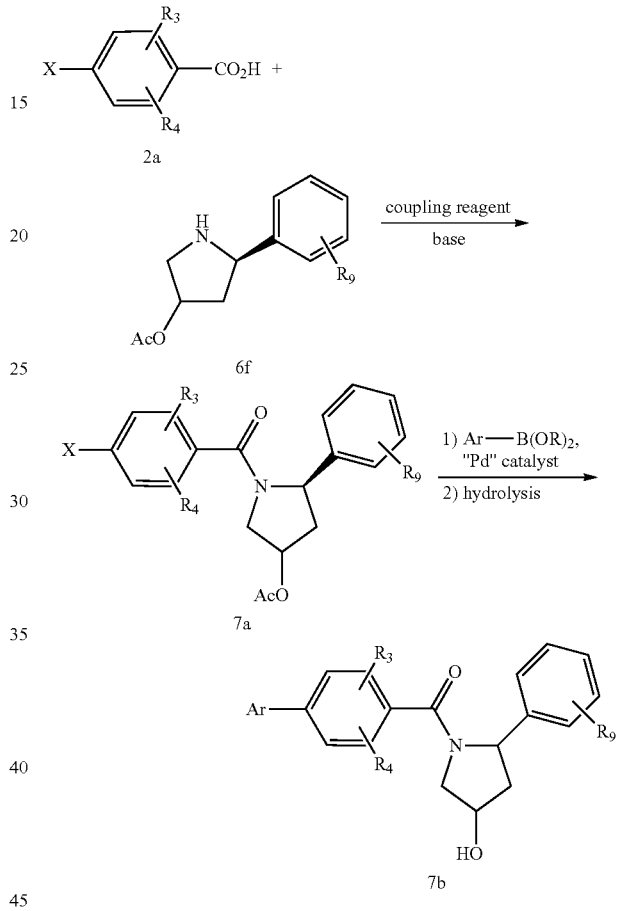

removed by treating with an acid, such as HCl in dioxane, provides amine 6d. Acetylation of 6d with acetic anhydride provides allyl acetamide 6e. Treating 6e with iodine in THF/H₂O with a basic aqueous workup provides acetoxy pyrrolidine intermediate 6f. Amide coupling of 6f with 1d provides amide 6g. Hydrolysis of acetate 6g under an aqueous basic condition provides target 6h.

Compounds with general structure 6h can be prepared according to Scheme 6. Condensation of aldehyde 6a with tert-butyl sulfinamide provides sulfinamide intermediate 6b. When treated with allylbromide and indium powder, 6b is converted to allyl sulfinamine 6c. The sulfinyl group is Compounds with general structure 7b can be prepared according to Scheme 7. Amide coupling between 2a and 6f provides amide 7a. Suzuki-Miyaura coupling between 7a and boronic acid derivatives in the presence of a base such as K₃PO₄, and a catalyst such as PdCl₂(dppf), followed by aqueous basic hydrolysis of the acetate provides 7b.

Scheme 8

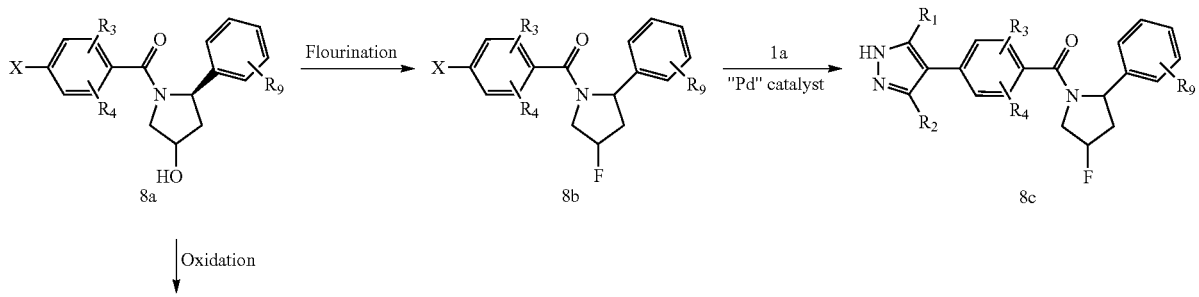

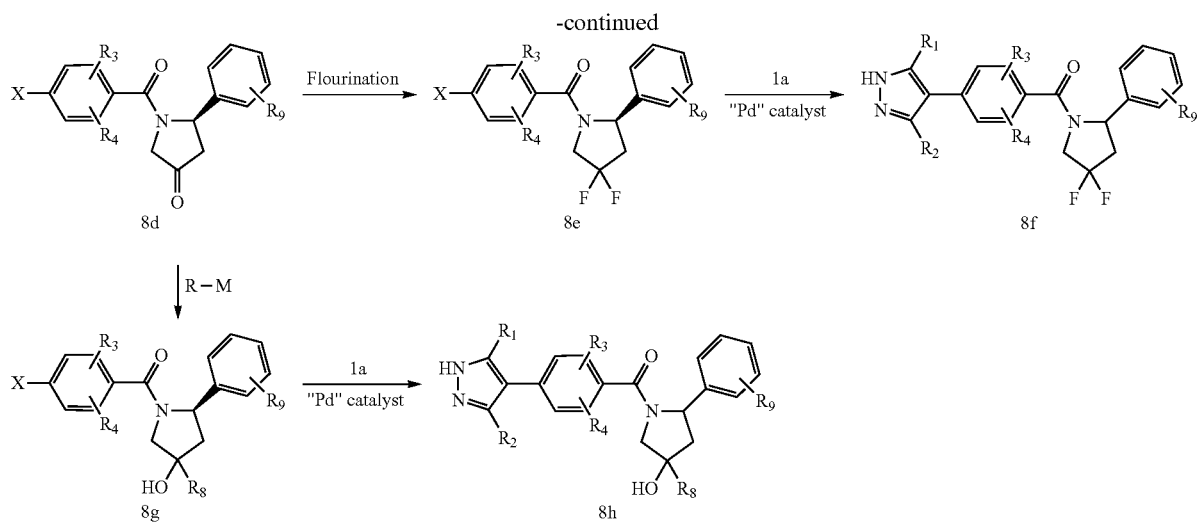

Compounds with general structure 8c, 8f and 8h can be prepared according to Scheme 8. When intermediate 8a, prepared by the hydrolysis of 7a, is treated with a fluorination reagent, such as DAST, provides fluoride 8b. Suzuki-Miyaura coupling between 8b and boronic acid derivative 1a in the presence of a base such as $K_3PO_4$, and a catalyst such as $PdCl_2(dppf)$, or XPhos-G2 palladium precatalyst, provides 8c. When 8a is treated under an oxidation condition, such as Swern or Dess-Martin, ketone 8d is provided. Ketone 8d can react subsequently with a fluorination reagent, such as DAST, to give difluoride 8e, which is subsequently converted to 8f using Suzuki-Miyaura coupling. When 8d is treated with an alkyl or aryl metal reagent, such as a Grignard reagent or alkyl/aryl lithium reagent, alcohol 8g is provided. After Suzuki-Miyaura coupling, 8h is obtained.

Scheme 9

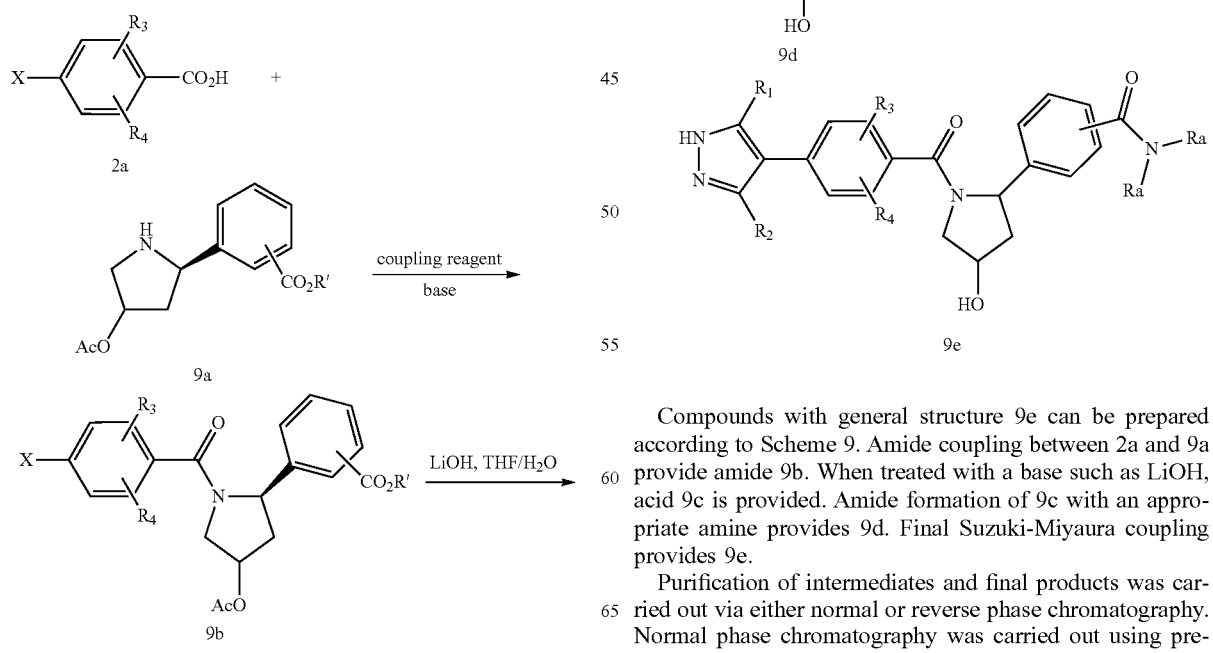

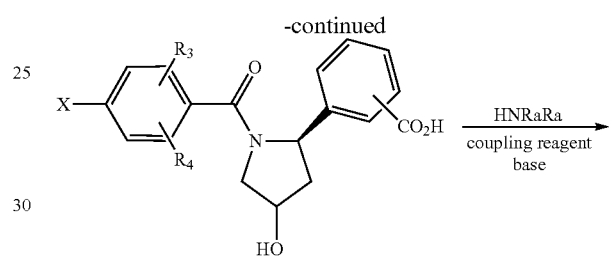

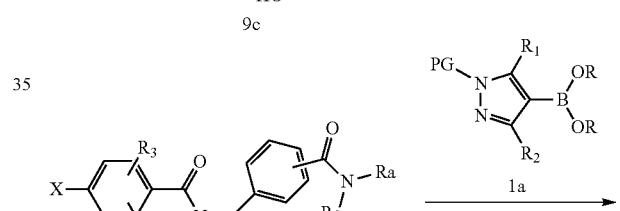

Compounds with general structure 9e can be prepared according to Scheme 9. Amide coupling between 2a and 9a provide amide 9b. When treated with a base such as LiOH, acid 9c is provided. Amide formation of 9c with an appropriate amine provides 9d. Final Suzuki-Miyaura coupling provides 9e.

Purification of intermediates and final products was carried out via either normal or reverse phase chromatography. Normal phase chromatography was carried out using prepacked $SiO_2$ cartridges eluting with either gradients of hexanes and EtOAc or DCM and MeOH unless otherwise indicated. Reverse phase preparative HPLC was carried out using C18 columns eluting with gradients of Solvent A (90% H₂O, 10% MeOH, 0.1% TFA) and Solvent B (10% H₂O, 90% MeOH, 0.1% TFA, UV 220 nm) or with gradients of Solvent A (90% H₂O, 10% ACN, 0.1% TFA) and Solvent B (10% H₂O, 90% ACN, 0.1% TFA, UV 220 nm) or with gradients of Solvent A (98% H₂O, 2% ACN, 0.05% TFA) and Solvent B (98% ACN, 2% H₂O, 0.05% TFA, UV 220 nm) (or) SunFire Prep C18 OBD 5μ 30×100 mm, 25 min gradient from 0-100% B. A=H₂O/ACN/TFA 90:10:0.1. B=ACN/H₂O/TFA 90:10:0.1 (or) Waters XBridge C18, 19×200 mm, 5-μm particles; Guard Column: Waters XBridge C18, 19×10 mm, 5-μm particles; Solvent A: water with 20-mM ammonium acetate; Solvent B: 95:5 acetonitrile:water with 20-mM ammonium acetate; Gradient: 25-65% B over 20 minutes, then a 5-minute hold at 100% B; Flow: 20 mL/min or with gradients of Solvent A (5:95 acetonitrile:water with 0.1% formic acid) and Solvent B (95:5 acetonitrile:water with 0.1% formic acid).

Unless otherwise stated, analysis of final products was carried out by reverse phase analytical HPLC.

Method A: SunFire C18 column (3.5 μm C18, 3.0×150 mm). Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method B: XBridge Phenyl column (3.5 μm C18, 3.0×150 mm). Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method C: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min.

Method D: Waters BEH C18, 2.1×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

Method E: Waters BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes; Flow: 1.11 mL/min.

Method F: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.11 mL/min.

Intermediate 1:
3-Methoxy-4-(1H-pyrazol-4-yl)benzoic acid

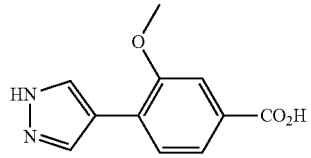 [SMILES: COc1cc(C(=O)O)ccc1-c1cn[nH]c1]

Intermediate 1A: Methyl 3-methoxy-4-(1H-pyrazol-4-yl)benzoate

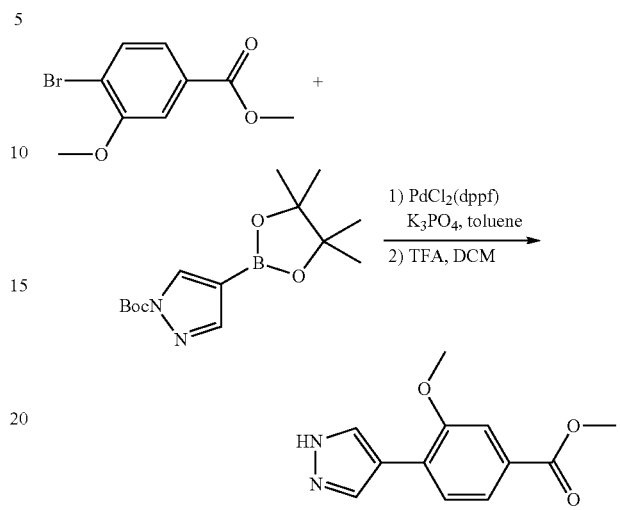

To a solution of methyl 4-bromo-3-methoxybenzoate (1.32 g, 5.39 mmol) in dioxane (30 mL) and water (5 mL) were added tert-butyl 4-(4,4,5,5-tetramethyl-1,3,2-dioxaborolan-2-yl)-1H-pyrazole-1-carboxylate (1.901 g, 6.46 mmol), potassium phosphate (2.86 g, 13.47 mmol) and PdCl₂(dppf) (0.197 g, 0.269 mmol) at rt. The reaction was stirred under argon at 100° C. for 3 h. The reaction mixture was diluted with EtOAc, washed with H₂O. The organic phase was dried over sodium sulfate, filtered and concentrated. The residue was dissolved in DCM (10 mL) and TFA (5 mL) was added. The reaction was stirred at rt for 1.5 h. The solvent was removed. The residue was taken into EtOAc, which was washed with NaHCO₃ and brine, dried over Na₂SO₄, filtered and concentrated. The crude product was purified by normal phase chromatography. The desired product was isolated as white solid (0.86 g, 69% yield). LCMS(ESI) m/z: 233.0 (M+H)⁺; ¹H NMR (400 MHz, CDCl₃) δ 8.13 (s, 2H), 7.73-7.66 (m, 1H), 7.66-7.56 (m, 2H), 3.98 (s, 3H), 3.94 (s, 3H).

Intermediate 1

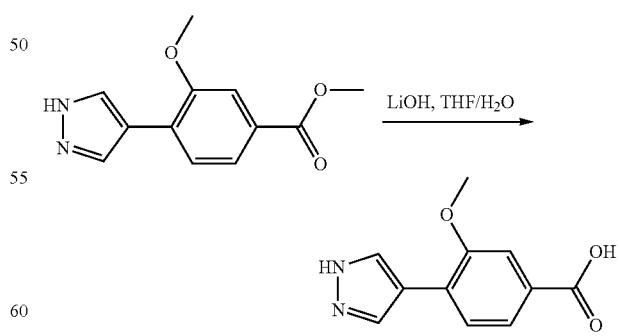

To a solution of Intermediate 1A (860 mg, 3.70 mmol) in THF (10 mL) and water (5 mL) was added LiOH (133 mg, 5.55 mmol) at rt. The reaction was stirred under argon at rt for 5 h. The reaction was neutralized with 1 N HCl solution. The solvent was removed to give a pale solid of crude product of Intermediate 1 (810 mg, 100% yield), which was used without further purification. LCMS(ESI) m/z: 219.0 (M+H)+; 1H NMR (400 MHz, DMSO-d6) δ 7.91 (br. s, 2H), 7.54 (br. s, 1H), 7.43 (br. s, 2H), 3.84 (s, 3H).

Intermediate 2:
2-Methoxy-4-(1H-pyrazol-4-yl)benzoic acid

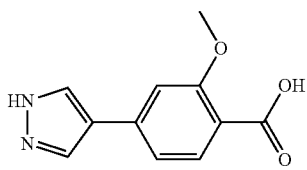 [SMILES: COc1cc(-c2cn[nH]c2)ccc1C(=O)O]

Intermediate 2 was synthesized by following a similar route to Intermediate 1 using methyl 4-bromo-2-methoxybenzoate in step 1A. LCMS(ESI) m/z: 219.1 (M+H)+.

Intermediate 3: Methyl 3-((2R)-4-acetoxypyrrolidin-2-yl)benzoate

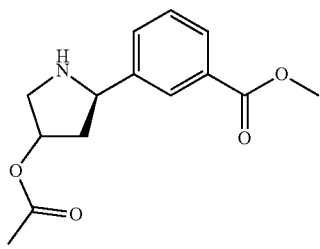

Intermediate 3A: (S)-Methyl 3-(((tert-butylsulfinyl)imino)methyl)benzoate

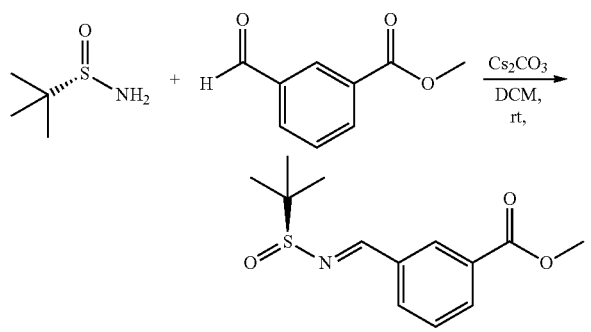

To a stirred suspension of (S)-2-methylpropane-2-sulfinamide (1.36 g, 11.22 mmol) and Cs2CO3 (5.48 g, 16.83 mmol) in DCM (30 mL) was added a solution of methyl 3-formylbenzoate (2.026 g, 12.34 mmol) dropwise. The solution was then stirred at rt overnight. The reaction was filtered through a pad of CELITE®. The solvent was removed. The crude product was purified by normal phase chromatography to afford Intermediate 3A as colorless oil (2.82 g, 94%). LC-MS(ESI) m/z: 268.0[M+H]+; 1H NMR (400 MHz, CDCl3) δ 8.59 (s, 1H), 8.45 (t, J=1.5 Hz, 1H), 8.13 (dt, J=7.8, 1.4 Hz, 1H), 8.00 (dt, J=7.7, 1.4 Hz, 1H), 7.52 (t, J=7.8 Hz, 1H), 3.91 (s, 3H), 1.23 (s, 9H).

Intermediate 3B: Methyl 3-((R)-1-((S)-1,1-dimethylethylsulfinamido)but-3-en-1-yl)benzoate

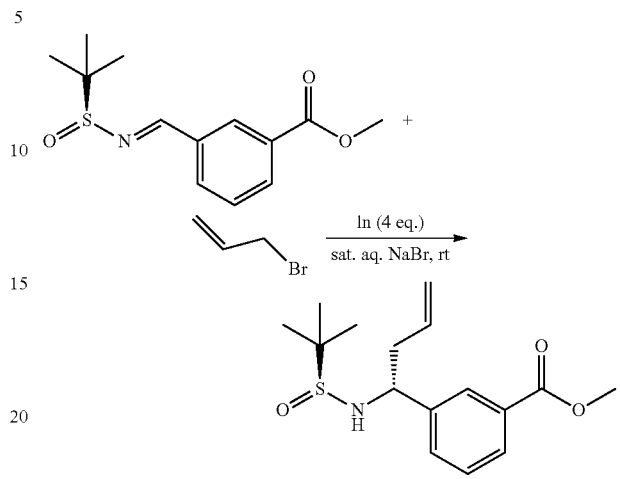

To a suspension of indium powder (3.95 g, 34.4 mmol) and Intermediate 3A (2.3 g, 8.60 mmol) in a saturated aqueous NaBr solution (80 mL) was added allyl bromide (2.98 ml, 34.4 mmol) at rt. The reaction suspension was stirred at rt overnight. The reaction was quenched with 15 mL sat. NaHCO3. The suspension was filtered and extracted with EtOAc. The organic phase was dried over Na2SO4, filtered and concentrated. Purification by normal phase chromatography afforded Intermediate 3B as a white solid (2.70 g, 100%). LC-MS(ESI) m/z: 310[M+H]+; 1H NMR (400 MHz, CDCl3) δ 8.02 (t, J=1.8 Hz, 1H), 7.95 (dt, J=7.6, 1.5 Hz, 1H), 7.50 (dt, J=7.7, 1.4 Hz, 1H), 7.44-7.37 (m, 1H), 5.80-5.62 (m, 1H), 5.25-5.11 (m, 2H), 4.53 (ddd, J=8.0, 5.6, 2.2 Hz, 1H), 3.91 (s, 3H), 3.69 (d, J=1.5 Hz, 1H), 2.74-2.37 (m, 2H), 1.19 (s, 9H).

Intermediate 3C: (R)-Methyl 3-(1-aminobut-3-en-1-yl)benzoate

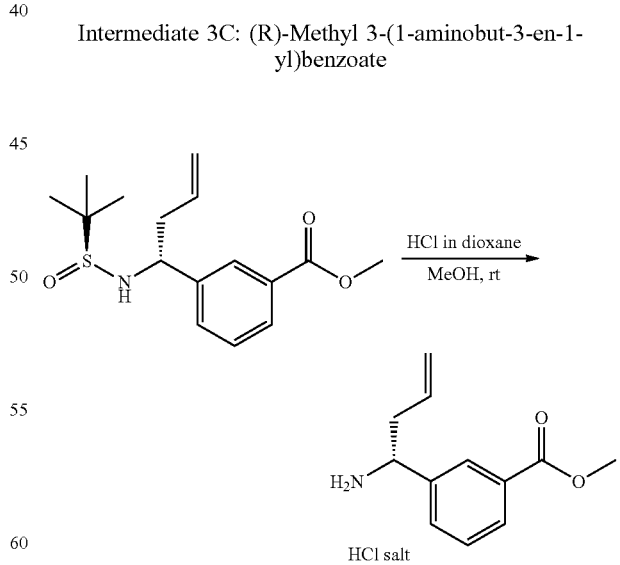

To a solution of Intermediate 3B (2.7 g, 8.73 mmol) in MeOH (25 mL) was added HCl solution (4 M in dioxane, 8.73 mL, 34.9 mmol) at rt. The reaction was stirred under argon at rt for 3 h. The solvent was removed, and the product was dried in vacuo to give Intermediate 3C as an off-white solid (2.11 g, 100%). LC-MS(ESI) m/z: 206.0[M+H]+; 1H NMR (400 MHz, CD3OD) δ 8.13 (s, 1H), 8.07 (d, J=7.7 Hz, 1H), 7.70 (d, J=7.5 Hz, 1H), 7.64-7.53 (m, 1H), 5.85-5.57 (m, 1H), 5.32-5.06 (m, 2H), 4.47 (t, J=7.3 Hz, 1H), 3.93 (s, 3H), 2.90-2.59 (m, 2H).

Intermediate 3D: (R)-Methyl 3-(1-acetamidobut-3-en-1-yl)benzoate

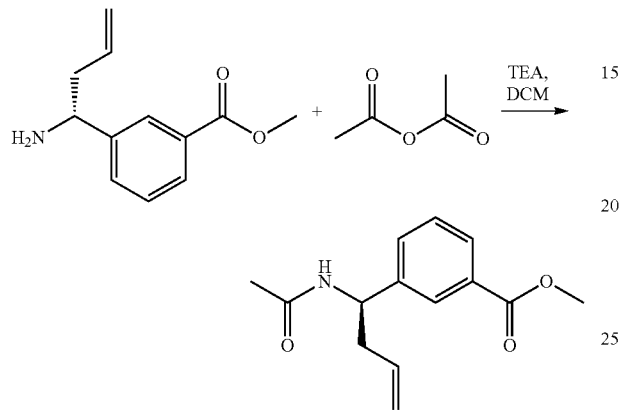

To a solution of Intermediate 3C (500 mg, 2.069 mmol) in DCM (10 mL) were added TEA (1.442 ml, 10.35 mmol) and Ac2O (0.234 ml, 2.482 mmol) at 0° C. The reaction was stirred under argon at 0° C. for 1 h. The reaction mixture was diluted with DCM, washed with 1 M HCl and brine. The organic phase was dried over Na2SO4, filtered and concentrated. The crude product was purified by normal phase chromatography to afford Intermediate 3D as a white solid (505 mg, 99%). LC-MS(ESI) m/z: 248.2[M+H]+; 1H NMR (400 MHz, chloroform-d) δ 7.98-7.89 (m, 2H), 7.51-7.44 (m, 1H), 7.43-7.36 (m, 1H), 5.84 (d, J=7.0 Hz, 1H), 5.66 (ddt, J=17.1, 10.2, 7.0 Hz, 1H), 5.23-5.02 (m, 3H), 3.91 (s, 3H), 2.65-2.48 (m, 2H), 2.01 (s, 3H).

Intermediate 3

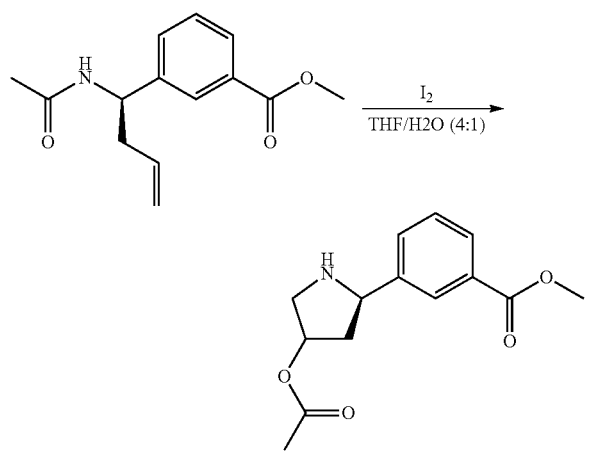

To a solution of Intermediate 3D (150 mg, 0.607 mmol) in THF (4 mL) and water (1 mL) was added I2 (462 mg, 1.820 mmol) at rt. The reaction was stirred under argon at rt overnight. To the reaction was added saturated NaHCO3 (10 mL), and stirring was continued at rt for 1 h. The reaction mixture was diluted with EtOAc, washed with saturated Na2S2O3 and brine. The organic phase was dried over Na2SO4, filtered and concentrated to give Intermediate 3 as a solid (165 mg, 100%). LC-MS(ESI) m/z: 264.1[M+H]+; 1H NMR (400 MHz, CD3OD) δ 8.16-8.06 (m, 1H), 8.00-7.94 (m, 1H), 7.71-7.64 (m, 1H), 7.54-7.47 (m, 1H), 5.44-5.30 (m, 1H), 4.58-4.29 (m, 1H), 3.91 (s, 3H), 3.60 (dd, J=12.8, 5.5 Hz, 0.7H), 3.28 (d, J=1.5 Hz, 1H), 3.26-3.07 (m, 0.3H), 2.83-2.36 (m, 1H), 2.21-2.11 (m, 1H), 2.09 (s, 3H). 1H NMR indicated a diastereomer ratio ~2:1.

Intermediate 4: (5R)-5-(3-(Methylsulfonyl)phenyl)pyrrolidin-3-yl acetate

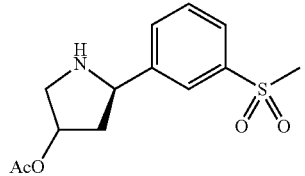

Intermediate 4 was prepared by following a similar procedure as described in Intermediate 3, by replacing 3-formylbenzoate with 3-(methylsulfonyl)benzaldehyde in step 3A. LC-MS(ESI) m/z: 284.0 [M+H]+; 1H NMR (400 MHz, CD3OD) δ 8.03 (s, 1H), 7.92 (d, J=7.7 Hz, 1H), 7.77 (d, J=7.9 Hz, 1H), 7.67 (d, J=7.9 Hz, 1H), 5.48-5.31 (m, 1H), 4.62 (dd, J=10.9, 6.3 Hz, 1H), 3.21-3.11 (m, 5H), 2.48 (dd, J=14.1, 6.2 Hz, 1H), 2.10-2.07 (m, 3H), 2.00-1.91 (m, 1H).

Intermediate 5: (5R)-5-(2-Fluorophenyl)pyrrolidin-3-yl acetate

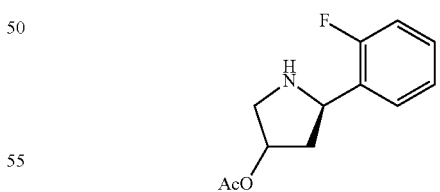

Intermediate 5 was prepared by following a similar procedure as described in Intermediate 3, by replacing 3-formylbenzoate with 2-fluorobenzaldehyde in step 3A. LC-MS(ESI) m/z: 224.0[M+H]+; 1H NMR (400 MHz, CD3OD) δ 7.46 (td, J=7.6, 1.7 Hz, 1H), 7.29 (ddd, J=7.5, 5.7, 1.3 Hz, 1H), 7.20-7.15 (m, 1H), 7.09 (ddd, J=10.9, 8.3, 1.1 Hz, 1H), 5.38-5.25 (m, 1H), 4.59 (dd, J=10.3, 6.4 Hz, 1H), 3.50 (dd, J=12.5, 5.5 Hz, 1H), 3.07-2.95 (m, 1H), 2.33 (ddd, J=14.0, 6.5, 0.9 Hz, 1H), 2.07 (s, 3H).

Intermediate 6: 3-(Difluoromethoxy)-4-(1H-pyrazol-4-yl)benzoic acid

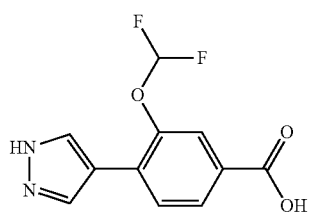 [SMILES: O=C(O)c1ccc(-c2cn[nH]c2)c(OC(F)F)c1]

Intermediate 6A: Methyl 4-bromo-3-(difluoromethoxy)benzoate

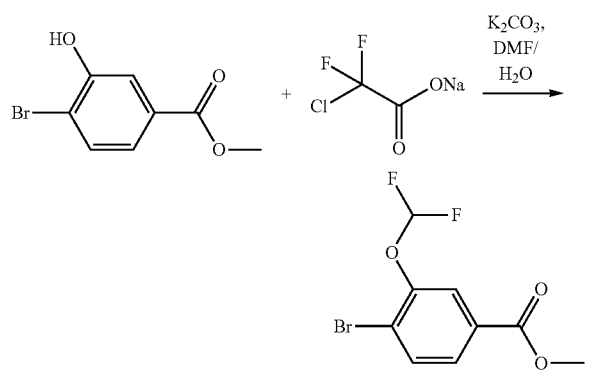

To a solution of methyl 4-bromo-3-hydroxybenzoate (0.66 g, 2.9 mmol) in DMF (9 mL) and water (1 mL) were added sodium 2-chloro-2,2-difluoroacetate (1.7 g, 11 mmol) and K₂CO₃ (0.79 g, 5.7 mmol) at rt. The reaction was stirred under argon at 100° C. for 4 h, and then was cooled to rt. The reaction mixture was diluted with EtOAc, washed with H₂O and brine. The organic phase was dried over sodium sulfate, filtered and concentrated. The crude product was purified by normal phase chromatography to afford Intermediate 6A (0.62 g, 77%) as a white solid. LCMS(ESI) m/z: 280.9/282.0 [M+H]⁺; ¹H NMR (400 MHz, CDCl₃) δ 7.87-7.83 (m, 1H), 7.79-7.74 (m, 1H), 7.73-7.66 (m, 1H), 6.59 (t, J=73.1 Hz, 1H), 3.93 (s, 3H).

Intermediate 6B: Methyl 3-(difluoromethoxy)-4-(1H-pyrazol-4-yl)benzoate

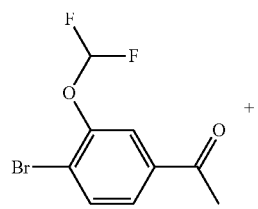

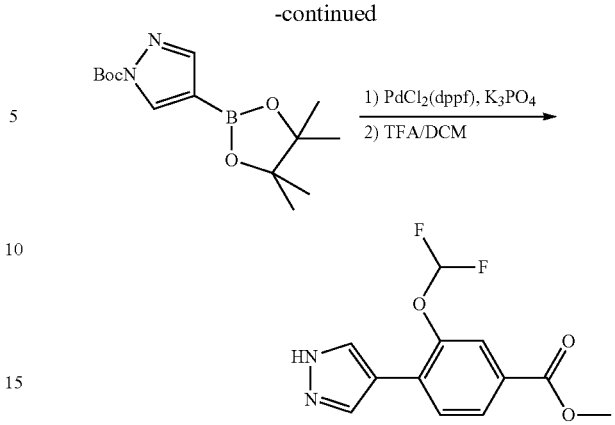

To a solution of Intermediate 6A (0.22 g, 0.78 mmol) in dioxane (8 mL) and water (2 mL) were added tert-butyl 4-(4,4,5,5-tetramethyl-1,3,2-dioxaborolan-2-yl)-1H-pyrazole-1-carboxylate (0.28 g, 0.94 mmol), K₃PO₄ (0.42 g, 2.0 mmol) and PdCl₂(dppf) (29 mg, 0.039 mmol) at rt. The reaction was stirred under argon at 90° C. for 2 h, and was cooled to rt. The reaction mixture was diluted with EtOAc, washed with H₂O. The organic phase was concentrated. To the residue were added DCM (3 mL) and TFA (1 mL). It was stirred at rt for 1 h, and the solvent was removed. The crude product was purified by normal phase chromatography to afford Intermediate 6B (0.12 g, 59%) as a light brown solid. (ESI) m/z: 269.0 [M+H]⁺; ¹H NMR (400 MHz, CDCl₃) δ 8.12 (br. s., 2H), 7.91 (dd, J=8.1, 1.5 Hz, 1H), 7.83 (s, 1H), 7.68 (d, J=8.1 Hz, 2H), 6.81-6.37 (t, J=72 Hz, 1H), 3.94 (s, 3H).

Intermediate 6

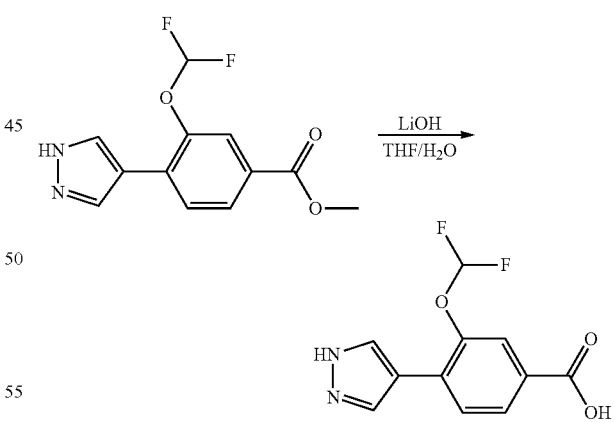

To a solution of Intermediate 6B (0.12 g, 0.46 mmol) in THF (4 mL) and water (1 mL) was added LiOH (55 mg, 2.3 mmol) at rt. The reaction was stirred under argon at rt for 18 h. The solvent was removed under reduced pressure, and the residue was dried in vacuo to afford Intermediate 6 (0.12 g, 100%) as off-white solid. LC-MS(ESI) m/z: 255.0[M+H]⁺; ¹H NMR (400 MHz, DMSO-d₆) δ 7.76 (s, 2H), 7.61 (d, J=8.8 Hz, 1H), 7.58 (s, 1H), 7.46 (d, J=7.9 Hz, 1H), 6.98 (t, J=75.7 Hz, 1H).

Intermediate 7:
3-Cyano-4-(1H-pyrazol-4-yl)benzoic acid

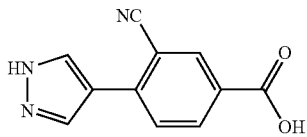 [SMILES: N#Cc1cc(C(=O)O)ccc1-c1cn[nH]c1]

Intermediate 7A: Methyl 4-bromo-3-cyanobenzoate

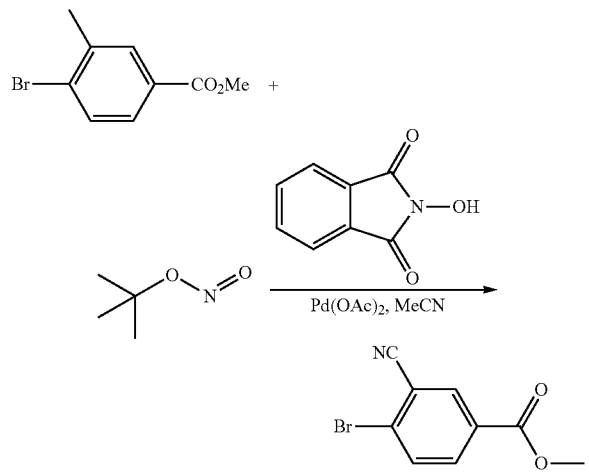

To a solution of methyl 4-bromo-3-methylbenzoate (1.2 g, 5.0 mmol) in acetonitrile (5 mL) were added 2-hydroxy-isoindoline-1,3-dione (0.82 g, 5.0 mmol), Pd(OAc)$_2$ (56 mg, 0.25 mmol) and tert-butyl nitrite (1.8 mL, 15 mmol) at rt. The reaction was stirred under argon at 80° C. for 24 h, and then was cooled to rt. The reaction mixture was diluted with EtOAc, washed with H$_2$O and brine. The organic phase was dried over sodium sulfate, filtered and concentrated. The crude product was purified by normal phase chromatography to give Intermediate 8A (0.65 g, 54%) as a white solid. LC-MS(ESI) m/z: 249.9/241.9 [M+H]$^+$; $^1$H NMR (400 MHz, CDCl$_3$) δ 8.31 (d, J=1.8 Hz, 1H), 8.09 (dd, J=8.5, 2.1 Hz, 1H), 7.79 (d, J=8.4 Hz, 1H), 3.96 (s, 3H).

Intermediate 7B: Methyl 3-cyano-4-(1H-pyrazol-4-yl)benzoate

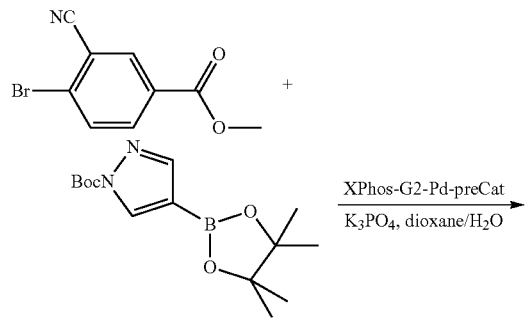

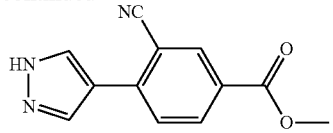

To a solution of Intermediate 7A (0.25 g, 1.0 mmol) in dioxane (10 mL) were added tert-butyl 4-(4,4,5,5-tetramethyl-1,3,2-dioxaborolan-2-yl)-1H-pyrazole-1-carboxylate (0.37 g, 1.3 mmol), K$_3$PO$_4$ (1 M, 3.1 ml, 3.1 mmol) and XPhos-G2-Pd-PreCat (16 mg, 0.021 mmol) at rt. The reaction was stirred under argon at 90° C. for 2 h. The reaction was cooled to rt. The reaction mixture was diluted with EtOAc, washed with H$_2$O and brine. The organic phase was dried over sodium sulfate, filtered and concentrated. The crude product was purified by normal phase chromatography to give Intermediate 7B (0.22 g, 93%) as a white solid. LC-MS(ESI) m/z: 228.1[M+H]$^+$; $^1$H NMR (400 MHz, CDCl$_3$) δ 11.27 (br. s., 1H), 8.37 (d, J=1.8 Hz, 1H), 8.27-8.17 (m, 3H), 7.70 (d, J=8.1 Hz, 1H), 3.97 (s, 3H).

Intermediate 7

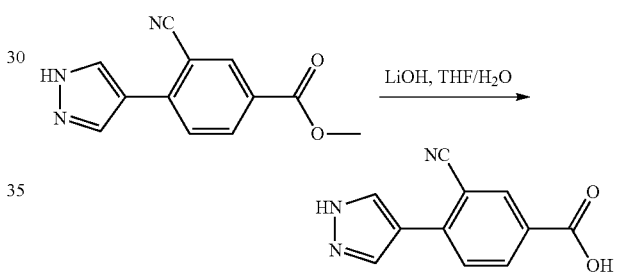

To a solution of Intermediate 7B (0.22 g, 0.97 mmol) in THF (7 mL) and water (3 mL) was added LiOH (70 mg, 2.9 mmol) at rt. The reaction was stirred under argon at rt for 5 h. The reaction was neutralized with 1.0 N HCl. The solvent was removed to give Intermediate 7 (0.21 g, 100%) as a white solid. LC-MS(ESI) m/z: 214.1[M+H]$^+$; $^1$H NMR (400 MHz, DMSO-d$_6$) δ 8.02 (d, J=1.5 Hz, 1H), 7.95-7.87 (m, 3H), 7.47 (d, J=8.1 Hz, 1H).

Example 1: 4-[2-Methoxy-4-(2-phenylpyrrolidine-1-carbonyl)phenyl]-1H-pyrazole

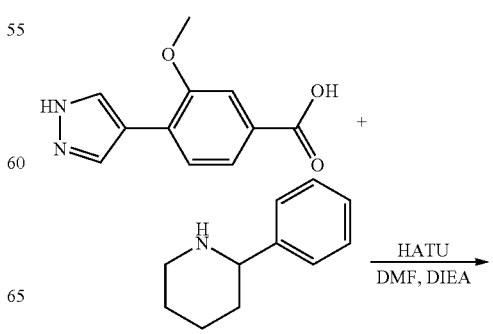

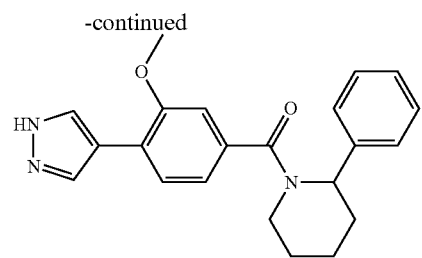

To a solution of Intermediate 1 (15 mg, 0.069 mmol) in DMF (1.5 mL) were added 2-phenylpiperidine (13.30 mg, 0.082 mmol), DIEA (0.060 mL, 0.344 mmol) and HATU (28.8 mg, 0.076 mmol) at rt. The crude product was purified by reverse phase chromatography to afford Example 1 (21.1 mg, 78%). LC-MS(ESI) m/z: 362.2[M+H]+; 1H NMR (500 MHz, DMSO-$d_6$) δ 8.05 (br. s., 2H), 7.64 (br. s., 1H), 7.46-7.36 (m, 2H), 7.34-7.21 (m, 3H), 7.02 (d, J=15.0 Hz, 2H), 3.73 (br. s., 1H), 3.69 (br. s., 3H), 2.85-2.73 (m, 1H), 2.37 (br. s., 1H), 1.96-1.14 (m, 6H). Analytical HPLC RT=1.61 min (Method E), 1.69 min (Method F).

The following Examples in Table 1 were prepared by using the same procedure as described in Example 1 by coupling Intermediate 1 with the appropriate amines. Various coupling reagents could be used other than the one described in Example 1 such as HATU, T3P®, BOP, PyBop, EDC/HOBt.

TABLE 1

| Ex. No. | Structure | Name | LCMS (M + H)+ | HPLC Method, RT (min.) | 1H NMR (ppm) |
|---|---|---|---|---|---|
| 2 | 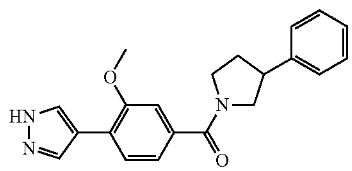 [SMILES: COc1cc(C(=O)N2CCC(c3ccccc3)C2)ccc1-c1cn[nH]c1] | 4-[2-methoxy-4-(3-phenyl-pyrrolidine-1-carbonyl)phenyl]-1H-pyrazole | 348.3 | C: 2.29 D: 3.57 | (500 MHz, DMSO-$d_6$) δ 8.08 (br. s., 2H), 7.68 (dd, J = 17.9, 7.8 Hz, 1H), 7.42-7.10 (m, 7H), 3.91 (two singlets, 3H), 3.98-3.43 (m, 5H), 2.37-2.19 (m, 1H), 2.13-1.95 (m, 1H) |
| 3 | 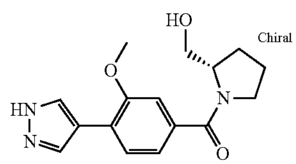 [SMILES: COc1cc(C(=O)N2CCC[C@H]2CO)ccc1-c1cn[nH]c1] | [(2S)-1-[3-methoxy-4-(1H-pyrazol-4-yl)benzoyl]pyrrolidin-2-yl]methanol | 302.5 | C: 1.42 D: 2.46 | (500 MHz, DMSO-$d_6$) δ 8.09 (br. s., 2H), 7.67 (d, J = 7.6 Hz, 1H), 7.15 (br. s., 1H), 7.09 (d, J = 6.1 Hz, 1H), 4.78 (br. s., 1H), 4.15 (br. s., 1H), 3.91 (s, 3H), 3.70-3.44 (m, 4H), 2.05-1.61 (m, 4H) |
| 4 | 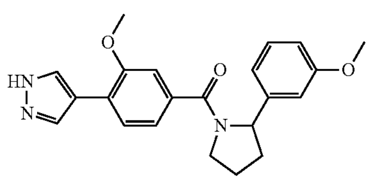 [SMILES: COc1cccc(C2CCCN2C(=O)c2ccc(-c3cn[nH]c3)c(OC)c2)c1] | 4-{2-methoxy-4-[2-(3-methoxyphenyl)pyrrolidine-1-carbonyl]phenyl}-1H-pyrazole | 378.2 | E: 1.41 F: 1.46 | (500 MHz, DMSO-$d_6$) δ 8.23-7.97 (m, 2H), 7.78-7.46 (m, 1H), 7.36-7.06 (m, 2H), 7.03-6.42 (m, 4H), 5.18-4.90 (m, 1H), 3.92 (br. s., 3H), 3.76 (br. s., 3H), 3.85-3.40 (m, 2H), 2.44-2.21 (m, 1H), 1.95-1.67 (m, 3H) |
| 5 | 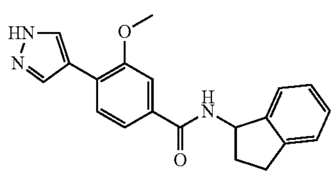 [SMILES: COc1cc(C(=O)NC2CCc3ccccc32)ccc1-c1cn[nH]c1] | N-(2,3-dihydro-1H-inden-1-yl)-3-methoxy-4-(1H-pyrazol-4-yl)benzamide | 334.2 | E: 1.50 F: 1.44 | (500 MHz, DMSO-$d_6$) δ 8.77 (d, J = 8.1 Hz, 1H), 8.13 (s, 2H), 7.72 (d, J = 8.1 Hz, 1H), 7.59 (s, 1H), 7.56 (s, 1H), 7.32-7.26 (m, 1H), 7.21 (d, J = 7.1 Hz, 3H), 5.59 (q, J = 8.1 Hz, 1H), 3.93 (s, 3H), 3.06-2.93 (m, 1H), 2.89-2.79 (m, 1H), 2.46 (br. s., 1H), 2.07-1.94 (m, 1H) |
| 6 | 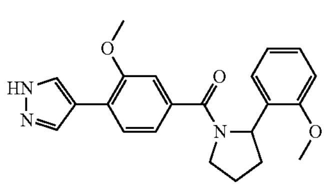 [SMILES: COc1cc(C(=O)N2CCCC2c2ccccc2OC)ccc1-c1cn[nH]c1] | 4-{2-methoxy-4-[2-(2-methoxyphenyl)pyrrolidine-1-carbonyl]phenyl}-1H-pyrazole | 378.2 | E: 1.52 F: 1.46 | (500 MHz, DMSO-$d_6$) δ 8.11 (s, 2H), 8.01 (s, 2H), 7.70 (d, J = 7.7 Hz, 1H), 7.51 (d, J = 7.7 Hz, 1H), 7.30-7.14 (m, 6H), 7.00 (d, J = 7.7 Hz, 2H), 6.93 (d, J = 7.7 Hz, 2H), 6.84 (d, J = 7.7 Hz, 1H), 6.68 (s, 1H), 5.36 (br. s., 1H), 5.10 (d, J = 7.1 Hz, 1H), 3.92 (s, 3H), 3.85 (s, 3H), 3.83-3.68 (m, 4H), 3.64 (s, 3H), 3.38 (s, 3H), 2.32 (dd, J = 12.5, 6.7 Hz, 1H), 2.16 (d, J = 7.1 Hz, 1H), 1.96-1.60 (m, 6H) |
| 7 | 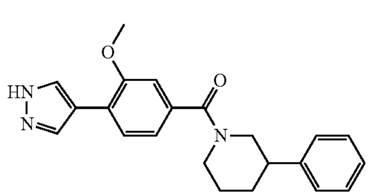 [SMILES: COc1cc(C(=O)N2CCCC(c3ccccc3)C2)ccc1-c1cn[nH]c1] | 1-[3-methoxy-4-(1H-pyrazol-4-yl)benzoyl]-3-phenylpiperidine | 362.2 | E: 1.51 F: 1.57 | (500 MHz, DMSO-$d_6$) δ 8.10 (br. s., 2H), 7.68 (br. s., 1H), 7.44-7.12 (m, 5H), 7.07 (s, 1H), 7.00 (d, J = 7.7 Hz, 1H), 3.91 (s, 3H), 3.80-3.51 (m, 1H), 3.26-3.00 (m, 2H), 2.78 (br. s., 2H), 1.96 (d, J = 12.1 Hz, 1H), 1.89-1.44 (m, 3H) |

TABLE 1-continued

| Ex. No. | Structure | Name | LCMS (M + H)+ | HPLC Method, RT (min.) | 1H NMR (ppm) |
|---|---|---|---|---|---|
| 8 | 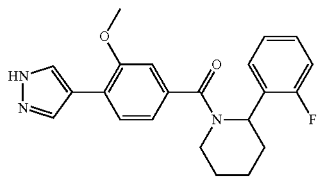 [SMILES: COc1cc(C(=O)N2CCCCC2c2ccccc2F)ccc1-c1cn[nH]c1] | 2-(2-fluorophenyl)-1-[3-methoxy-4-(1H-pyrazol-4-yl)benzoyl]piperidine | 380.2 | E: 1.62 F: 1.70 | (400 MHz, DMSO-d$_6$) δ 12.99 (br. s., 1H), 8.19 (d, J = 13.0 Hz, 1H), 8.04 (d, J = 6.4 Hz, 1H), 7.72 (d, J = 8.1 Hz, 1H), 7.52 (t, J = 7.5 Hz, 1H), 7.45-7.37 (m, 1H), 7.33 (dd, J = 7.6, 1.2 Hz, 1H), 7.25 (ddd, J = 11.7, 8.1, 1.1 Hz, 1H), 7.06-6.95 (m, 2H), 5.64 (br. s., 1H), 4.28-3.98 (m, 1H), 3.85 (br. s., 3H), 3.33-3.20 (m, 1H), 2.20 (d, J = 11.9 Hz, 1H), 2.09-1.93 (m, 1H), 1.79-1.43 (m, 4H) |
| 9 | 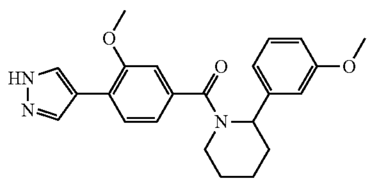 [SMILES: COc1cccc(C2CCCCN2C(=O)c2ccc(-c3cn[nH]c3)c(OC)c2)c1] | 1-[3-methoxy-4-(1H-pyrazol-4-yl)benzoyl]-2-(3-methoxyphenyl)piperidine | 392.2 | E: 1.60 F: 1.68 | (400 MHz, DMSO-d$_6$) δ 12.93 (br. s., 1H), 8.07 (br. s., 2H), 7.68 (d, J = 7.7 Hz, 1H), 7.35 (t, J = 7.9 Hz, 1H), 7.08 (s, 1H), 7.01 (d, J = 7.7 Hz, 1H), 6.93 (d, J = 7.7 Hz, 1H), 6.87 (dd, J = 8.1, 2.4 Hz, 1H), 6.84 (s, 1H), 3.85 (br. s., 3H), 3.78 (s, 3H), 2.90-2.77 (m, 1H), 2.41 (d, J = 13.6 Hz, 1H), 2.01-1.27 (m, 6H) |
| 10 | 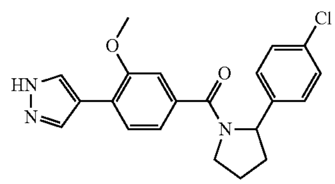 [SMILES: COc1cc(C(=O)N2CCCC2c2ccc(Cl)cc2)ccc1-c1cn[nH]c1] | 4-{4-[2-(4-chlorophenyl)pyrrolidine-1-carbonyl]-2-methoxyphenyl}-1H-pyrazole | 382.2 | E: 1.57 F: 1.64 | (500 MHz, DMSO-d$_6$) δ 8.16-7.95 (m, 2H), 7.73-7.44 (m, 1H), 7.39-7.27 (m, 3H), 7.22-7.03 (m, 2H), 6.85-6.60 (m, 1H), 5.17-4.86 (m, 1H), 3.93-3.46 (m, 5H), 2.42-2.18 (m, 1H), 1.97-1.64 (m, 3H) |
| 11 (Enant. 1) | 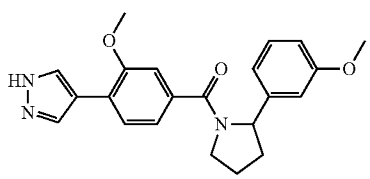 [SMILES: COc1cccc(C2CCCN2C(=O)c2ccc(-c3cn[nH]c3)c(OC)c2)c1] | 4-{2-methoxy-4-[2-(3-methoxyphenyl)pyrrolidine-1-carbonyl]phenyl}-1H-pyrazole | 378.1 | A: 7.18 B: 6.59 | (400 MHz, CD$_3$OD) δ 8.11, 8.01 (br. s, 2H), 7.78-7.48 (m, 1H), 7.31-7.16 (m, 2H), 6.99-6.57 (m, 4H), 5.28-4.93 (m, 1H), 3.98, 3.72 (s, 3H), 3.95-3.82 (m, 2H), 3.81, 3.49 (s, 3H), 2.56-2.27 (m, 1H), 2.10-1.85 (m, 3H) |
| 12 (Enant. 2) | 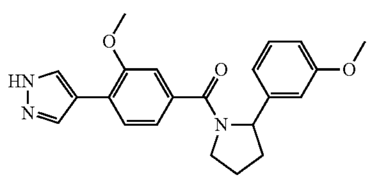 [SMILES: COc1cccc(C2CCCN2C(=O)c2ccc(-c3cn[nH]c3)c(OC)c2)c1] | 4-{2-methoxy-4-[2-(3-methoxyphenyl)pyrrolidine-1-carbonyl]phenyl}-1H-pyrazole | 378.1 | A: 7.20 B: 6.63 | (400 MHz, CD$_3$OD) δ 8.27-7.88 (m, 2H), 7.7, 7.61 (d, J = 8.6 Hz, 1H), 7.33-7.16 (m, 2H), 6.99-6.56 (m, 4H), 5.28-4.93 (m, 1H), 3.98, 3.71 (s, 3H), 3.95-3.82 (m, 2H), 3.81, 3.49 (s, 3H), 2.55-2.28 (m, 1H), 2.10-1.84 (m, 3H) |
| 13 | 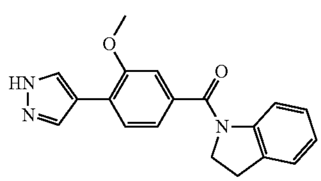 [SMILES: COc1cc(C(=O)N2CCc3ccccc32)ccc1-c1cn[nH]c1] | 1-[3-methoxy-4-(1H-pyrazol-4-yl)benzoyl]-2,3-dihydro-1H-indole | 320.1 | E: 1.33 F: 1.36 | (500 MHz, DMSO-d$_6$) δ 8.14 (br. s., 2H), 7.74 (d, J = 8.1 Hz, 1H), 7.33-7.23 (m, 2H), 7.18 (d, J = 6.7 Hz, 2H), 7.04 (br. s., 1H), 4.08 (t, J = 8.1 Hz, 2H), 3.92 (s, 3H), 3.10 (t, J = 8.1 Hz, 2H) |
| 14 | 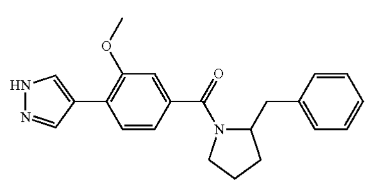 [SMILES: COc1cc(C(=O)N2CCCC2Cc2ccccc2)ccc1-c1cn[nH]c1] | 4-[4(2-benzyl-pyrrolidine-1-carbonyl)-2-methoxyphenyl]-1H-pyrazole | 362.3 | E: 1.54 F: 1.49 | (500 MHz, DMSO-d$_6$) δ 8.11 (br. s., 2H), 7.70 (d, J = 7.7 Hz, 1H), 7.41-7.31 (m, 2H), 7.31-7.20 (m, 2H), 7.19-7.03 (m, 3H), 4.42-4.10 (m, 1H), 3.91 (br. s., 3H), 3.48-3.26 (m, 1H), 3.17 (d, J = 9.4 Hz, 1H), 2.86-2.76 (m, 1H), 1.99-1.80 (m, 2H), 1.79-1.55 (m, 3H) |
| 15 | 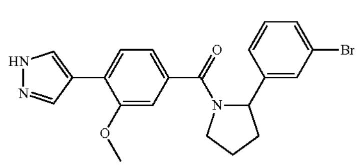 [SMILES: COc1cc(C(=O)N2CCCC2c2cccc(Br)c2)ccc1-c1cn[nH]c1] | 4-{4-[2-(3-bromophenyl)pyrrolidine-1-carbonyl]-2-methoxyphenyl}-1H-pyrazole | 426.1/ 428.1 | E: 1.59 F: 1.55 | (500 MHz, DMSO-d$_6$) δ 8.22-7.96 (m, 2H), 7.71 (d, J = 7.7 Hz, 1H), 7.60-7.47 (m, 1H), 7.44-7.33 (m, 2H), 7.33-7.09 (m, 3H), 5.21-4.86 (m, 1H), 3.99-3.50 (m, 4H), 3.11-2.90 (m, 1H), 2.45-2.12 (m, 1H), 1.91-1.70 (m, 3H) |

TABLE 1-continued

| Ex. No. | Structure | Name | LCMS (M + H)+ | HPLC Method, RT (min.) | 1H NMR (ppm) |
|---|---|---|---|---|---|
| 16 | 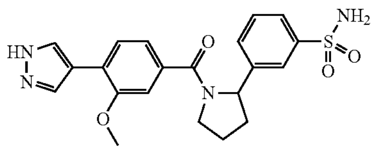 [SMILES: COc1cc(C(=O)N2CCCC2c2cccc(S(N)(=O)=O)c2)ccc1-c1cn[nH]c1] | 3-{1-[3-methoxy-4-(1H-pyrazol-4-yl)benzoyl]pyrrolidin-2-yl}benzene-1-sulfonamide | 427.2 | E: 1.02 F: 1.00 | (500 MHz, DMSO-d6) δ 8.17-7.95 (m, 2H), 7.82-7.13 (m, 7H), 5.25-5.00 (m, 1H), 4.01-3.29 (m, 5H), 2.48-2.22 (m, 1H), 2.03-1.58 (m, 3H) |
| 17 (Enant. 1) | 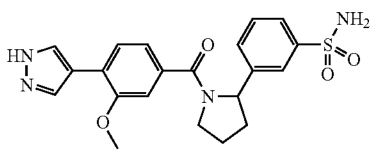 [SMILES: COc1cc(C(=O)N2CCCC2c2cccc(S(N)(=O)=O)c2)ccc1-c1cn[nH]c1] | 3-{1-[3-methoxy-4-(1H-pyrazol-4-yl)benzoyl]pyrrolidin-2-yl}benzene-1-sulfonamide | 427.2 | E: 1.03 F: 1.07 | (500 MHz, DMSO-d6) δ 8.23-7.94 (m, 2H), 7.82-7.62 (m, 3H), 7.61-7.48 (m, 2H), 7.47-7.11 (m, 4H), 5.28-4.98 (m, 1H), 3.91 (s, 3H), 3.39 (br. s., 2H), 2.46-2.24 (m, 1H), 2.01-1.62 (m, 3H) |
| 18 (Enant. 2) | 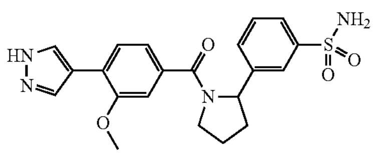 [SMILES: COc1cc(C(=O)N2CCCC2c2cccc(S(N)(=O)=O)c2)ccc1-c1cn[nH]c1] | 3-{1-[3-methoxy-4-(1H-pyrazol-4-yl)benzoyl]pyrrolidin-2-yl}benzene-1-sulfonamide | 427.2 | E: 1.03 F: 1.07 | (500 MHz, DMSO-d6) δ 8.04 (br. s., 2H), 7.80-7.62 (m, 2H), 7.62-7.37 (m, 3H), 7.34-6.60 (m, 2H), 5.26-4.95 (m, 1H), 3.91 (s, 3H), 3.61 (br. s., 2H), 2.48-2.25 (m, 1H), 2.00-1.65 (m, 3H) |
| 19 | 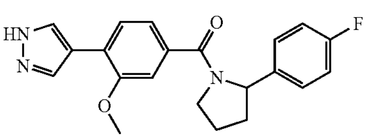 [SMILES: COc1cc(C(=O)N2CCCC2c2ccc(F)cc2)ccc1-c1cn[nH]c1] | 4-{4-[2-(4-fluorophenyl)pyrrolidine-1-carbonyl]-2-methoxyphenyl}-1H-pyrazole | 366.2 | E: 1.38 F: 1.40 | (500 MHz, DMSO-d6) δ 8.19-7.99 (m, 2H), 7.71 (d, J = 8.1 Hz, 1H), 7.40 (br. s., 1H), 7.28-7.06 (m, 4H), 6.87-6.65 (m, 1H), 5.23-4.90 (m, 1H), 4.00-3.85 (m, 3H), 3.83-3.71 (m, 2H), 2.45-2.18 (m, 1H), 2.00-1.65 (m, 3H) |
| 20 | 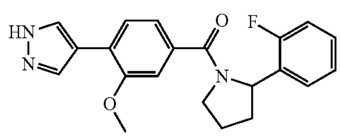 [SMILES: COc1cc(C(=O)N2CCCC2c2ccccc2F)ccc1-c1cn[nH]c1] | 4-{4-[2-(2-fluorophenyl)pyrrolidine-1-carbonyl]-2-methoxyphenyl}-1H-pyrazole | 366.2 | E: 1.39 F: 1.40 | (500 MHz, DMSO-d6) δ 8.17-7.99 (m, 2H), 7.78-7.47 (m, 1H), 7.44-7.24 (m, 2H), 7.24-6.67 (m, 4H), 5.44-5.04 (m, 1H), 3.99-3.68 (m, 4H), 3.64-3.39 (m, 1H), 2.45-2.21 (m, 1H), 2.02-1.63 (m, 3H) |
| 21 | 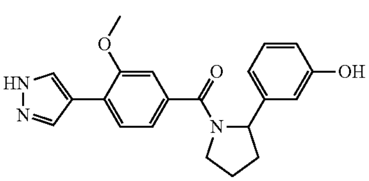 [SMILES: COc1cc(C(=O)N2CCCC2c2cccc(O)c2)ccc1-c1cn[nH]c1] | 3-{1-[3-methoxy-4-(1H-pyrazol-4-yl)benzoyl]pyrrolidin-2-yl}phenol | 364.3 | E: 1.22 F: 1.25 | (500 MHz, DMSO-d6) δ 8.22-7.97 (m, 2H), 7.77-7.47 (m, 1H), 7.26-7.05 (m, 2H), 6.94-6.48 (m, 4H), 5.18-4.81 (m, 1H), 3.93 (br. s., 3H), 3.82-3.52 (m, 2H), 2.40-2.15 (m, 1H), 1.90-1.63 (m, 3H) |
| 22 | 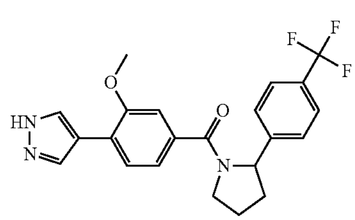 [SMILES: COc1cc(C(=O)N2CCCC2c2ccc(C(F)(F)F)cc2)ccc1-c1cn[nH]c1] | 4-(2-methoxy-4-{2-[4-(trifluoromethyl)phenyl]pyrrolidine-1-carbonyl}phenyl)-1H-pyrazole | 416.0 | E: 1.60 F: 1.78 | (500 MHz, DMSO-d6) δ 8.31-7.97 (m, 2H), 7.80-7.45 (m, 5H), 7.42-6.96 (m, 2H), 5.33-4.95 (m, 1H), 4.02-3.58 (m, 2H), 3.52 (s, 3H), 2.47-2.25 (m, 1H), 2.01-1.66 (m, 3H) |
| 23 | 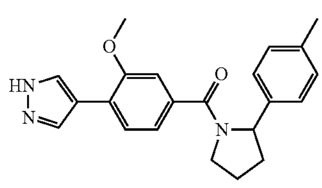 [SMILES: COc1cc(C(=O)N2CCCC2c2ccc(C)cc2)ccc1-c1cn[nH]c1] | 4-{2-methoxy-4-[2-(4-methylphenyl)pyrrolidine-1-carbonyl]phenyl}-1H-pyrazole | 362.4 | E: 1.71 F: 1.68 | (500 MHz, DMSO-d6) δ 8.05 (br. s., 2H), 7.77-7.41 (m, 1H), 7.26-7.17 (m, 2H), 7.13 (br. s., 2H), 7.05-6.68 (m, 2H), 5.22-4.83 (m, 1H), 3.98-3.62 (m, 2H), 3.59 (s, 3H), 2.34 (br. s., 1H), 2.28 (br. s., 3H), 1.99-1.67 (m, 3H) |
| 24 | 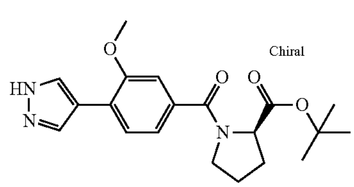 [SMILES: COc1cc(C(=O)N2CCC[C@@H]2C(=O)OC(C)(C)C)ccc1-c1cn[nH]c1] | tert-butyl (2R)-1-[3-methoxy-4-(1H-pyrazol-4-yl)benzoyl]pyrrolidine-2-carboxylate | 372.0 | E: 1.47 F: 1.52 | (400 MHz, CD3OD) δ 8.30-8.17 (m, 2H), 7.76-7.63 (m, 1H), 7.29-7.01 (m, 2H), 4.54-4.42 (m, 1H), 3.98 (s, 3H), 3.79-3.55 (m, 2H), 2.36 (dq, J = 8.4, 5.9 Hz, 1H), 2.09-1.83 (m, 3H), 1.51 and 1.25 (singlets, 9H) |

TABLE 1-continued

| Ex. No. | Structure | Name | LCMS (M + H)+ | HPLC Method, RT (min.) | 1H NMR (ppm) |
|---|---|---|---|---|---|
| 25 | 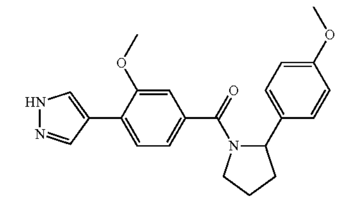 [SMILES: COc1ccc(C2CCCN2C(=O)c2ccc(-c3cn[nH]c3)c(OC)c2)cc1] | 4-{2-methoxy-4-[2-(4-methoxyphenyl)pyrrolidine-1-carbonyl]phenyl}-1H-pyrazole | 378.3 | E: 1.40 F: 1.41 | (500 MHz, DMSO-d6) δ 8.07 (br. s., 2H), 7.78-7.44 (m, 1H), 7.34-7.15 (m, 2H), 7.06 (br. s., 1H), 6.95-6.69 (m, 3H), 5.22-4.83 (m, 1H), 3.98-3.64 (m, 5H), 3.62-3.30 (m, 3H), 2.43-2.13 (m, 1H), 1.99-1.65 (m, 3H) |
| 26 | 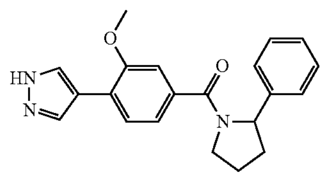 [SMILES: COc1cc(C(=O)N2CCCC2c2ccccc2)ccc1-c1cn[nH]c1] | 4-[2-methoxy-4-(2-phenyl-pyrrolidine-1-carbonyl)phenyl]-1H-pyrazole | 348.0 | E: 1.47 F: 1.49 | (500 MHz, DMSO-d6) δ 8.13 (br. s., 2H), 7.87-7.53 (m, 1H), 7.48-7.10 (m, 6H), 6.98-6.65 (m, 1H), 5.32-4.89 (m, 1H), 4.17-3.59 (m, 5H), 2.51-2.29 (m, 1H), 2.15-1.70 (m, 3H). |
| 27 | 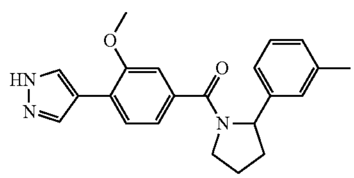 [SMILES: COc1cc(C(=O)N2CCCC2c2cccc(C)c2)ccc1-c1cn[nH]c1] | 4-{2-methoxy-4-[2-(3-methyl-phenyl)pyrrolidine-1-carbonyl]phenyl}-1H-pyrazole | 362.2 | E: 1.57 F: 1.61 | (500 MHz, DMSO-d6) δ 8.17-7.93 (m, 2H), 7.75-7.41 (m, 1H), 7.24-7.13 (m, 2H), 7.11 (br. s., 1H), 7.01 (br. s., 1H), 6.94-6.61 (m, 2H), 5.19-4.78 (m, 1H), 3.95-3.59 (m, 5H), 2.42-2.15 (m, 4H), 1.77 (br. s., 3H) |
| 28 | 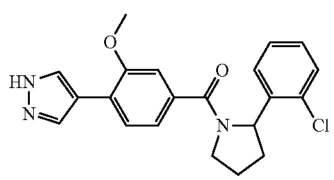 [SMILES: COc1cc(C(=O)N2CCCC2c2ccccc2Cl)ccc1-c1cn[nH]c1] | 4-{4-[2-(2-chlorophenyl)pyrrolidine-1-carbonyl]-2-methoxyphenyl}-1H-pyrazole | 382.2 | E: 1.57 F: 1.64 | (500 MHz, DMSO-d6) δ 8.24-8.01 (m, 2H), 7.82-7.53 (m, 1H), 7.51-6.66 (m, 6H), 5.52-5.15 (m, 1H), 4.06-3.62 (m, 5H), 2.54-2.30 (m, 1H), 2.07-1.63 (m, 3H) |
| 29 | 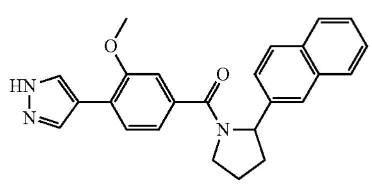 [SMILES: COc1cc(C(=O)N2CCCC2c2ccc3ccccc3c2)ccc1-c1cn[nH]c1] | 4-{2-methoxy-4-[2-(naphthalen-2-yl)pyrrolidine-1-carbonyl]phenyl}-1H-pyrazole | 398.2 | E: 1.66 F: 1.71 | (500 MHz, DMSO-d6) δ 8.11 (br. s., 1H), 7.98-7.80 (m, 4H), 7.75-7.60 (m, 1H), 7.58-7.37 (m, 3H), 7.33-6.70 (m, 3H), 5.38-5.05 (m, 1H), 4.04-3.21 (m, 5H), 2.46-2.26 (m, 1H), 2.02-1.70 (m, 3H) |
| 30 | 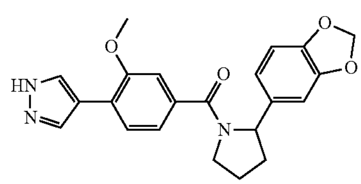 [SMILES: COc1cc(C(=O)N2CCCC2c2ccc3c(c2)OCO3)ccc1-c1cn[nH]c1] | 4-{4-[2-(2H-1,3-benzodioxol-5-yl)pyrrolidine-1-carbonyl]-2-methoxyphenyl}-1H-pyrazole | 392.2 | E: 1.36 F: 1.44 | (500 MHz, DMSO-d6) δ 8.08 (br. s., 2H), 7.74-7.45 (m, 1H), 7.19 (br. s., 1H), 7.00-6.50 (m, 4H), 5.97 (s, 2H), 5.18-4.77 (m, 1H), 4.03-3.29 (m, 5H), 2.40-2.11 (m, 1H), 1.94-1.63 (m, 3H) |

Example 31: 4-{4-[(2R)-2-(3-Methanesulfonylphenyl)pyrrolidine-1-carbonyl]-2-methoxyphenyl}-1H-pyrazole Example 31A: (R)-tert-Butyl 2-(3-(methylsulfonyl)phenyl)pyrrolidine-1-carboxylate

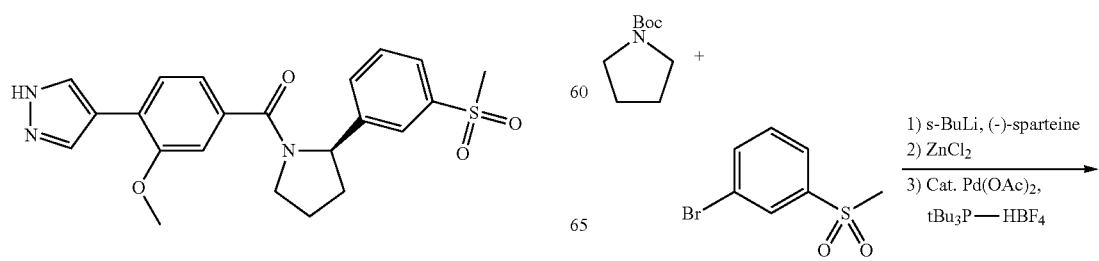

-continued

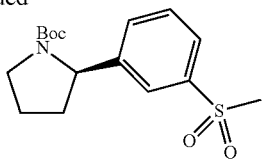

To a solution of tert-butyl pyrrolidine-1-carboxylate (1 mL, 5.71 mmol) and (−)-sparteine (1.310 mL, 5.70 mmol) in MTBE (12 mL) at −78° C. was added sec-BuLi (1.4 M in cyclohexane, 4.07 mL, 5.7 mmol) dropwise. The resulting solution was aged for 3 h at −78° C. A solution of $ZnCl_2$ (1 M in $Et_2O$, 3.4 mL, 3.40 mmol) was added to the reaction dropwise. The resulting light suspension was aged at −78° C. for 30 min, and then was warmed to 20° C. The resulting homogeneous solution was stirred for 30 min at 20° C., and then was added 1-bromo-3-(methylsulfonyl)benzene (1.117 g, 4.75 mmol), followed by the additions of $Pd(OAc)_2$ (0.053 g, 0.238 mmol) and tri-tert-butylphosphonium tetrafluoroborate (0.083 g, 0.285 mmol). The mixture was stirred overnight in a water bath at 20° C. To facilitate the filtration, 0.35 mL of $NH_4OH$ was added, and the mixture was aged for 1 h. The resulting slurry was filtered through a pad of CELITE®, and was washed with 60 mL MTBE. The filtrate was washed with 50 mL of 1 M HCl, and then twice with 50 mL of water. The organic layer was dried over $Na_2SO_4$, filtered and concentrated. The crude product was purified by normal phase chromatography to provide Example 31A (0.95 g, 61.5%) as a white crystalline solid. LC-MS(ESI) m/z: 348.0[M+Na]$^+$; $^1$H NMR (400 MHz, $CDCl_3$) δ 7.90-7.68 (m, 2H), 7.57-7.40 (m, 2H), 5.16-4.68 (m, 1H), 3.75-3.43 (m, 2H), 3.01 (s, 3H), 2.36 (br. s., 1H), 1.99-1.73 (m, 3H), 1.44 (br. s., 4H), 1.26-1.07 (m, 5H).

Example 31

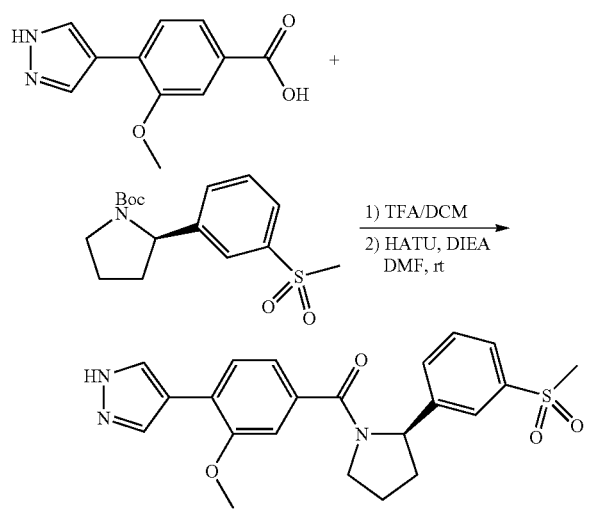

To a solution of 31A (35 mg, 0.108 mmol) in DCM (1 mL) was added TFA (0.5 mL, 6.49 mmol) at rt. The reaction was stirred at rt for 1 h. The solvent was removed. To the residue were added Intermediate 1 (23.47 mg, 0.108 mmol), DIEA (0.094 mL, 0.538 mmol) and HATU (45.0 mg, 0.118 mmol) at rt. The reaction was stirred under argon at rt for 1 h. Reverse phase purification provided Example 31 (26.8 mg, 57.4%). LC-MS(ESI) m/z: 426.15[M+H]$^+$; $^1$H NMR (500 MHz, DMSO-$d_6$) δ 8.31-7.98 (m, 2H), 7.91-7.01 (m, 7H), 5.34-5.04 (m, 1H), 4.01-3.44 (m, 5H), 3.30-3.01 (m, 3H), 2.49-2.28 (m, 1H), 2.04-1.66 (m, 3H). Analytical HPLC RT=1.18 min (Method E), 1.22 min (Method F).

Example 32: Methyl 3-[(2R)-1-[3-methoxy-4-(1H-pyrazol-4-yl)benzoyl]pyrrolidin-2-yl]benzoate

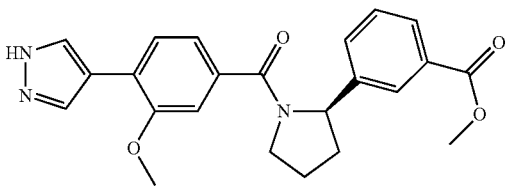 [SMILES: COC(=O)c1cccc([C@H]2CCCN2C(=O)c2ccc(-c3cn[nH]c3)c(OC)c2)c1]

Example 32 was prepared by following a similar procedure as described in Example 31 by replacing 1-bromo-3-(methylsulfonyl)benzene with methyl 3-bromobenzoate in Example 31A. LC-MS(ESI) m/z: 406.0[M+H]$^+$; $^1$H NMR (400 MHz, $CD_3OD$) δ 8.30-8.08 (m, 2H), 8.07-7.72 (m, 2H), 7.69-7.58 (m, 1H), 7.57-7.46 (m, 1H), 7.45-7.36 (m, 1H), 7.34-7.23 (m, 1H), 6.93-6.58 (m, 1H), 5.44-5.01 (m, 1H), 4.09-3.52 (m, 8H), 2.62-2.39 (m, 1H), 2.12-1.89 (m, 3H). Analytical HPLC RT=1.38 min (Method E), 1.42 min (Method F).

Example 33: 3-[(2R)-1-[3-Methoxy-4-(1H-pyrazol-4-yl)benzoyl]pyrrolidin-2-yl]benzoic acid

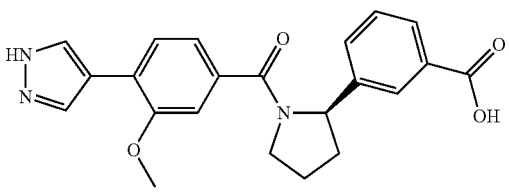 [SMILES: COc1cc(C(=O)N2CCC[C@@H]2c2cccc(C(=O)O)c2)ccc1-c1cn[nH]c1]

To a solution of Example 32 (95 mg, 0.234 mmol) in THF (2 mL) were added water (0.5 ml) and LiOH (5.61 mg, 0.234 mmol) at rt. The reaction was stirred under argon at rt overnight. The solvent was removed. The crude product was purified by reverse phase chromatography to afford Example 33 as a white solid (59 mg, 64.3%). LC-MS(ESI) m/z: 391[M+H]$^+$; $^1$H NMR (400 MHz, DMSO-$d_6$) δ 8.16-7.95 (m, 2H), 7.93-7.60 (m, 3H), 7.56-7.33 (m, 2H), 7.22 (br. s., 1H), 6.85-6.61 (m, 1H), 5.27-5.00 (m, 1H), 3.98-3.41 (m, 5H), 2.47-2.26 (m, 1H), 2.03-1.69 (m, 3H). Analytical HPLC RT=5.90 min (Method A), 5.57 min (Method B).

Example 34 (Enant.): 4-{4-[(2R)-2-(3-Methanesulfonylphenyl)pyrrolidine-1-carbonyl]-2-methoxyphenyl}-1H-pyrazole

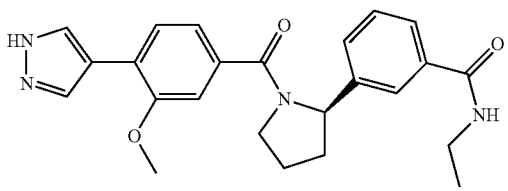

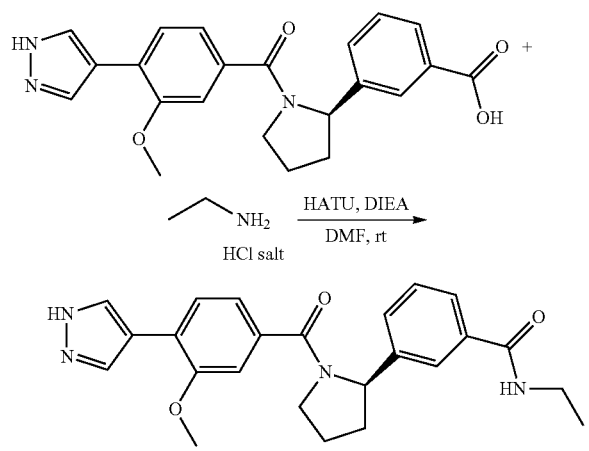

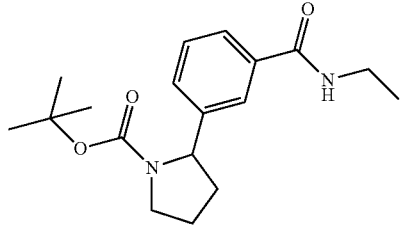

To a solution of 3-(1-(tert-butoxycarbonyl)pyrrolidin-2-yl)benzoic acid (23 mg, 0.079 mmol) in CHCl₃ (1 mL) were added ethyl amine HCl salt (3.56 mg, 0.079 mmol), DIEA (0.014 mL, 0.079 mmol) and HATU (30.0 mg, 0.079 mmol) at rt. The reaction was stirred under argon at rt for 2 h. The crude product was purified by normal phase chromatography to give a white solid (22 mg, 88%). LC-MS(ESI) m/z: 263.0 [M-55]⁺; ¹H NMR (400 MHz, CDCl₃) δ 7.58 (s, 2H), 7.41-7.32 (m, 1H), 7.32-7.27 (m, 1H), 6.08 (br. s., 1H), 5.14-4.65 (m, 1H), 3.73-3.42 (m, 4H), 2.34 (br. s., 1H), 1.97-1.76 (m, 3H), 1.45 (br. s., 3H), 1.25 (t, J=7.3 Hz, 4H), 1.18 (br. s., 5H).

To a solution of Example 33 (18 mg, 0.046 mmol) in DMF (1 mL) were added ethylamine HCl salt (7.50 mg, 0.092 mmol), DIEA (0.080 mL, 0.460 mmol) and HATU (20.98 mg, 0.055 mmol) at rt. The reaction was stirred under argon at rt for 2 h. The crude product was purified by reverse phase chromatography to afford Example 34 as a white solid (15.8 mg, 82%). LC-MS(ESI) m/z: 419.0[M+H]⁺; ¹H NMR (400 MHz, CD₃OD) δ 8.23 (s, 1H), 8.11 (s, 1H), 7.85 (s, 1H), 7.73-7.64 (m, 1H), 7.61-7.44 (m, 2H), 7.44-7.25 (m, 2H), 6.86-6.79 (m, 1H), 6.69 (s, 1H), 5.37-5.03 (m, 1H), 4.08-3.51 (m, 5H), 3.49-3.36 (m, 2H), 2.64-2.34 (m, 1H), 2.12-1.90 (m, 3H), 1.35-1.11 (m, 3H). Analytical HPLC RT=5.74 min (Method A), 5.41 min (Method B).

Example 35: N-Ethyl-3-(1-(3-methoxy-4-(1H-pyrazol-4-yl)benzoyl)pyrrolidin-2-yl)benzamide Example 35

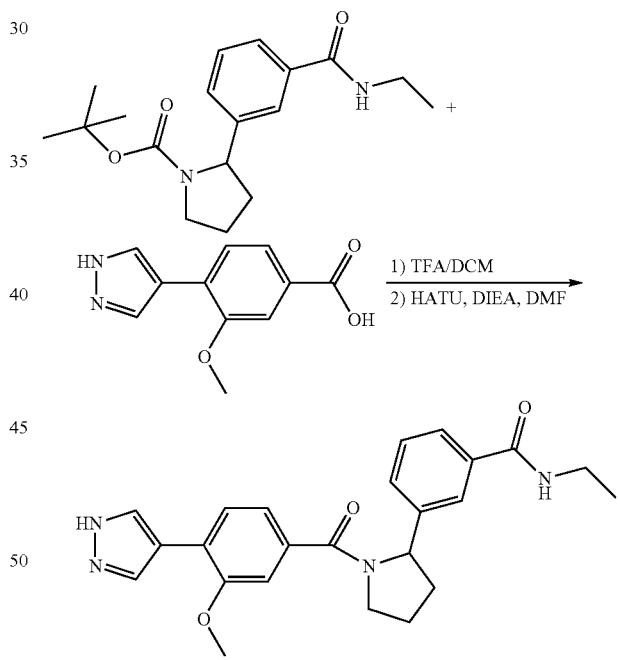

To a solution of Example 35A (22 mg, 0.069 mmol) in DCM (1 mL) was added TFA (0.5 mL, 6.49 mmol) at rt. The reaction was stirred at rt for 1 h. The solvent was removed, and the residue was dried in vacuo. To the intermediate were added DMF (1 mL), and then added Intermediate 1 (15.08 mg, 0.069 mmol), DIEA (0.060 mL, 0.345 mmol) and HATU (31.5 mg, 0.083 mmol) at rt. The reaction was stirred under argon at rt for 1 h. Purification by reverse phase chromatography afforded Example 35 (19 mg, 64%). LC-MS(ESI) m/z: 419.2[M+H]⁺; ¹H NMR (500 MHz, DMSO-d₆) δ 8.48 (br. s., 1H), 8.24-7.98 (m, 2H), 7.83-7.26 (m, 5H), 7.22 (br. s., 1H), 6.96-6.53 (m, 1H), 5.28-4.92 (m, 1H),

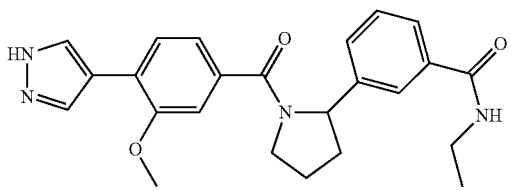 [SMILES: CCNC(=O)c1cccc(C2CCCN2C(=O)c2ccc(-c3cn[nH]c3)c(OC)c2)c1]

Example 35A: tert-Butyl 2-(3-(ethylcarbamoyl)phenyl)pyrrolidine-1-carboxylate

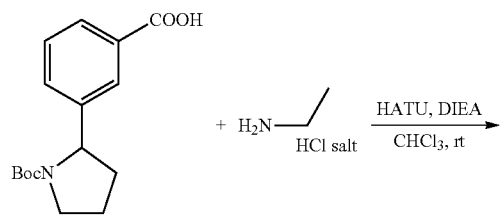

4.02-3.84 (m, 3H), 3.82-3.54 (m, 1H), 3.46-3.21 (m, 2H), 2.47-2.22 (m, 1H), 2.02-1.69 (m, 4H), 1.13 (br. s., 3H). Analytical HPLC RT=1.18 min (Method E), 1.21 min (Method F).

The following Examples in Table 2 were prepared by using the similar procedure as described in Example 34 and Example 35.

TABLE 2

| Ex. No. | Structure | Name | LCMS (M + H)+ | HPLC Method, RT (min.) | 1H NMR (ppm) |
|---|---|---|---|---|---|
| 36 (Rac) | 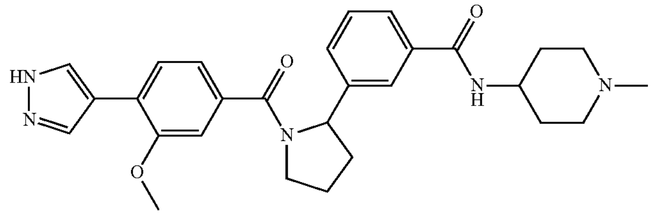 [SMILES: COc1cc(C(=O)N2CCCC2c2cccc(C(=O)NC3CCN(C)CC3)c2)ccc1-c1cn[nH]c1] | 3-{1-[3-methoxy-4-(1H-pyrazol-4-yl)benzoyl]pyrrolidin-2-yl}-N-(1-methylpiperidin-4-yl)benzamide | 488.2 | E: 0.94 F: 0.93 | (500 MHz, DMSO-d6) δ 8.34-8.19 (m, 1H), 8.16-7.96 (m, 2H), 7.85-6.60 (m, 7H), 5.31-4.86 (m, 1H), 4.00-3.53 (m, 3H), 2.86-2.73 (m, 2H), 2.46-2.24 (m, 1H), 2.18 (br. s., 3H), 1.98-1.90 (m, 6H), 1.84-1.69 (m, 4H), 1.61 (d, J = 10.8 Hz, 2H), 1.20-1.19 (m, 1H) |
| 37 (Enant. 1) | 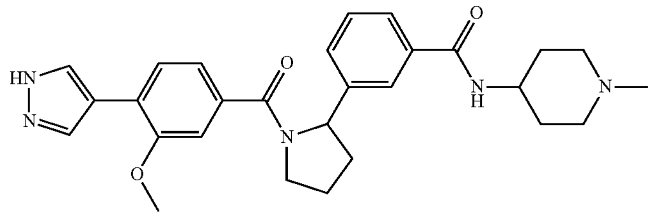 [SMILES: COc1cc(C(=O)N2CCCC2c2cccc(C(=O)NC3CCN(C)CC3)c2)ccc1-c1cn[nH]c1] | 3-{1-[3-methoxy-4-(1H-pyrazol-4-yl)benzoyl]pyrrolidin-2-yl}-N-(1-methylpiperidin-4-yl)benzamide | 488.1 | A: 6.69 B: 7.13 | (400 MHz, CD3OD) δ 8.07-7.79 (m, 2H), 7.68-7.47 (m, 2H), 7.45-7.13 (m, 4H), 6.94-6.50 (m, 1H), 5.37-4.76 (m, 1H), 3.93 (br. s., 4H), 3.86-3.65 (m, 2H), 3.49-3.37 (m, 1H), 3.21-3.04 (m, 1H), 2.84 (d, J = 11.2 Hz, 1H), 2.44 (d, J = 5.3 Hz, 1H), 2.27 (s, 3H), 2.11 (q, J = 11.8 Hz, 2H), 2.03-1.78 (m, 5H), 1.65-1.41 (m, 1H) |
| 38 (Enant. 2) | 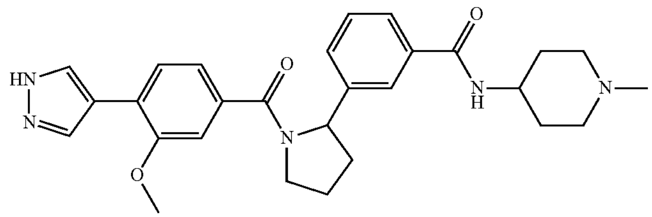 [SMILES: COc1cc(C(=O)N2CCCC2c2cccc(C(=O)NC3CCN(C)CC3)c2)ccc1-c1cn[nH]c1] | 3-{1-[3-methoxy-4-(1H-pyrazol-4-yl)benzoyl]pyrrolidin-2-yl}-N-(1-methylpiperidin-4-yl)benzamide | 488.1 | A: 6.48 B: 7.05 | (400 MHz, CDCl3) δ 8.17-7.93 (m, 2H), 7.78-7.56 (m, 2H), 7.54-7.27 (m, 4H), 7.05-6.61 (m, 1H), 5.46-4.91 (m, 1H), 4.11-3.82 (m, 5H), 3.53-3.35 (m, 3H), 3.31-3.11 (m, 1H), 2.93 (d, J = 10.6 Hz, 1H), 2.55 (br. s., 1H), 2.37 (s, 3H), 2.28-2.15 (m, 1H), 2.14-1.87 (m, 5H), 1.75-1.54 (m, 1H) |
| 39 | 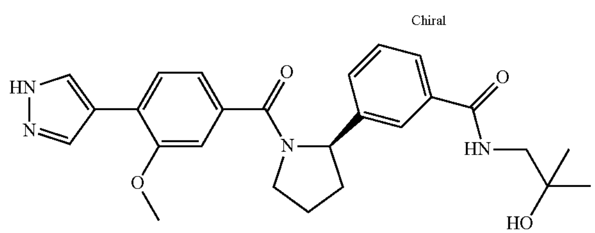 [SMILES: COc1cc(C(=O)N2CCC[C@@H]2c2cccc(C(=O)NCC(C)(C)O)c2)ccc1-c1cn[nH]c1] | N-(2-hydroxy-2-methylpropyl)-3-[(2R)-1-[3-methoxy-4-(1H-pyrazol-4-yl)benzoyl]pyrrolidin-2-yl]benzamide | 463.0 | A: 5.16 B: 4.88 | (400 MHz, CD3OD) δ 8.25 (s, 1H), 8.13 (s, 1H), 7.92-7.69 (m, 2H), 7.64-7.46 (m, 2H), 7.46-7.25 (m, 2H), 6.99-6.67 (m, 1H), 5.37-5.04 (m, 1H), 4.10-3.51 (m, 5H), 3.44 (s, 2H), 2.65-2.38 (m, 1H), 2.15-1.90 (m, 3H), 1.27, 1.21 (s, 6H) |

TABLE 2-continued

| Ex. No. | Structure | Name | LCMS (M + H)+ | HPLC Method, RT (min.) | 1H NMR (ppm) |
|---|---|---|---|---|---|
| 40 | 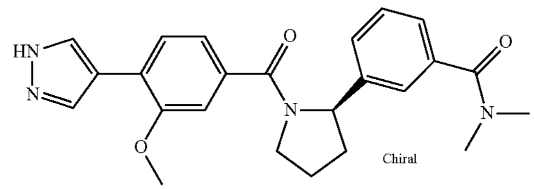 [SMILES: COc1cc(C(=O)N2CCC[C@@H]2c2cccc(C(=O)N(C)C)c2)ccc1-c1cn[nH]c1] | 3-[(2R)-1-[3-methoxy-4-(1H-pyrazol-4-yl)benzoyl]pyrrolidin-2-yl]-N,N-dimethylbenzamide | 419.2 | E: 1.18 F: 1.22 | (500 MHz, DMSO-d6) δ 8.20-7.95 (m, 2H), 7.75-7.45 (m, 1H), 7.44-7.24 (m, 3H), 7.20 (br. s., 2H), 7.10-6.62 (m, 1H), 5.27-4.93 (m, 1H), 3.98-3.44 (m, 5H), 3.04-2.68 (m, 6H), 2.45-2.22 (m, 1H), 2.01-1.65 (m, 3H) |
| 41 | 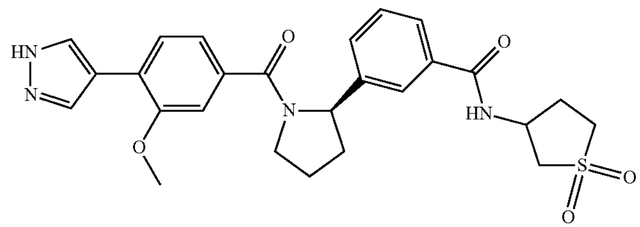 [SMILES: COc1cc(C(=O)N2CCC[C@@H]2c2cccc(C(=O)NC3CCS(=O)(=O)C3)c2)ccc1-c1cn[nH]c1] | N-(1,1-dioxo-1λ6-thiolan-3-yl)-3-[(2R)-1-[3-methoxy-4-(1H-pyrazol-4-yl)benzoyl]pyrrolidin-2-yl]benzamide | 509.1 | E: 1.21 F: 1.19 | (500 MHz, DMSO-d6) δ 8.86-8.59 (m, 1H), 8.19-7.96 (m, 2H), 7.84-7.29 (m, 5H), 7.25-6.63 (m, 2H), 5.27-4.94 (m, 1H), 4.69 (br. s., 1H), 3.98-3.70 (m, 5H), 3.64-3.27 (m, 2H), 3.18 (d, J = 13.1 Hz, 1H), 3.07 (d, J = 11.0 Hz, 1H), 2.46-2.12 (m, 3H), 2.00-1.65 (m, 3H) |
| 42 | 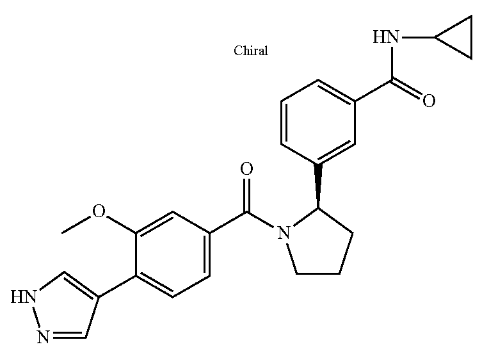 [SMILES: COc1cc(C(=O)N2CCC[C@@H]2c2cccc(C(=O)NC3CC3)c2)ccc1-c1cn[nH]c1] | N-cyclopropyl-3-[(2R)-1-[3-methoxy-4-(1H-pyrazol-4-yl)benzoyl]pyrrolidin-2-yl]benzamide | 431.2 | E: 1.12 F: 1.15 | (500 MHz, DMSO-d6) δ 8.48 (br. s., 1H), 8.21-7.97 (m, 2H), 7.82-7.57 (m, 3H), 7.54-7.34 (m, 2H), 7.32-6.65 (m, 2H), 5.28-4.91 (m, 1H), 4.04-3.37 (m, 5H), 2.85 (br. s., 1H), 2.46-2.22 (m, 1H), 1.78 (d, J = 6.7 Hz, 2H), 1.16 (d, J = 5.4 Hz, 1H), 0.71 (d, J = 6.4 Hz, 2H), 0.61-0.47 (m, 2H) |

Example 43: Methyl 3-[(2R)-4-(acetyloxy)-1-[3-methoxy-4-(1H-pyrazol-4-yl)benzoyl] pyrrolidin-2-yl]benzoate

Example 44: 3-[(2R)-4-Hydroxy-1-[3-methoxy-4-(1H-pyrazol-4-yl)benzoyl]pyrrolidin-2-yl]benzoic acid

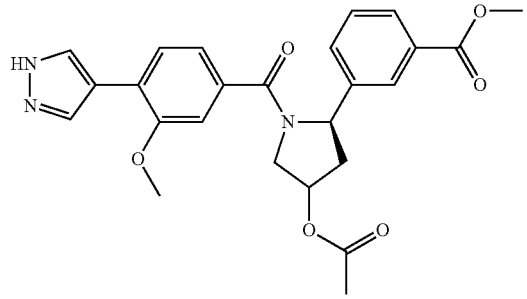

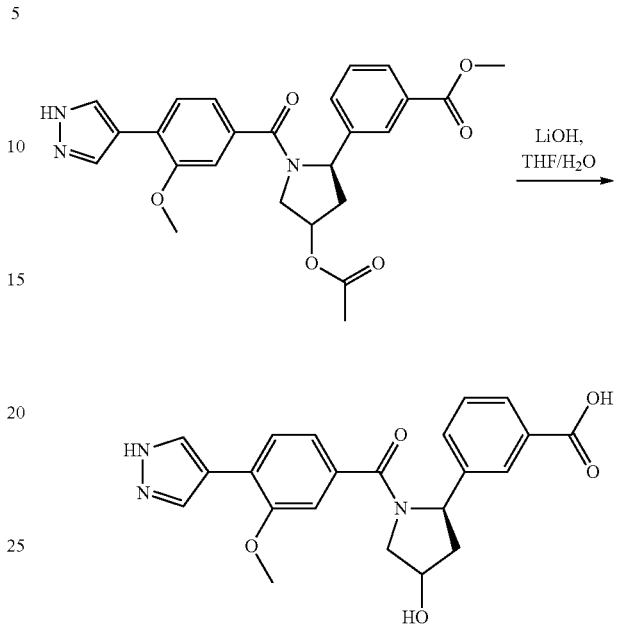

To a solution of Example 43 (100 mg, 0.216 mmol) in THF (2 mL) were added LiOH (25.8 mg, 1.079 mmol) and water (0.5 mL) at rt. The reaction was stirred under argon at rt for 3 h. The solvent was removed. The residue was dissolved in DMSO and neutralized with TFA. The crude product was purified by reverse phase chromatography to afford Example 44 as a white solid (75 mg, 84%). LC-MS (ESI) m/z: 408.2[M+H]$^+$; $^1$H NMR (400 MHz, DMSO-d$_6$) δ 8.14 (s, 2H), 8.02-7.78 (m, 2H), 7.77-7.61 (m, 2H), 7.47 (t, J=7.7 Hz, 1H), 7.33-7.14 (m, 2H), 5.44-4.98 (m, 1H), 4.31-4.03 (m, 1H), 3.94 (s, 3H), 3.87-3.42 (m, 2H), 2.96-2.60 (m, 0.4H), 2.45-2.15 (m, 1H), 1.93-1.81 (m, 0.6H); Analytical HPLC RT=6.81 min (Method A), 6.35 min (Method B).

Example 45: N-Ethyl-3-[(2R)-4-hydroxy-1-[3-methoxy-4-(1H-pyrazol-4-yl)benzoyl] pyrrolidin-2-yl]benzamide

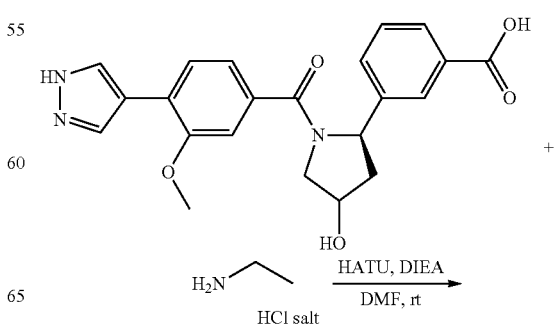

To a solution of Intermediate 3 (90 mg, 0.342 mmol) in DMF (5 mL) were added Intermediate 1 (74.6 mg, 0.342 mmol), DIEA (0.179 mL, 1.025 mmol) and HATU (136 mg, 0.359 mmol) at rt. The reaction was stirred under argon at rt for 2 h. The crude product was purified by reverse phase chromatography to afford Example 43 as a white solid (102 mg, 62.4%). LC-MS(ESI) m/z: 464.2[M+H]$^+$; $^1$H NMR (400 MHz, CD$_3$OD) δ 8.24 (s, 3H), 7.74 (dd, J=16.0, 7.8 Hz, 2H), 7.56-7.21 (m, 3H), 7.04-6.38 (m, 1H), 5.54-5.12 (m, 2H), 4.42-3.53 (m, 8H), 2.96-2.55 (m, 1H), 2.37-2.16 (m, 1H), 2.12-1.76 (m, 3H); Analytical HPLC RT=10.36 min (Method A), 9.68 min (Method B).

-continued

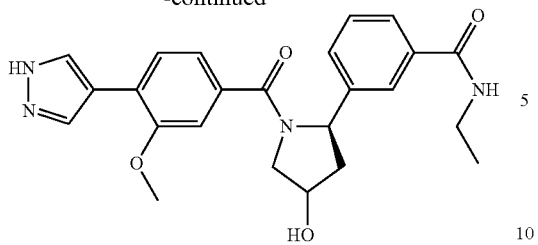

To a solution of Example 44 (20 mg, 0.049 mmol) in DMF (1.5 mL) were added ethylamine HCl salt (12.01 mg, 0.147 mmol), DIEA (0.043 mL, 0.245 mmol) and HATU (22.40 mg, 0.059 mmol) at rt. The reaction was stirred under argon at rt for 2 h. Purification by reverse phase chromatography afforded Example 45 (12.5 mg, 58.6%). LC-MS (ESI) m/z: 435.25 [M+H]$^+$; $^1$H NMR (500 MHz, DMSO-$d_6$) δ 8.56-8.31 (m, 1H), 8.29-7.98 (m, 2H), 7.81 (s, 1H), 7.69 (dd, J=14.5, 7.8 Hz, 2H), 7.53 (d, J=7.6 Hz, 1H), 7.40 (t, J=7.6 Hz, 1H), 7.29-7.14 (m, 2H), 5.33-4.95 (m, 2H), 4.32-3.45 (m, 5H), 3.41-3.15 (m, 2H), 2.40-2.25 (m, 1H), 1.92-1.62 (m, 1H), 1.20-1.00 (m, 3H); Analytical HPLC RT=0.95 min (Method E), 0.97 min (Method F).

The following Examples in Table 3 were prepared by using the similar procedure as described in Example 45.

TABLE 3

| Ex. No. | Structure | Name | LCMS (M + H)+ | HPLC Method, RT (min.) | 1H NMR (ppm) |
|---|---|---|---|---|---|
| 46 | 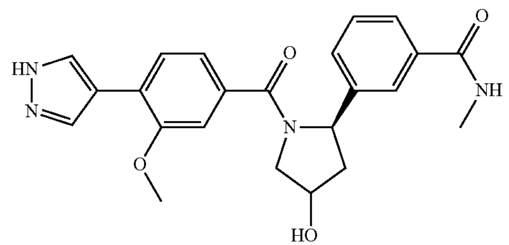 [SMILES: CNC(=O)c1cccc([C@H]2CC(O)CN2C(=O)c2ccc(-c3cn[nH]c3)c(OC)c2)c1] | 3-[(2R)-4-hydroxy-1-[3-methoxy-4-(1H-pyrazol-4-yl)benzoyl]pyrrolidin-2-yl]-N-methylbenzamide | 421.3 | E: 0.88 F: 0.90 | $^1$H NMR (500 MHz, DMSO-$d_6$) δ 8.50-8.20 (m, 2H), 8.13 (s, 1H), 7.90-7.75 (m, 1H), 7.75-7.61 (m, 2H), 7.53 (d, J = 7.6 Hz, 1H), 7.46-7.35 (m, 1H), 7.28-7.14 (m, 2H), 5.34-4.90 (m, 1H), 4.39-3.41 (m, 6H), 2.84-2.69 (m, 3H), 2.36 (br. s., 1H), 1.93-1.66 (m, 1H) |
| 47 | 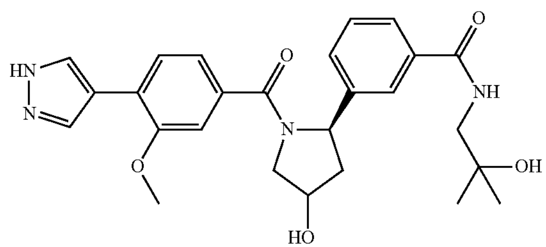 [SMILES: COc1cc(C(=O)N2CC(O)C[C@@H]2c2cccc(C(=O)NCC(C)(C)O)c2)ccc1-c1cn[nH]c1] | 3-[(2R)-4-hydroxy-1-[3-methoxy-4-(1H-pyrazol-4-yl)benzoyl]pyrrolidin-2-yl]-N-(2-hydroxy-2-methylpropyl)benzamide | 479.4 | E: 0.92 F: 0.93 | (500 MHz, DMSO-$d_6$) δ 8.34-7.95 (m, 3H), 7.87-7.65 (m, 2H), 7.54 (d, J = 7.6 Hz, 1H), 7.48-7.35 (m, 1H), 7.28-7.06 (m, 2H), 5.32-4.93 (m, 1), 4.39-3.60 (m, 5H), 3.53-3.09 (m, 3H), 2.35 (d, J = 7.0 Hz, 1H), 1.89-1.69 (m, 1H), 1.10 (br. s., 6H) |
| 48 | 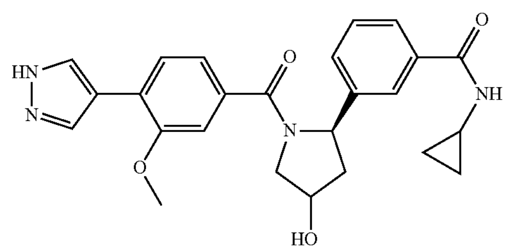 [SMILES: COc1cc(C(=O)N2CC(O)C[C@@H]2c2cccc(C(=O)NC3CC3)c2)ccc1-c1cn[nH]c1] | N-cyclopropyl-3-[(2R)-4-hydroxy-1-[3-methoxy-4-(1H-pyrazol-4-yl)benzoyl]pyrrolidin-2-yl]benzamide | 447.2 | E: 0.95 F: 0.98 | (500 MHz, DMSO-$d_6$) δ 8.46 (br. s., 1H), 8.11 (br. s., 2H), 7.78 (br. s., 1H), 7.71 (d, J = 7.9 Hz, 1H), 7.65 (d, J = 7.6 Hz, 1H), 7.53 (d, J = 7.0 Hz, 1H), 7.40 (d, J = 7.3 Hz, 1H), 7.21 (br. s., 2H), 5.22 (br. s., 1H), 4.36-3.82 (m, 4H), 3.75-3.29 (m, 2H), 2.83 (br. s., 1H), 2.35 (br. s., 1H), 1.85 (br. s., 1H), 1.27-1.22 (m, 1H), 0.70 (d, J = 5.8 Hz, 2H), 0.56 (br. s., 2H) |

TABLE 3-continued

| Ex. No. | Structure | Name | LCMS (M + H)+ | HPLC Method, RT (min.) | 1H NMR (ppm) |
|---|---|---|---|---|---|
| 49 | 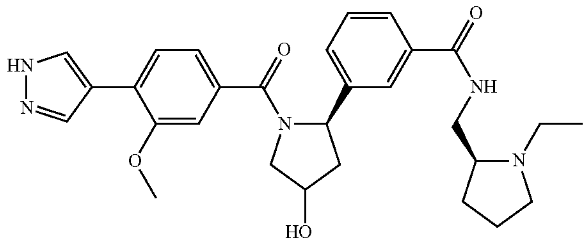 [SMILES: CCN1CCC[C@H]1CNC(=O)c1cccc([C@H]2CC(O)CN2C(=O)c2ccc(-c3cn[nH]c3)c(OC)c2)c1] | N-{[(2S)-1-ethylpyrrolidin-2-yl]methyl}-3-[(2R)-4-hydroxy-1-[3-methoxy-4-(1H-pyrazol-4-yl)benzoyl]pyrrolidin-2-yl]benzamide | 518.5 | E: 0.91 F: 0.89 | (500 MHz, DMSO-d6) δ 8.42 (br. s., 1H), 8.16-7.92 (m, 2H), 7.80 (br. s., 1H), 7.74-7.51 (m, 3H), 7.42 (d, J = 7.6 Hz, 1H), 7.22 (br. s., 2H), 5.23 (t, J = 8.1 Hz, 1H), 3.97-3.87 (m, 3H), 3.15-2.78 (m, 7H), 2.41-2.23 (m, 2H), 2.19-2.09 (m, 1H), 1.86-1.50 (m, 6H), 1.04 (t, J = 7.0 Hz, 3H) |
| 50 | 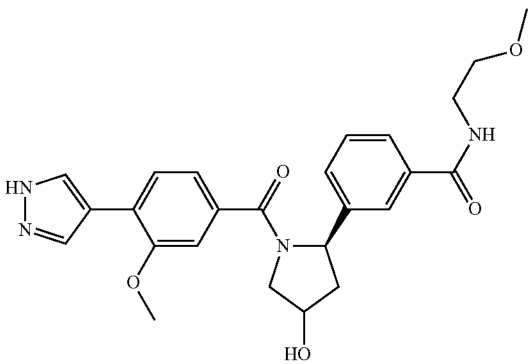 [SMILES: COCCNC(=O)c1cccc([C@H]2CC(O)CN2C(=O)c2ccc(-c3cn[nH]c3)c(OC)c2)c1] | 3-[(2R)-4-hydroxy-1-[3-methoxy-4-(1H-pyrazol-4-yl)benzoyl]pyrrolidin-2-yl]-N-(2-methoxyethyl)benzamide | 465.2 | E: 0.71 F: 0.74 | (500 MHz, DMSO-d6) δ 8.64-8.45 (m, 1H), 8.13 (br. s., 2H), 7.84 (s, 1H), 7.77-7.64 (m, 2H), 7.56 (d, J = 7.4 Hz, 1H), 7.48-7.36 (m, 1H), 7.29-7.15 (m, 2H), 5.39-5.03 (m, 1H), 4.44-3.77 (m, 7H), 3.76-3.35 (m, 2H), 3.27 (s, 3H), 2.45-2.28 (m, 1H), 1.93-1.81 (m, 1H) |
| 51 | 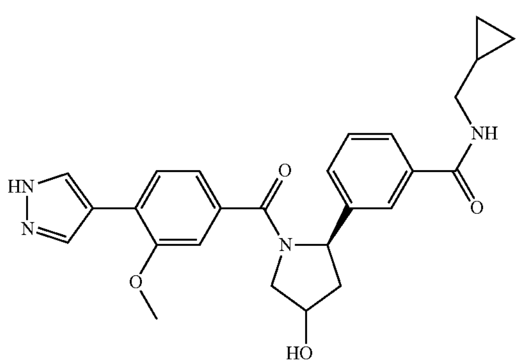 [SMILES: COc1cc(C(=O)N2CC(O)C[C@@H]2c2cccc(C(=O)NCC3CC3)c2)ccc1-c1cn[nH]c1] | N-(cyclopropylmethyl)-3-[(2R)-4-hydroxy-1-[3-methoxy-4-(1H-pyrazol-4-yl)benzoyl]pyrrolidin-2-yl]benzamide | 461.2 | E: 0.89 F: 0.91 | (500 MHz, DMSO-d6) δ 8.70-8.42 (m, 1H), 8.06 (br. s., 1H), 7.95-7.65 (m, 3H), 7.54 (d, J = 7.4 Hz, 1H), 7.46-7.37 (m, 1H), 7.27-7.07 (m, 2H), 5.36-4.96 (m, 2H), 4.42-3.87 (m, 4H), 3.54-3.37 (m, 2H), 3.15 (d, J = 5.0 Hz, 2H), 2.43-2.23 (m, 1H), 1.93-1.78 (m, 1H), 1.03 (br. s., 1H), 0.42 (d, J = 7.4 Hz, 2H), 0.23 (d, J = 4.4 Hz, 2H) |

TABLE 3-continued

| Ex. No. | Structure | Name | LCMS (M + H)+ | HPLC Method, RT (min.) | 1H NMR (ppm) |
|---|---|---|---|---|---|
| 52 | 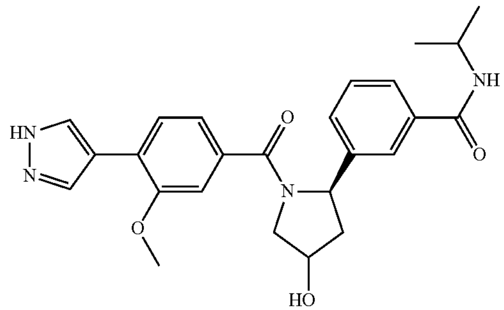 [SMILES: COc1cc(C(=O)N2CC(O)C[C@@H]2c2cccc(C(=O)NC(C)C)c2)ccc1-c1cn[nH]c1] | 3-[(2R)-4-hydroxy-1-[3-methoxy-4-(1H-pyrazol-4-yl)benzoyl]pyrrolidin-2-yl]-N-(propan-2-yl)benzamide | 449.2 | E: 0.84 F: 0.87 | (500 MHz, DMSO-d6) δ 8.24 (d, J = 7.4 Hz, 1H), 8.08 (br. s., 2H), 7.80 (br. s., 1H), 7.69 (dd, J = 13.6, 7.6 Hz, 2H), 7.54 (t, J = 7.9 Hz, 1H), 7.40 (t, J = 7.7 Hz, 1H), 7.20 (d, J = 5.7 Hz, 2H), 5.37-4.96 (m, 2H), 4.45-3.86 (m, 4H), 3.78-3.39 (m, 2H), 2.66-2.25 (m, 1H), 1.89-1.60 (m, 1H), 1.20-1.10 (m, 6H) |
| 53 | 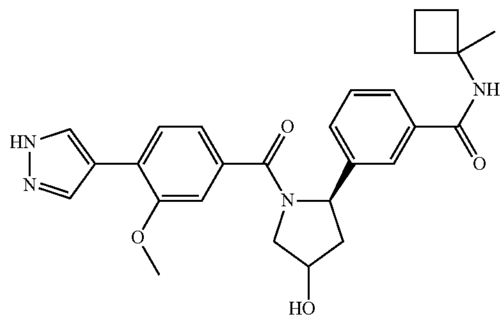 [SMILES: COc1cc(C(=O)N2CC(O)C[C@@H]2c2cccc(C(=O)NC3(C)CCC3)c2)ccc1-c1cn[nH]c1] | 3-[(2R)-4-hydroxy-1-[3-methoxy-4-(1H-pyrazol-4-yl)benzoyl]pyrrolidin-2-yl]-N-(1-methylcyclobutyl)benzamide | 475.3 | E: 1.07 F: 1.05 | (500 MHz, DMSO-d6) δ 8.39 (s, 1H), 8.12 (s, 2H), 7.80 (br. s., 1H), 7.74-7.48 (m, 3H), 7.38 (t, J = 7.6 Hz, 1H), 7.26-7.11 (m, 2H), 5.32-4.98 (m, 1H), 4.44-3.84 (m, 5H), 3.73-3.36 (m, 1H), 2.41-2.17 (m, 3H), 2.08-1.67 (m, 5H), 1.56-1.32 (m, 3H) |
| 54 | 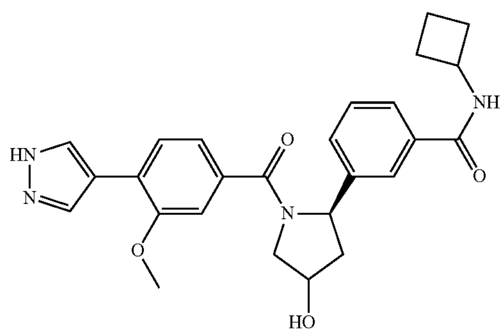 [SMILES: COc1cc(C(=O)N2CC(O)C[C@@H]2c2cccc(C(=O)NC3CCC3)c2)ccc1-c1cn[nH]c1] | N-cyclobutyl-3-[(2R)-4-hydroxy-1-[3-methoxy-4-(1H-pyrazol-4-yl)benzoyl]pyrrolidin-2-yl]benzamide | 461.3 | E: 0.96 F: 0.93 | (500 MHz, DMSO-d6) δ 8.71-8.42 (m, 1H), 8.33-7.95 (m, 2H), 7.80 (br. s., 1H), 7.70 (dd, J = 13.3, 7.9 Hz, 2H), 7.57-7.46 (m, 1H), 7.46-7.34 (m, 1H), 7.22 (br. s., 2H), 5.29-4.98 (m, 2H), 4.52-4.03 (m, 3H), 3.92 (s, 2H), 3.57-3.35 (m, 1H), 2.43-1.81 (m, 6H), 1.67 (d, J = 5.0 Hz, 2H) |

| Ex. No. | Structure | Name | LCMS (M + H)+ | HPLC Method, RT (min.) | 1H NMR (ppm) |
|---|---|---|---|---|---|
| 55 | 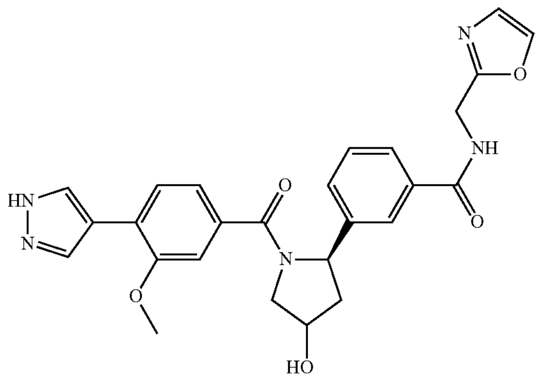 [SMILES: COc1cc(C(=O)N2CC(O)C[C@@H]2c2cccc(C(=O)NCc3ncco3)c2)ccc1-c1cn[nH]c1] | 3-[(2R)-4-hydroxy-1-[3-methoxy-4-(1H-pyrazol-4-yl)benzoyl]pyrrolidin-2-yl]-N-(1,3-oxazol-2-ylmethyl)benzamide | 488.2 | E: 0.96 F: 0.73 | (500 MHz, DMSO-$d_6$) δ 9.29-9.07 (m, 1H), 8.12 (br. s., 2H), 8.05-7.96 (m, 1H), 7.92-7.82 (m, 1H), 7.72 (dd, J = 15.3, 7.6 Hz, 2H), 7.58 (d, J = 7.4 Hz, 1H), 7.44 (t, J = 7.6 Hz, 1H), 7.30-7.05 (m, 3H), 5.30-5.03 (m, 1H), 4.69-4.48 (m, 2H), 4.40-4.19 (m, 1H), 4.08 (d, J = 8.8 Hz, 1H), 3.91 (s, 3H), 3.77-3.38 (m, 1H), 2.42-2.26 (m, 1H), 1.90-1.80 (m, 1H) |
| 56 | 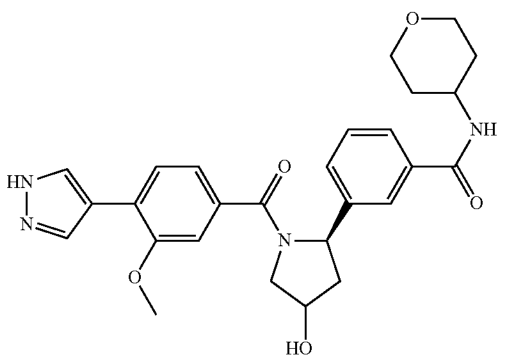 [SMILES: COc1cc(C(=O)N2CC(O)C[C@@H]2c2cccc(C(=O)NC3CCOCC3)c2)ccc1-c1cn[nH]c1] | 3-[(2R)-4-hydroxy-1-[3-methoxy-4-(1H-pyrazol-4-yl)benzoyl]pyrrolidin-2-yl]-N-(oxan-4-yl)benzamide | 491.3 | E: 0.79 F: 0.76 | (500 MHz, DMSO-$d_6$) δ 8.34 (d, J = 7.1 Hz, 1H), 8.13 (br. s., 2H), 7.82 (br. s., 1H), 7.71 (t, J = 7.9 Hz, 2H), 7.56 (d, J = 7.7 Hz, 1H), 7.48-7.35 (m, 1H), 7.22 (br. s., 2H), 5.32-5.10 (m, 1H), 4.44-4.18 (m, 1H), 4.15-3.81 (m, 6H), 3.76-3.03 (m, 3H), 2.43-2.25 (m, 1H), 1.96-1.82 (m, 3H), 1.76 (br. s, 2H), 1.60 (d, J = 10.1 Hz, 2H) |

TABLE 3-continued

| Ex. No. | Structure | Name | LCMS (M + H)+ | HPLC Method, RT (min.) | ¹H NMR (ppm) |
|---|---|---|---|---|---|
| 57 | 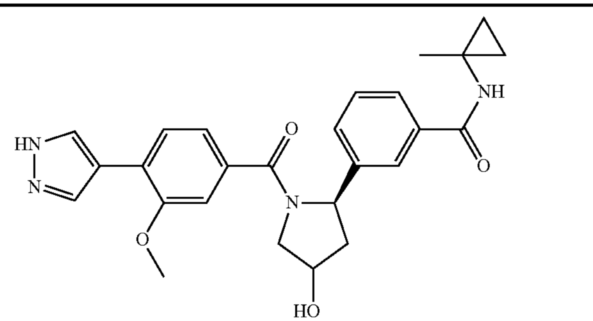 | 3-[(2R)-4-hydroxy-1-[3-methoxy-4-(1H-pyrazol-4-yl)benzoyl]pyrrolidin-2-yl]-N-(1-methylcyclopropyl)benzamide | 461.2 | E: 0.89 F: 0.86 | (500 MHz, DMSO-d₆) δ 8.68 (s, 1H), 8.13 (br. s., 2H), 7.86-7.77 (m, 1H), 7.72 (d, J = 7.4 Hz, 1H), 7.67 (d, J = 7.4 Hz, 1H), 7.53 (d, J = 7.4 Hz, 1H), 7.39 (t, J = 7.6 Hz, 1H), 7.26-7.15 (m, 2H), 5.30-5.10 (m, 1H), 4.42-4.19 (m, 1H), 4.09 (d, J = 8.8 Hz, 1H), 3.93 (s, 3H), 2.42-2.24 (m, 1H), 1.89-1.67 (m, 1H), 1.38 (s, 3H), 1.23 (d, J = 6.4 Hz, 2H), 0.74 (br. s., 2H), 0.62 (br. s., 2H) |
| 58 | 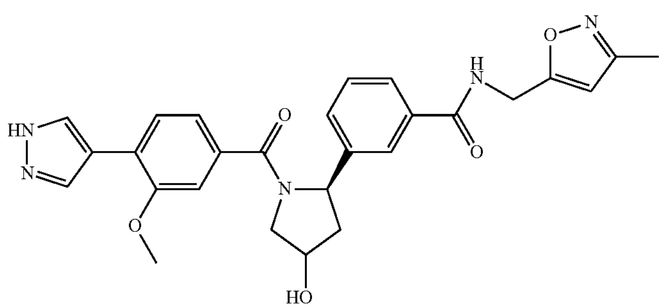 [SMILES: COc1cc(C(=O)N2CC(O)C[C@@H]2c2cccc(C(=O)NCc3cc(C)no3)c2)ccc1-c1cn[nH]c1] | 3-[(2R)-4-hydroxy-1-[3-methoxy-4-(1H-pyrazol-4-yl)benzoyl]pyrrolidin-2-yl]-N-[(3-methyl-1,2-oxazol-5-yl)methyl]benzamide | 502.2 | E: 1.00 F: 1.02 | (500 MHz, DMSO-d₆) δ 9.19 (br. s., 1H), 8.35-7.95 (m, 2H), 7.88 (br. s., 1H), 7.74 (t, J = 9.2 Hz, 2H), 7.60 (d, J = 7.3 Hz, 1H), 7.46 (t, J = 7.3 Hz, 1H), 7.33-7.10 (m, 2H), 6.32-6.07 (m, 1H), 5.33-5.21 (m, 1H), 5.19-5.00 (m, 1H), 4.68-4.44 (m, 2H), 4.39-3.72 (m, 4H), 3.56-3.41 (m, 1H), 2.45-2.30 (m, 1H), 2.19 (s, 3H), 1.95-1.81 (m, 1H) |
| 59 | 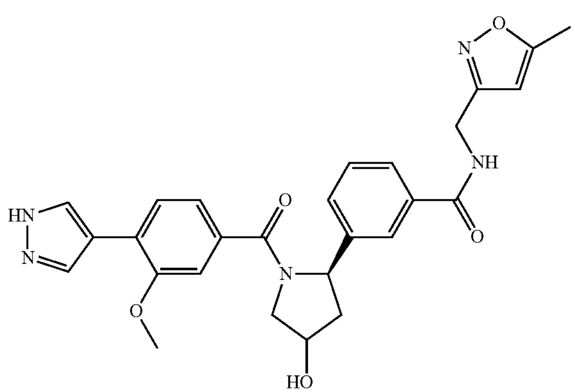 [SMILES: COc1cc(C(=O)N2CC(O)C[C@@H]2c2cccc(C(=O)NCc3cc(C)on3)c2)ccc1-c1cn[nH]c1] | 3-[(2R)-4-hydroxy-1-[3-methoxy-4-(1H-pyrazol-4-yl)benzoyl]pyrrolidin-2-yl]-N-[(5-methyl-1,2-oxazol-3-yl)methyl]benzamide | 502.1 | E: 0.90 F: 0.93 | (500 MHz, DMSO-d₆) δ 9.36-9.05 (m, 1H), 8.13 (s, 2H), 7.87 (s, 1H), 7.78-7.68 (m, 2H), 7.58 (d, J = 7.1 Hz, 1H), 7.49-7.37 (m, 2H), 7.28-7.07 (m, 2H), 6.15 (d, J = 4.4 Hz, 1H), 5.25 (t, J = 8.6 Hz, 1H), 4.58-4.32 (m, 3H), 4.31-3.46 (m, 3H), 2.55 (t, J = 5.6 Hz, 1H), 2.42-2.28 (m, 5H) |

TABLE 3-continued

| Ex. No. | Structure | Name | LCMS (M + H)+ | HPLC Method, RT (min.) | 1H NMR (ppm) |
|---|---|---|---|---|---|
| 60 | 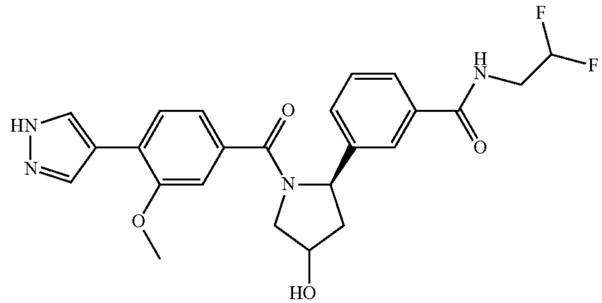 [SMILES: COc1cc(C(=O)N2CC(O)C[C@@H]2c2cccc(C(=O)NCC(F)F)c2)ccc1-c1cn[nH]c1] | N-(2,2-difluoroethyl)-3-[(2R)-4-hydroxy-1-[3-methoxy-4-(1H-pyrazol-4-yl)benzoyl]pyrrolidin-2-yl]benzamide | 471.2 | E: 0.80 F: 0.91 | (500 MHz, DMSO-d6) δ 9.00-8.73 (m, 1H), 8.11 (br. s., 2H), 7.86 (s, 1H), 7.72 (t, J = 8.4 Hz, 2H), 7.64-7.52 (m, 1H), 7.44 (t, J = 7.7 Hz, 1H), 7.30-7.10 (m, 2H), 6.35-5.93 (m, 1H), 5.37-5.02 (m, 1H), 4.43-4.21 (m, 1H), 4.13-3.35 (m, 8H), 2.42-2.23 (m, 1H), 1.96-1.79 (m, 1H) |
| 61 | 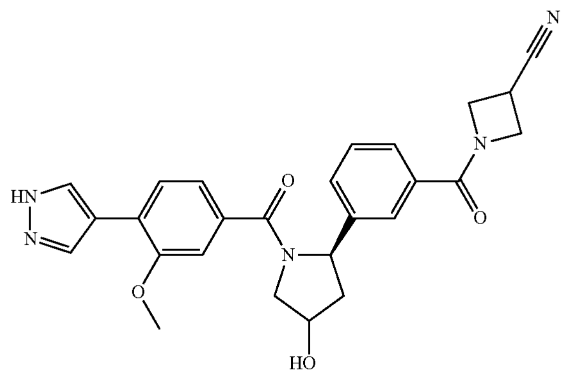 [SMILES: COc1cc(C(=O)N2CC(O)C[C@@H]2c2cccc(C(=O)N3CC(C#N)C3)c2)ccc1-c1cn[nH]c1] | 1-{3-[(2R)-4-hydroxy-1-[3-methoxy-4-(1H-pyrazol-4-yl)benzoyl]pyrrolidin-2-yl]benzoyl}azetidin-3-carbonitrile | 472.1 | E: 0.73 F: 0.76 | (500 MHz, DMSO-d6) δ 8.23-8.00 (m, 2H), 7.75-7.40 (m, 4H), 7.36-6.52 (m, 3H), 5.37-4.97 (m, 1H), 4.68-4.03 (m, 2H), 4.02-3.39 (m, 8H), 2.68-2.36 (m, 1H), 2.04-1.61 (m, 1H) |

TABLE 3-continued

| Ex. No. | Structure | Name | LCMS (M + H)+ | HPLC Method, RT (min.) | 1H NMR (ppm) |
|---|---|---|---|---|---|
| 62 | 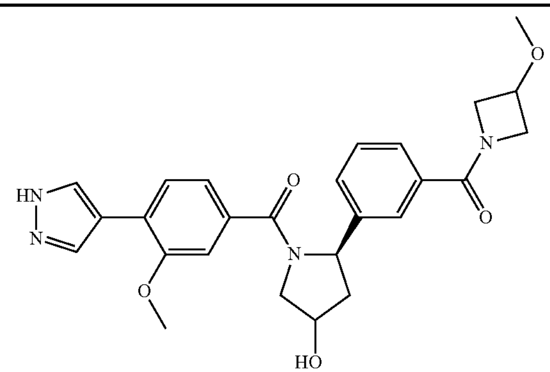 | (5R)-1-[3-methoxy-4-(1H-pyrazol-4-yl)benzoyl]-5-[3-(3-methoxyazetidine-1-carbonyl)phenyl]pyrrolidin-3-ol | 477.2 | E: 0.78 F: 0.79 | (500 MHz, DMSO-d6) δ 8.30 (br. s., 2H), 8.11 (s, 2H), 7.75-7.58 (m, 2H), 7.55-7.35 (m, 3H), 5.34-4.96 (m, 1H), 4.50-3.62 (m, 10H), 3.62-3.42 (m, 4H), 2.36 (br. s., 1H), 1.85-1.64 (m, 1H) |
| 63 | 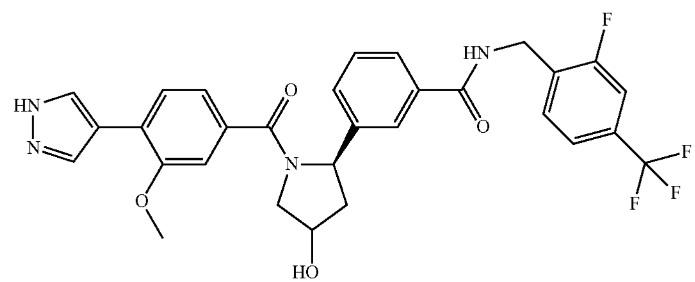 [SMILES: COc1cc(C(=O)N2CC(O)C[C@@H]2c2cccc(C(=O)NCc3ccc(C(F)(F)F)cc3F)c2)ccc1-c1cn[nH]c1] | N-[[2-fluoro-4-(trifluoromethyl)phenyl]methyl]-3-[(2R)-4-hydroxy-1-[3-methoxy-4-(1H-pyrazol-4-yl)benzoyl]pyrrolidin-2-yl]benzamide | 583.3 | E: 1.39 F: 1.52 | (500 MHz, DMSO-d6) δ 9.29-9.02 (m, 1H), 8.11 (br. s., 2H), 7.91-7.82 (m, 1H), 7.79-7.61 (m, 3H), 7.61-7.49 (m, 3H), 7.44 (t, J = 7.4 Hz, 1H), 7.30-7.11 (m, 2H), 5.37-4.90 (m, 1H), 4.69-4.44 (m, 2H), 4.36-3.36 (m, 6H), 2.63-2.29 (m, 1H), 1.93-1.64 (m, 1H) |
| 64 | 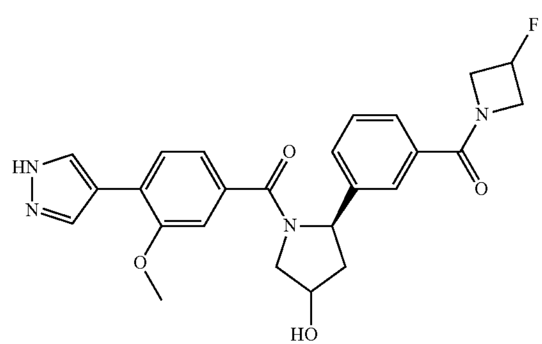 [SMILES: COc1cc(C(=O)N2CC(O)C[C@@H]2c2cccc(C(=O)N3CC(F)C3)c2)ccc1-c1cn[nH]c1] | (5R)-5-[3-(3-fluoroazetidine-1-carbonyl)phenyl]-1-[3-methoxy-4-(1H-pyrazol-4-yl)benzoyl]pyrrolidin-3-ol | 465.2 | E: 0.78 F: 0.86 | (500 MHz, DMSO-d6) δ 8.13 (br. s., 2H), 7.72 (d, J = 8.1 Hz, 1H), 7.68-7.59 (m, 1H), 7.56 (d, J = 6.7 Hz, 1H), 7.52-7.40 (m, 2H), 7.35-7.09 (m, 3H), 5.54-5.32 (m, 1H), 5.30-4.96 (m, 2H), 4.48-4.34 (m, 2H), 4.29 (br. s., 1H), 4.11 (br. s., 2H), 3.99-3.84 (m, 3H), 2.43-2.28 (m, 1H), 1.89-1.81 (m, 1H) |

TABLE 3-continued

| Ex. No. | Structure | Name | LCMS (M + H)+ | HPLC Method, RT (min.) | 1H NMR (ppm) |
|---|---|---|---|---|---|
| 65 | 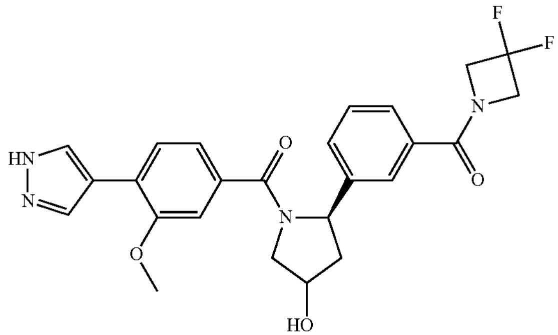 [SMILES: COc1cc(C(=O)N2CC(O)C[C@@H]2c2cccc(C(=O)N3CC(F)(F)C3)c2)ccc1-c1cn[nH]c1] | (5R)-5-[3-(3,3-difluoroazetidine-1-carbonyl)phenyl]-1-[3-methoxy-4-(1H-pyrazol-4-yl)benzoyl]pyrrolidin-3-ol | 483.2 | E: 0.89 F: 0.91 | (500 MHz, DMSO-d6) δ 8.34-7.98 (m, 2H), 7.78-7.64 (m, 2H), 7.59 (d, J = 6.7 Hz, 1H), 7.54 (d, J = 7.1 Hz, 1H), 7.49-7.27 (m, 2H), 7.26-7.15 (m, 2H), 5.33-5.01 (m, 2H), 4.59-4.23 (m, 4H), 3.98-3.68 (m, 3H), 3.44 (br. s., 1H), 2.67-2.30 (m, 1H), 1.87-1.66 (m, 1H) |
| 66 | 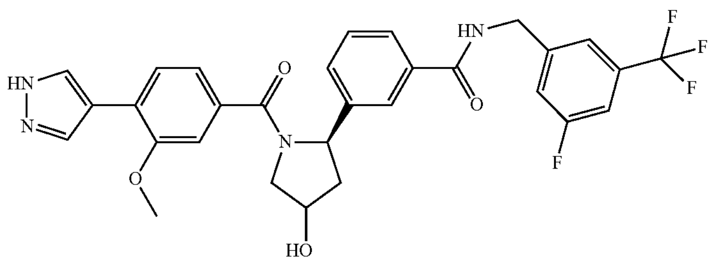 [SMILES: COc1cc(C(=O)N2CC(O)C[C@@H]2c2cccc(C(=O)NCc3cc(F)cc(C(F)(F)F)c3)c2)ccc1-c1cn[nH]c1] | N-[[3-fluoro-5-(trifluoromethyl)phenyl]methyl]-3-[(2R)-4-hydroxy-1-[3-methoxy-4-(1H-pyrazol-4-yl)benzoyl]pyrrolidin-2-yl]benzamide | 583.3 | E: 1.38 F: 1.41 | (500 MHz, DMSO-d6) δ 9.18 (br. s., 1H), 8.11 (s, 2H), 7.91-7.83 (m, 1H), 7.78-7.66 (m, 2H), 7.62-7.53 (m, 3H), 7.51-7.39 (m, 2H), 7.25-7.10 (m, 2H), 5.33-5.03 (m, 1H), 4.68-4.44 (m, 2H), 4.33-3.35 (m, 6H), 2.64-2.36 (m, 1H), 1.94-1.66 (m, 1H) |
| 67 | 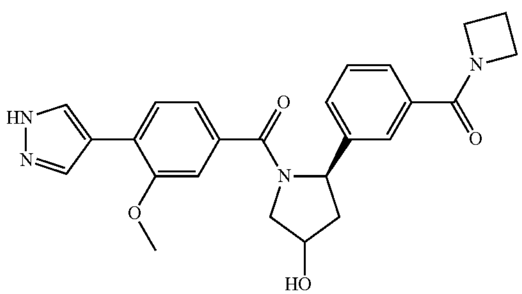 [SMILES: COc1cc(C(=O)N2CC(O)C[C@@H]2c2cccc(C(=O)N3CCC3)c2)ccc1-c1cn[nH]c1] | (5R)-5-[3-(azetidine-1-carbonyl)phenyl]-1-[3-methoxy-4-(1H-pyrazol-4-yl)benzoyl]pyrrolidin-3-ol | 447.5 | E: 0.97 F: 0.96 | (500 MHz, DMSO-d6) δ 8.10 (br. s., 2H), 7.70 (d, J = 7.9 Hz, 1H), 7.59 (s, 1H), 7.51 (d, J = 7.3 Hz, 1H), 7.48-7.34 (m, 2H), 7.26-7.13 (m, 2H), 5.32-5.11 (m, 1H), 4.28 (t, J = 14.5 Hz, 2H), 4.13-3.96 (m, 3H), 3.92 (s, 4H), 3.60-3.44 (m, 1H), 2.35 (d, J = 7.6 Hz, 1H), 2.27-2.17 (m, 2H), 1.85 (br. s., 1H) |

Example 68: 1-[3-Methoxy-4-(1H-pyrazol-4-yl)benzoyl]-2-phenylpiperazine

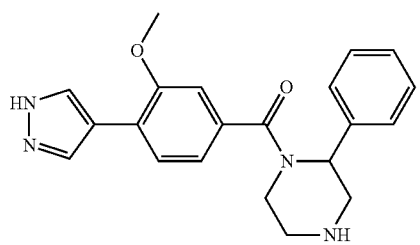 [SMILES: COc1cc(C(=O)N2CCNCC2c2ccccc2)ccc1-c1cn[nH]c1]

Example 68A: tert-Butyl 4-(3-methoxy-4-(1H-pyrazol-4-yl)benzoyl)-3-phenylpiperazine-1-carboxylate

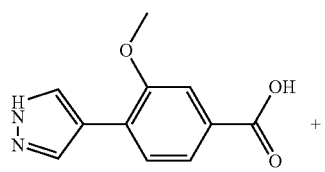

+

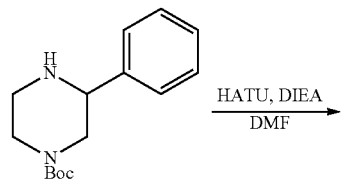

HATU, DIEA
⟶
DMF

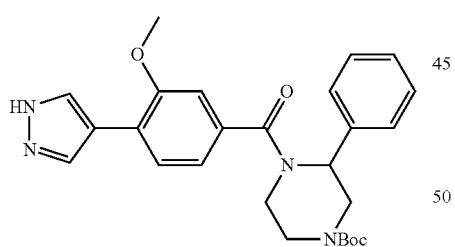

To a solution of Intermediate 1 (20 mg, 0.092 mmol) in DMF (1.5 mL) were added tert-butyl 3-phenylpiperazine-1-carboxylate (28.9 mg, 0.110 mmol), DIEA (0.080 mL, 0.458 mmol) and HATU (38.3 mg, 0.101 mmol) at rt. The reaction was stirred under argon at rt for 1 h. Purification by reverse phase chromatography afforded Example 68A (33 mg, 77%). LC-MS(ESI) m/z: 463.25[M+H]+; 1H NMR (400 MHz, DMSO-d6) δ 12.94 (br. s., 1H), 8.17 (br. s., 1H), 8.00 (br. s., 1H), 7.69 (d, J=7.7 Hz, 1H), 7.40 (d, J=11.9 Hz, 4H), 7.34-7.25 (m, 1H), 7.10 (br. s., 1H), 7.05 (d, J=7.5 Hz, 1H), 4.54 (d, J=13.4 Hz, 1H), 3.85 (br. s., 3H), 3.52-3.34 (m, 4H), 3.02 (br. s., 2H), 1.34 (br. s., 9H); Analytical HPLC RT=1.75 min (Method E), 1.68 min (Method F).

Example 68: 1-[3-Methoxy-4-(1H-pyrazol-4-yl)benzoyl]-2-phenylpiperazine

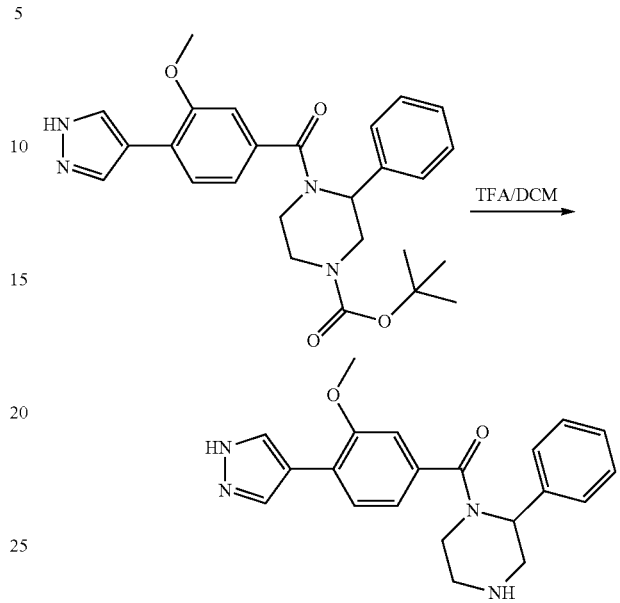

To a solution of Example 68A (27.8 mg, 0.06 mmol) in DCM (1 mL) was added TFA (0.5 mL, 6.49 mmol) at rt. The reaction was stirred under argon at rt for 1 h. The solvent was removed. Reverse phase chromatography purification afforded Example 68 (12.2 mg, 53%). LC-MS(ESI) m/z: 363.2[M+H]+; 1H NMR (400 MHz, DMSO-d6) δ 7.99 (br. s., 2H), 7.59 (d, J=7.5 Hz, 1H), 7.41-7.29 (m, 4H), 7.21 (br. s., 1H), 6.97 (s, 1H), 6.92 (d, J=7.7 Hz, 1H), 3.75 (br. s., 4H), 3.54-2.68 (m, 6H); Analytical HPLC RT=0.97 min (Method E), 0.99 min (Method F).

Example 69: 3-Methoxy-N-[(3S,4R)-4-phenylpyrrolidin-3-yl]-4-(1H-pyrazol-4-yl)benzamide

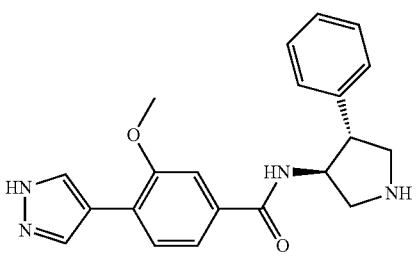 [SMILES: COc1cc(C(=O)N[C@@H]2CNC[C@H]2c2ccccc2)ccc1-c1cn[nH]c1]

Example 69 was prepared by following a similar procedure as described in Example 68. LC-MS(ESI) m/z: 363.0 [M+H]+; 1H NMR (500 MHz, DMSO-d6) δ 13.02 (br. s., 1H), 9.16 (br. s., 1H), 9.02 (br. s., 1H), 8.75 (d, J=7.4 Hz, 1H), 8.23 (br. s., 1H), 8.05 (br. s., 1H), 7.74 (d, J=7.2 Hz, 1H), 7.48-7.41 (m, 3H), 7.38 (t, J=7.4 Hz, 2H), 7.33-7.26 (m, 1H), 4.74 (t, J=8.7 Hz, 1H), 3.93 (s, 3H), 3.87-3.76 (m, 1H), 3.68 (quin, J=10.2 Hz, 2H), 3.19 (t, J=9.5 Hz, 1H); Analytical HPLC RT=1.04 min (Method E), 1.05 min (Method F).

Example 70: trans-(±)-3-Methoxy-N-(4-phenylpyrrolidin-3-yl)-4-(1H-pyrazol-4-yl)benzamide

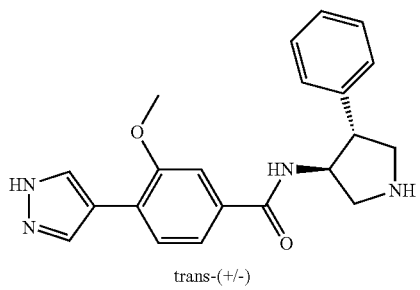 [SMILES: COc1cc(C(=O)N[C@@H]2CNC[C@H]2c2ccccc2)ccc1-c1cn[nH]c1]

trans-(+/-)

Example 70 was prepared by following a similar procedure as described in Example 69. LC-MS(ESI) m/z: 363.0 [M+H]⁺; ¹H NMR (500 MHz, DMSO-$d_6$) δ 9.13 (br. s., 1H), 9.00 (br. s., 1H), 8.73 (d, J=7.4 Hz, 1H), 8.13 (br. s., 2H), 7.73 (d, J=7.4 Hz, 1H), 7.46-7.40 (m, 4H), 7.37 (t, J=7.3 Hz, 2H), 7.31-7.25 (m, 1H), 4.72 (quin, J=8.4 Hz, 1H), 3.91 (s, 3H), 3.79 (br. s., 1H), 3.71-3.62 (m, 2H), 3.34 (br. s., 1H), 3.18 (br. s., 1H); Analytical HPLC RT=1.03 min (Method E), 1.06 min (Method F).

Example 71: 4-(2-Methoxy-4-{2-[3-(1H-pyrazol-4-yl)phenyl]pyrrolidine-1-carbonyl}phenyl)-1H-pyrazole

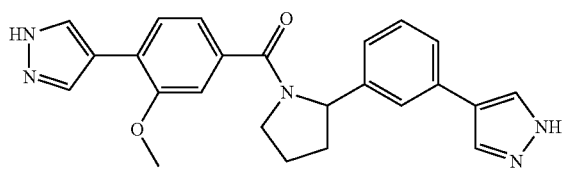 [SMILES: COc1cc(C(=O)N2CCCC2c2cccc(-c3cn[nH]c3)c2)ccc1-c1cn[nH]c1]

Example 71A: tert-Butyl 2-(3-bromophenyl)pyrrolidine-1-carboxylate

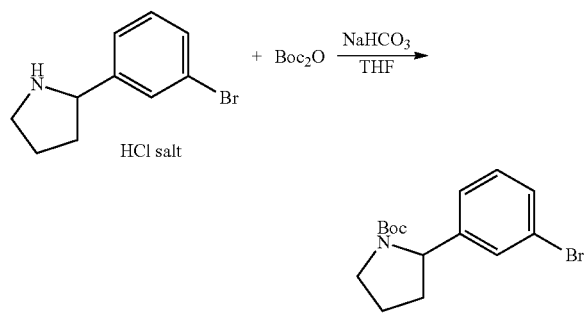

To a solution of 2-(3-bromophenyl)pyrrolidine HCl salt (1.05 g, 4.00 mmol) in THF (15 mL) were added NaHCO₃ (0.672 g, 8.00 mmol) and BOC₂O (1.021 mL, 4.40 mmol) at 0° C. The reaction was stirred under argon from 0° C. to rt overnight. The reaction mixture was filtered through a pad of CELITE®. The solvent was removed to give Example 71A as a light tan solid (1.30 g, 100%). LC-MS(ESI) m/z: 326/328[M+H]⁺; ¹H NMR (400 MHz, CDCl₃) δ 7.39-7.28 (m, 2H), 7.20-7.13 (m, 1H), 7.13-7.05 (singlets, 1H), 5.07-4.55 (singlets, 1H), 3.61 (br. s., 2H), 2.32 (br. s., 1H), 2.00-1.72 (m, 3H), 1.50-1.38 (m, 3H), 1.20 (br. s., 6H).

Example 71B: tert-Butyl 4-(3-(1-(tert-butoxycarbonyl)pyrrolidin-2-yl)phenyl)-1H-pyrazole-1-carboxylate

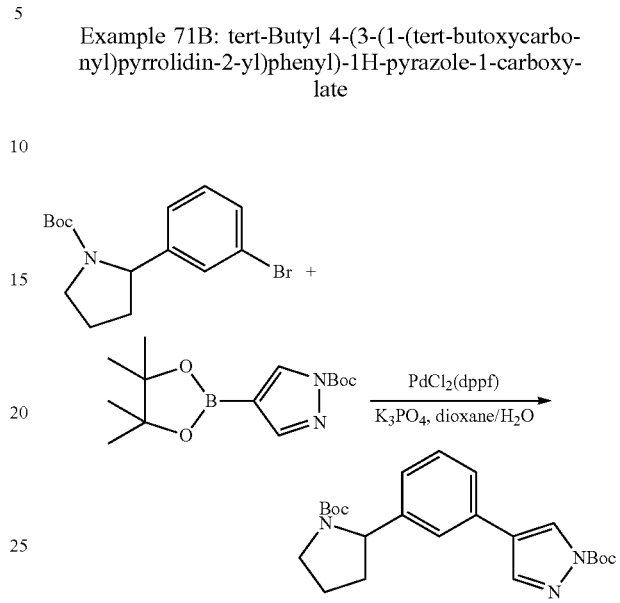

To a solution of Example 71A (30 mg, 0.092 mmol) in dioxane (1.5 mL) were added tert-butyl 4-(4,4,5,5-tetramethyl-1,3,2-dioxaborolan-2-yl)-1H-pyrazole-1-carboxylate (29.8 mg, 0.101 mmol), K₃PO₄ (0.5 mL, 0.500 mmol) and PdCl₂(dppf) (3.36 mg, 4.60 μmol) at rt. The reaction was stirred under argon at 90° C. for 1 h, and was cooled to rt. Solvent was removed. The crude product was purified by normal phase chromatography to afford Example 71B as a white solid (28 mg, 74%). LC-MS(ESI) m/z: 258.0[M-Boc-55]⁺; ¹H NMR (400 MHz, CDCl₃) δ 8.27 (s, 1H), 7.96 (s, 1H), 7.41-7.28 (m, 3H), 7.10 (d, J=7.5 Hz, 1H), 5.17-4.62 (m, 1H), 3.64 (br. s., 2H), 2.35 (br. s., 1H), 1.99-1.78 (m, 3H), 1.68 (s, 9H), 1.46 (br. s., 3H), 1.17 (br. s., 6H).

Example 71

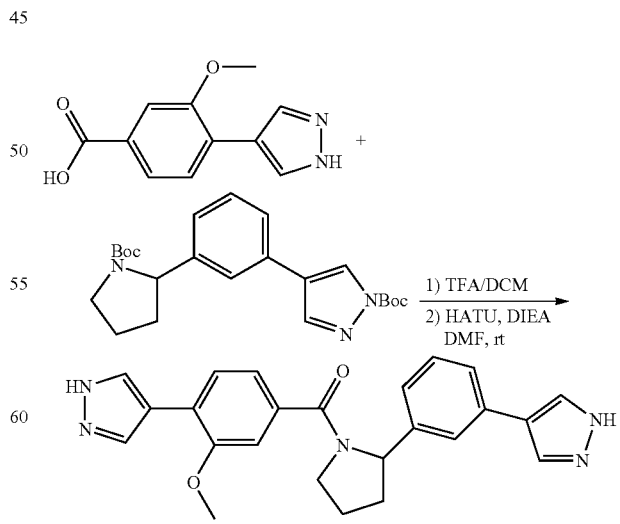

To a solution of Example 71B (18.61 mg, 0.045 mmol) in DCM (1 mL) was added TFA (0.5 mL, 6.49 mmol). The reaction was stirred at rt for 30 min. The solvent was removed. To the residue was added DMF (1 mL), followed by the addition of Intermediate 1 (9.82 mg, 0.045 mmol), DIEA (0.05 mL, 0.286 mmol) and HATU (17.11 mg, 0.045 mmol) at rt. The reaction was stirred under argon at rt for 1 h. Purification by reverse phase chromatography afforded Example 71 (16.9 mg, 87%). LC-MS(ESI) m/z: 414.20[M+H]$^+$; $^1$H NMR (500 MHz, DMSO-d$_6$) δ 8.11 (br. s., 4H), 7.76-7.42 (m, 3H), 7.38-7.12 (m, 3H), 7.06-6.70 (m, 1H), 5.26-4.86 (m, 1H), 4.02-3.71 (m, 3H), 3.59 (br. s., 1H), 3.45-3.34 (m, 1H), 2.46-2.22 (m, 1H), 2.01-1.71 (m, 3H); Analytical HPLC RT=1.23 min (Method E), 1.30 min (Method F).

The following Examples in Table 4 were prepared by using the similar procedure as described in Example 71.

TABLE 4

| Ex. No. | Structure | Name | LCMS (M + H)+ | HPLC Method, RT (min.) | 1H NMR (ppm) |
|---|---|---|---|---|---|
| 72 | 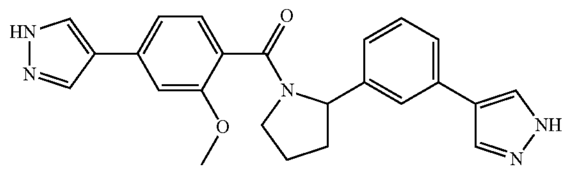 | 4-(3-methoxy-4-{2-[3-(1H-pyrazol-4-yl)phenyl]pyrrolidine-1-carbonyl}phenyl)-1H-pyrazole | 414.2 | E: 1.22 F: 1.33 | (500 MHz, DMSO-d$_6$) δ 8.05 (br. s., 4H), 7.56-7.46 (m, 1H), 7.46-7.32 (m, 2H), 7.32-7.09 (m, 3H), 7.08-6.70 (m, 1H), 5.26-4.67 (m, 1H), 4.06-3.86 (m, 3H), 3.80-3.15 (m, 2H), 2.43-2.21 (m, 1H), 2.00-1.69 (m, 3H) |
| 73 | 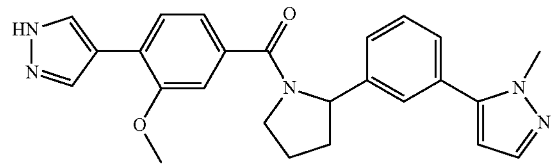 [SMILES: COc1cc(C(=O)N2CCCC2c2cccc(-c3ccnn3C)c2)ccc1-c1cn[nH]c1] | 5-(3-{1-[3-methoxy-4-(1H-pyrazol-4-yl)benzoyl]pyrrolidin-2-yl}phenyl)-1-methyl-1H-pyrazole | 428.2 | E: 1.34 F: 1.42 | (500 MHz, DMSO-d$_6$) δ 8.32-7.84 (m, 2H), 7.75-7.29 (m, 5H), 7.28-7.09 (m, 2H), 6.91-6.58 (m, 1H), 6.48-6.22 (m, 1H), 5.30-4.92 (m, 1H), 4.00-3.53 (m, 5H), 3.49-3.27 (m, 3H), 2.46-2.25 (m, 1H), 2.01-1.69 (m, 3H) |
| 74 | 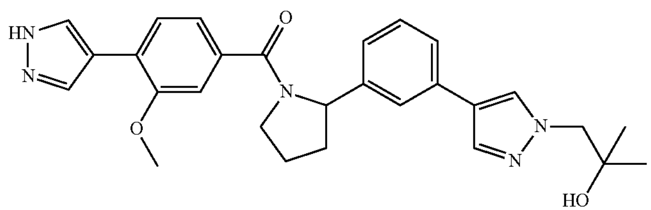 [SMILES: COc1cc(C(=O)N2CCCC2c2cccc(-c3cnn(CC(C)(C)O)c3)c2)ccc1-c1cn[nH]c1] | 1-[4-(3-{1-[3-methoxy-4-(1H-pyrazol-4-yl)benzoyl]pyrrolidin-2-yl}phenyl)-1H-pyrazol-1-yl]-2-methylpropan-2-ol | 486.3 | E: 1.32 F: 1.37 | (500 MHz, DMSO-d$_6$) δ 8.20-8.02 (m, 2H), 7.91-7.65 (m, 2H), 7.50 (br. s., 1H), 7.42 (d, J = 7.4 Hz, 1H), 7.35-6.96 (m, 4H), 6.91-6.70 (m, 1H), 5.23-4.94 (m, 1H), 4.82-4.67 (m, 1H), 4.09-3.53 (m, 5H), 3.17 (d, J = 5.0 Hz, 2H), 2.44-2.20 (m, 1H), 1.91-1.76 (m, 3H), 1.08 (br. s., 6H) |

TABLE 4-continued

| Ex. No. | Structure | Name | LCMS (M + H)+ | HPLC Method, RT (min.) | 1H NMR (ppm) |
|---|---|---|---|---|---|
| 75 | 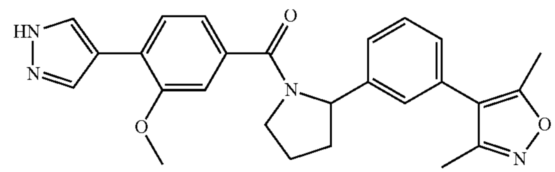 [SMILES: COc1cc(C(=O)N2CCCC2c2cccc(-c3c(C)noc3C)c2)ccc1-c1cn[nH]c1] | 4-(3-{1-[3-methoxy-4-(1H-pyrazol-4-yl)benzoyl]pyrrolidin-2-yl}phenyl)-3,5-dimethyl-1,2-oxazole | 443.2 | E: 1.42<br>F: 1.44 | (500 MHz, DMSO-d$_6$) δ 8.20-7.97 (m, 2H), 7.77-7.48 (m, 1H), 7.48-7.40 (m, 1H), 7.39-7.31 (m, 1H), 7.29-7.11 (m, 3H), 7.08-6.57 (m, 1H), 5.37-4.91 (m, 1H), 4.03-3.36 (m, 5H), 2.47-2.29 (m, 4H), 2.25 (s, 2H), 2.14 (br. s., 1H), 2.01-1.72 (m, 3H) |
| 76 | 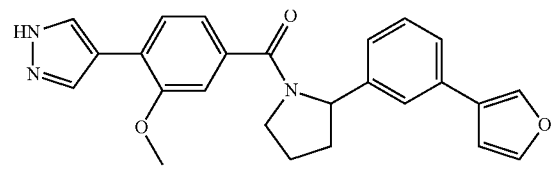 [SMILES: COc1cc(C(=O)N2CCCC2c2cccc(-c3ccoc3)c2)ccc1-c1cn[nH]c1] | 4-(4-{2-[3-(furan-3-yl)phenyl]pyrrolidine-1-carbonyl}-2-methoxyphenyl)-1H-pyrazole | 414.2 | E: 1.62<br>F: 1.66 | (500 MHz, DMSO-d$_6$) δ 8.31-8.09 (m, 2H), 8.09-7.89 (m, 1H), 7.83-7.65 (m, 2H), 7.59-7.44 (m, 2H), 7.40-7.18 (m, 3H), 7.13-6.67 (m, 2H), 5.29-4.88 (m, 1H), 4.04-3.34 (m, 5H), 2.47-2.22 (m, 1H), 2.01-1.73 (m, 3H) |
| 77 | 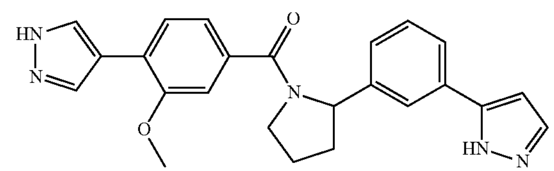 [SMILES: COc1cc(C(=O)N2CCCC2c2cccc(-c3ccn[nH]3)c2)ccc1-c1cn[nH]c1] | 4-(2-methoxy-4-{2-[3-(1H-pyrazol-5-yl)phenyl]pyrrolidine-1-carbonyl}phenyl)-1H-pyrazole | 414.0 | E: 1.23<br>F: 1.31 | (500 MHz, DMSO-d$_6$) δ 8.12 (br. s., 2H), 7.84-7.47 (m, 4H), 7.43-6.64 (m, 5H), 5.36-4.90 (m, 1H), 4.08-3.13 (m, 5H), 2.45-2.21 (m, 1H), 2.00-1.70 (m, 3H) |

Example 78: N-Cyclopropyl-3-[(2R)-4-fluoro-1-[3-methoxy-4-(1H-pyrazol-4-yl)benzoyl] pyrrolidin-2-yl]benzamide

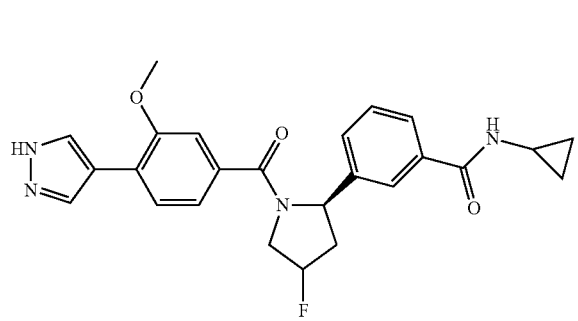 [SMILES: COc1cc(C(=O)N2CC(F)C[C@@H]2c2cccc(C(=O)NC3CC3)c2)ccc1-c1cn[nH]c1]

Example 78A: Methyl 3-((2R)-4-acetoxy-1-(4-bromo-3-methoxybenzoyl)pyrrolidin-2-yl)benzoate

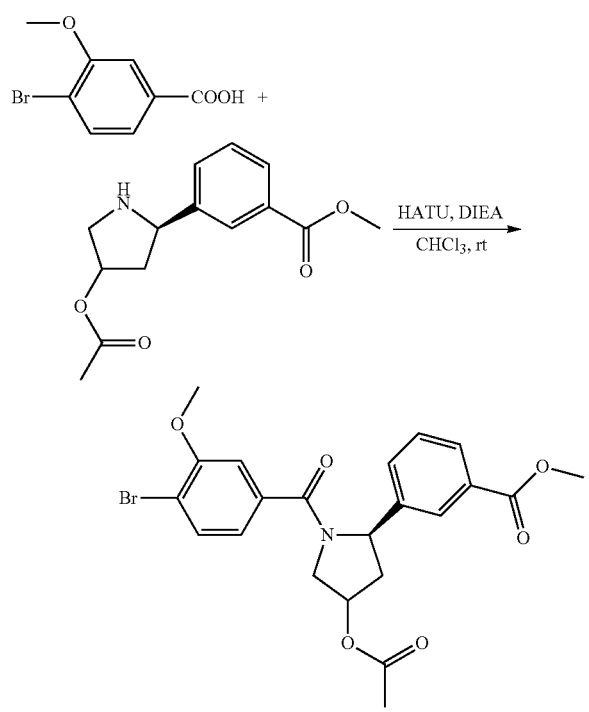

To a solution of Intermediate 3 (200 mg, 0.760 mmol) in CHCl$_3$ (5 mL) were added 4-bromo-3-methoxybenzoic acid (176 mg, 0.760 mmol), DIEA (0.265 mL, 1.519 mmol) and HATU (318 mg, 0.836 mmol) at rt. The reaction was stirred under argon at rt for 3 h. Most solvent was removed. The crude product was purified by normal phase chromatography to afford Example 78A as a white solid (310 mg, 86%). LC-MS(ESI) m/z: 476.0/478.0[M+H]$^+$; $^1$H NMR (400 MHz, CDCl$_3$) δ 8.13-7.76 (m, 2H), 7.56 (d, J=9.2 Hz, 2H), 7.47-7.35 (m, 1H), 7.24-6.94 (m, 2H), 5.54-4.96 (m, 2H), 3.91 (s, 6H), 3.84-3.40 (m, 2H), 2.81-2.44 (m, 1H), 2.35-2.17 (m, 1H), 2.10-1.97 (m, 3H).

Example 78B: 3-((2R)-1-(4-Bromo-3-methoxybenzoyl)-4-hydroxypyrrolidin-2-yl)benzoic acid

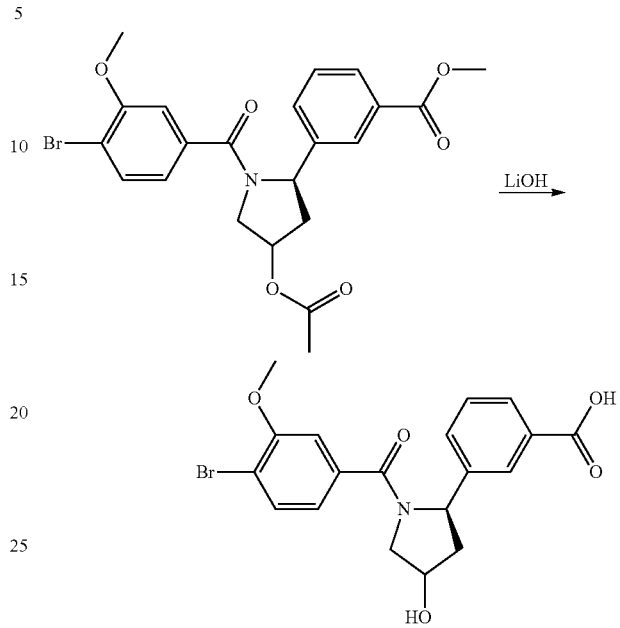

To a solution of Example 78A (310 mg, 0.651 mmol) in THF (10 mL) and water (3 mL) was added LiOH (78 mg, 3.25 mmol) at rt. The reaction was stirred under argon at rt overnight. The reaction mixture was diluted with EtOAc, washed with 1M HCl and brine. The organic phase was dried over Na$_2$SO$_4$, filtered and concentrated to afford Example 78B as a white solid (285 mg, 100%). LC-MS(ESI) m/z: 420.0/422.0[M+H]$^+$; $^1$H NMR (400 MHz, DMSO-d$_6$) δ 7.97-7.86 (m, 1H), 7.80 (d, J=7.5 Hz, 1H), 7.72-7.60 (m, 2H), 7.46 (t, J=7.5 Hz, 1H), 7.30-7.07 (m, 2H), 5.23 (t, J=8.7 Hz, 1H), 5.15-4.98 (m, 1H), 4.28 (br. s., 1H), 4.09-3.98 (m, 1H), 3.90 (s, 3H), 2.70-2.54 (m, 1H), 2.43-2.26 (m, 1H).

Example 78C: 3-((2R)-1-(4-Bromo-3-methoxybenzoyl)-4-hydroxypyrrolidin-2-yl)-N-cyclopropylbenzamide

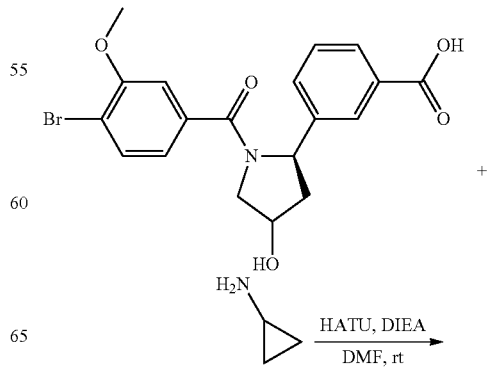

-continued

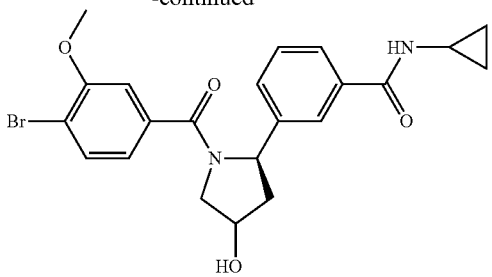

To a solution of Example 78B (95 mg, 0.226 mmol) in DMF (3 mL) were added cyclopropanamine (25.8 mg, 0.452 mmol), DIEA (0.118 mL, 0.678 mmol) and HATU (103 mg, 0.271 mmol) at rt. The reaction was stirred under argon at rt for 2 h. The reaction mixture was diluted with EtOAc, washed with H₂O and brine. The organic phase was dried over sodium sulfate, filtered and concentrated. The crude product was purified by normal phase chromatography to afford Example 78C as a white solid (68 mg, 66%). LC-MS (ESI) m/z: 459.1/461.1[M+H]⁺; ¹H NMR (400 MHz, CDCl₃) δ 8.07-7.66 (m, 1H), 7.63-7.28 (m, 4H), 7.14-6.45 (m, 3H), 5.54-4.85 (m, 1H), 4.68-4.23 (m, 1H), 4.07-3.32 (m, 5H), 2.84-2.35 (m, 2H), 2.03 (d, J=3.5 Hz, 1H), 0.82 (d, J=5.5 Hz, 2H), 0.59 (d, J=4.0 Hz, 2H).

Example 78D: 3-((2R)-1-(4-Bromo-3-methoxybenzoyl)-4-fluoropyrrolidin-2-yl)-N-cyclopropylbenzamide

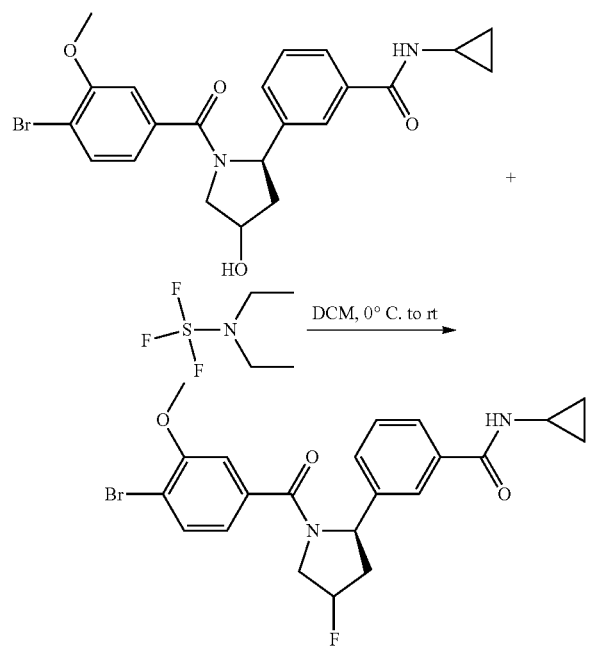

To a solution of Example 78C (68 mg, 0.148 mmol) in DCM (5 mL) was added DAST (0.098 mL, 0.740 mmol) at 0° C. The reaction was stirred under argon from 0° C. to rt overnight. MeOH (1 mL) was added to quench the reaction and the solvent was removed. The crude product was purified by normal phase chromatography to afford Example 78D (55 mg, 81%). LC-MS(ESI) m/z: 461.0/463.0[M+H]⁺; ¹H NMR (400 MHz, CDCl₃) δ 7.97-7.29 (m, 4H), 7.23-5.80 (m, 3H), 5.74-4.86 (m, 2H), 4.22-3.28 (m, 6H), 2.81-2.02 (m, 2H), 0.92-0.78 (m, 2H), 0.73-0.53 (m, 2H).

Example 78

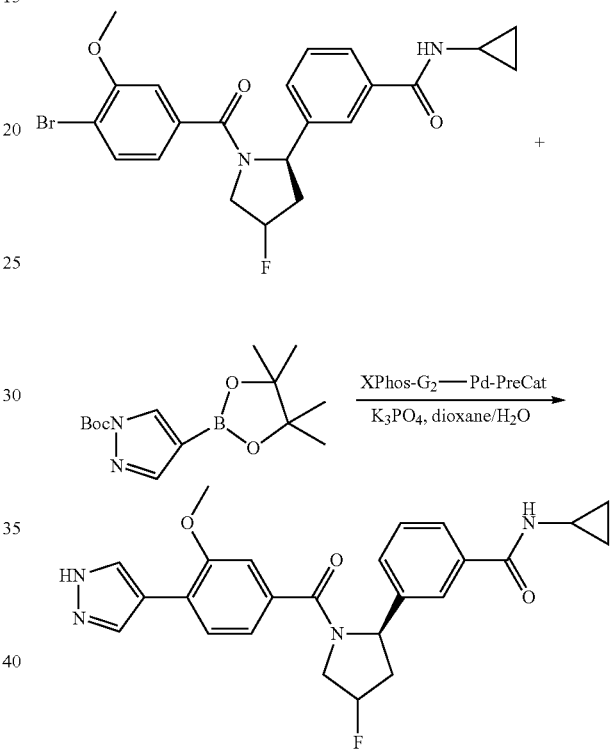

To a solution of Example 78D (55 mg, 0.119 mmol) in dioxane (3 mL) were added tert-butyl 4-(4,4,5,5-tetramethyl-1,3,2-dioxaborolan-2-yl)-1H-pyrazole-1-carboxylate (52.6 mg, 0.179 mmol), K₃PO₄ (1 M, 0.358 mL, 0.358 mmol) and XPhos-G2-Pd-PreCat (4.69 mg, 5.96 μmol) at rt. The reaction was stirred under argon at 90° C. for 1 h. The reaction was cooled to rt. It was extracted with EtOAc, and the solvent was removed. To the residue were added DCM (1 mL) and TFA (0.5 mL). After stirred at rt for 30 min, the solvent was removed. Purification by reverse phase chromatography afforded Example 78 (23.6 mg, 44%). LC-MS (ESI) m/z: 449.20[M+H]⁺; ¹H NMR (500 MHz, DMSO-d₆) δ 8.46 (br. s., 1H), 8.13 (br. s., 2H), 7.88-7.31 (m, 5H), 7.28-6.73 (m, 2H), 5.57-5.05 (m, 2H), 4.41-3.33 (m, 5H), 2.86-2.59 (m, 2H), 2.23 (br. s., 1H), 0.69 (br. s., 2H), 0.56 (br. s., 2H); Analytical HPLC RT=1.14 min (Method E), 1.17 min (Method F).

Example 79: N-Cyclopropyl-3-[(2R)-4,4-difluoro-1-[3-methoxy-4-(pyridin-4-yl)benzoyl] pyrrolidin-2-yl]benzamide

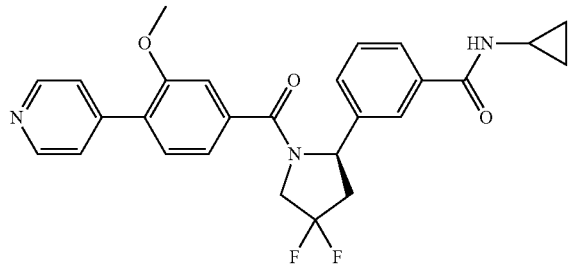 [SMILES: COc1cc(C(=O)N2CC(F)(F)C[C@@H]2c2cccc(C(=O)NC3CC3)c2)ccc1-c1ccncc1]

Example 79A: (R)-3-(1-(4-Bromo-3-methoxybenzoyl)-4-oxopyrrolidin-2-yl)-N-cyclopropylbenzamide

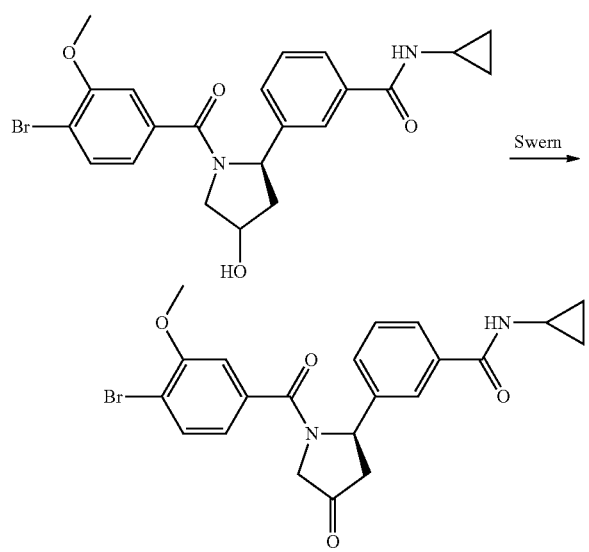

To a solution of oxalyl chloride (0.431 mL, 0.862 mmol) in DCM (5 mL) was added DMSO (0.122 mL, 1.724 mmol) at −78° C. The reaction was stirred under argon at −78° C. for 10 min. Then a solution of Example 78C (132 mg, 0.287 mmol) dissolved in DCM (2 mL) was added. The reaction was stirred at −78° C. for 15 min and then at −50° C. for 30 min. To the reaction was then added TEA (0.360 mL, 2.59 mmol) at the same temperature. The reaction was allowed to warm up to rt over 30 min. The reaction mixture was diluted with CH$_2$Cl$_2$, washed with saturated NH$_4$Cl solution. The organic phase was dried over sodium sulfate, filtered and concentrated. Purification by normal phase chromatography afforded Example 79A as a light brown solid (128 mg, 97%). LC-MS(ESI) m/z: 456.9/458.9[M+H]$^+$; $^1$H NMR (400 MHz, CDCl$_3$) δ 7.61 (d, J=7.5 Hz, 2H), 7.57-7.28 (m, 3H), 7.10-6.66 (m, 2H), 6.50 (br. s., 1H), 4.23-3.54 (m, 4H), 3.45 (s, 2H), 3.15 (dd, J=18.5, 9.9 Hz, 1H), 2.92-2.81 (m, 1H), 2.77-2.51 (m, 1H), 0.84 (q, J=6.1 Hz, 2H), 0.65-0.53 (m, 2H).

Example 79B: (R)-3-(1-(4-Bromo-3-methoxybenzoyl)-4,4-difluoropyrrolidin-2-yl)-N-cyclopropylbenzamide

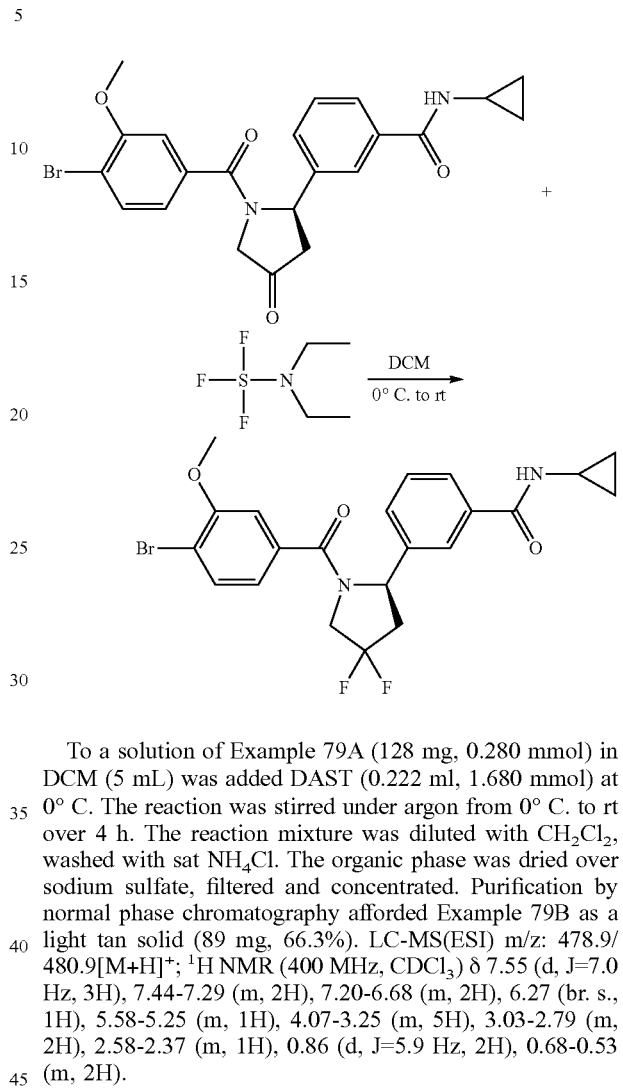

To a solution of Example 79A (128 mg, 0.280 mmol) in DCM (5 mL) was added DAST (0.222 ml, 1.680 mmol) at 0° C. The reaction was stirred under argon from 0° C. to rt over 4 h. The reaction mixture was diluted with CH$_2$Cl$_2$, washed with sat NH$_4$Cl. The organic phase was dried over sodium sulfate, filtered and concentrated. Purification by normal phase chromatography afforded Example 79B as a light tan solid (89 mg, 66.3%). LC-MS(ESI) m/z: 478.9/480.9[M+H]$^+$; $^1$H NMR (400 MHz, CDCl$_3$) δ 7.55 (d, J=7.0 Hz, 3H), 7.44-7.29 (m, 2H), 7.20-6.68 (m, 2H), 6.27 (br. s., 1H), 5.58-5.25 (m, 1H), 4.07-3.25 (m, 5H), 3.03-2.79 (m, 2H), 2.58-2.37 (m, 1H), 0.86 (d, J=5.9 Hz, 2H), 0.68-0.53 (m, 2H).

Example 79

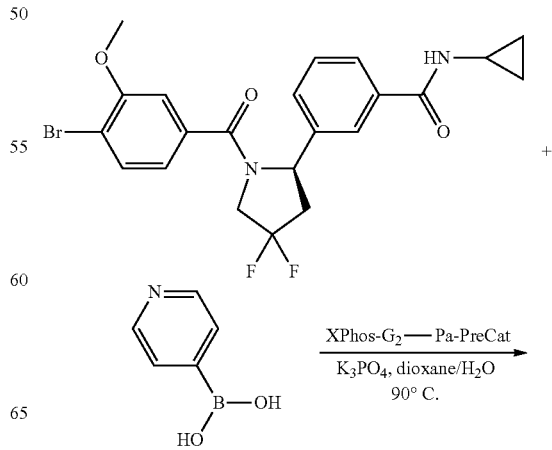

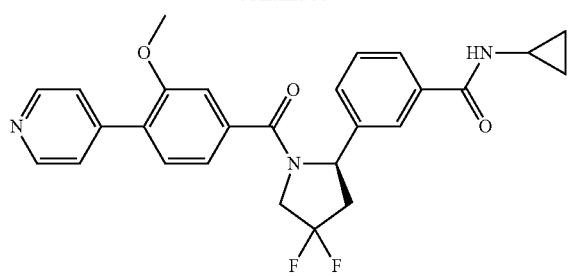

To a solution of Example 79B (45 mg, 0.094 mmol) in dioxane (2 mL) were added pyridin-4-ylboronic acid (13.85 mg, 0.113 mmol), $K_3PO_4$ (1 M, 0.282 mL, 0.282 mmol) and XPhos-G2-Pd-PreCat (3.69 mg, 4.69 µmol) at rt. The reaction was stirred under argon at 90° C. for 1 h. Solvent was removed. Purification by reverse phase chromatography afforded Example 79 (27.1 mg, 60.5%). LC-MS(ESI) m/z: 478.2[M+H]$^+$; $^1$H NMR (500 MHz, DMSO-$d_6$) δ 8.84 (br. s., 2H), 8.58-8.35 (m, 1H), 8.05 (br. s., 1H), 7.86 (br. s., 1H), 7.77-6.73 (m, 7H), 5.56-5.15 (m, 1H), 4.68-4.11 (m, 1H), 4.07-3.81 (m, 3H), 3.65-3.45 (m, 1H), 3.15-2.95 (m, 1H), 2.86-2.75 (m, 1H), 2.48-2.31 (m, 1H), 0.70 (br. s., 2H), 0.61-0.39 (m, 2H); Analytical HPLC RT=1.01 min (Method E), 1.39 min (Method F).

Example 80: N-Cyclopropyl-3-[(2R)-4,4-difluoro-1-[3-methoxy-4-(1H-pyrazol-4-yl)benzoyl]pyrrolidin-2-yl]benzamide

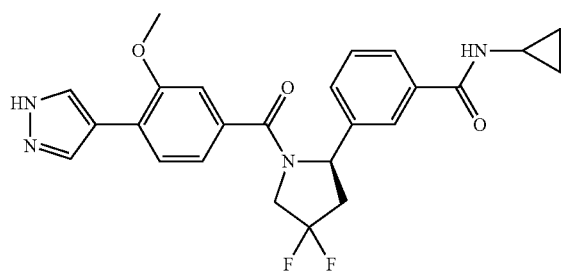 [SMILES: COc1cc(C(=O)N2CC(F)(F)C[C@@H]2c2cccc(C(=O)NC3CC3)c2)ccc1-c1cn[nH]c1]

Example 80 was prepared by following the same procedure as that described in Example 79, by replacing pyridin-4-ylboronic acid with tert-butyl 4-(4,4,5,5-tetramethyl-1,3,2-dioxaborolan-2-yl)-1H-pyrazole-1-carboxylate in 79C. LC-MS(ESI) m/z: 467.2[M+H]$^+$; $^1$H NMR (500 MHz, DMSO-$d_6$) δ 8.48 (br. s., 1H), 8.14 (br. s., 2H), 7.91-7.53 (m, 4H), 7.51-7.16 (m, 3H), 5.41 (br. s., 1H), 4.10-3.41 (m, 6H), 3.06 (br. s., 1H), 2.84 (br. s., 1H), 0.71 (d, J=5.4 Hz, 2H), 0.57 (br. s., 2H); Analytical HPLC RT=1.22 min (Method E), 1.28 min (Method F).

Example 81: 4-{2-Methoxy-4-[2-(3-methoxyphenyl)pyrrolidine-1-carbonyl]phenyl} pyridin-2-amine

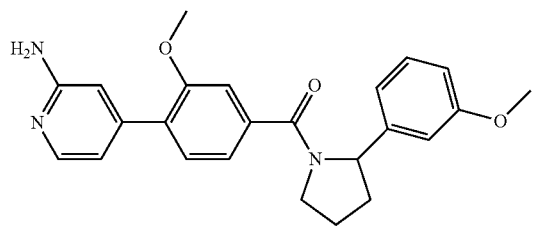 [SMILES: COc1cccc(C2CCCN2C(=O)c2ccc(-c3ccnc(N)c3)c(OC)c2)c1]

Example 81A: (4-Bromo-3-methoxyphenyl)(2-(3-methoxyphenyl)pyrrolidin-1-yl)methanone

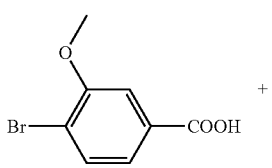

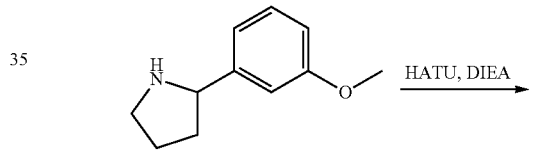

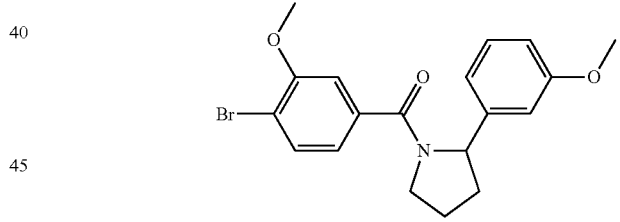

To a solution of 4-bromo-3-methoxybenzoic acid (700 mg, 3.03 mmol) in DMF (8 mL) were added 2-(3-methoxyphenyl)pyrrolidine (537 mg, 3.03 mmol), DIEA (1.058 mL, 6.06 mmol) and HATU (1267 mg, 3.33 mmol) at 0° C. The reaction was stirred under argon at 0° C. for 1 h. The reaction mixture was diluted with EtOAc, washed with 1M HCl, 1 M $K_2HPO_4$ and brine. The organic phase was dried over sodium sulfate, filtered and concentrated. The crude product was purified by normal phase chromatography to afford Example 81A as a light tan solid (1.10 g, 93%). LC-MS(ESI) m/z: 389.9/391.9[M+H]$^+$; $^1$H NMR (400 MHz, CDCl$_3$) δ 7.66-7.33 (m, 1H), 7.30-6.88 (m, 2H), 6.86-6.45 (m, 4H), 5.38-4.64 (m, 1H), 4.04-3.34 (m, 8H), 2.54-2.12 (m, 1H), 2.03-1.66 (m, 3H).

Example 81

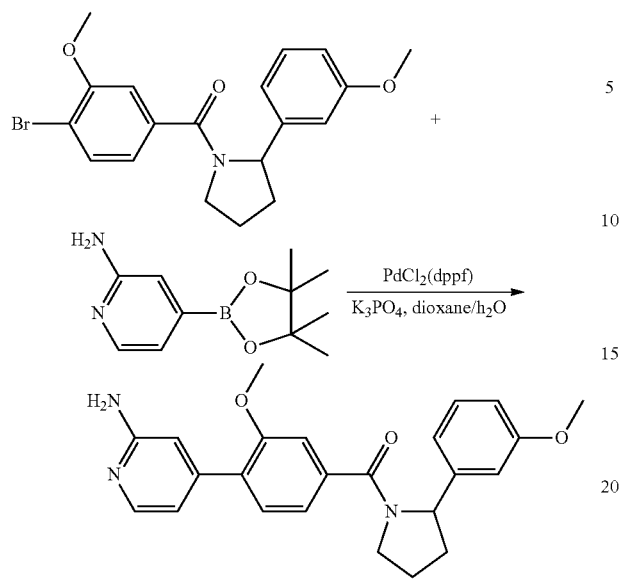

To a solution of Example 81A (30 mg, 0.077 mmol) in dioxane (1.5 mL) were added 4-(4,4,5,5-tetramethyl-1,3,2-dioxaborolan-2-yl)pyridin-2-amine (33.8 mg, 0.154 mmol), $K_3PO_4$ (1 M, 0.231 mL, 0.231 mmol) and $PdCl_2(dppf)$ (5.62 mg, 7.69 μmol) at rt. The reaction was stirred under argon at 90° C. for 1 h. Purification by reverse phase chromatography afforded Example 81 (18.4 mg, 59.3%). LC-MS(ESI) m/z: 404.2[M+H]$^+$; $^1$H NMR (500 MHz, DMSO-$d_6$) δ 7.95-7.83 (m, 1H), 7.41-6.85 (m, 5H), 6.83-5.90 (m, 5H), 5.22-4.82 (m, 1H), 3.89-3.38 (m, 8H), 2.44-2.20 (m, 1H), 1.91-1.66 (m, 3H); Analytical HPLC RT=1.28 min (Method E), 1.51 min (Method F).

The following Examples in Table 5 were prepared by using the similar procedure as described in Example 81.

TABLE 5

| Ex. No. | Structure | Name | LCMS (M + H)$^+$ | HPLC Method, RT (min.) | $^1$H NMR (ppm) |
|---|---|---|---|---|---|
| 82 | 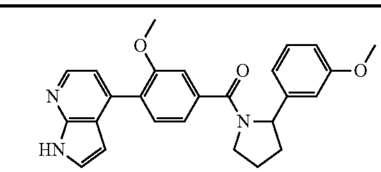 | 1-(3-methoxy-4-{1H-pyrrolo[2,3-b]pyridin-4-yl}benzoyl)-2-(3-methoxyphenyl)pyrrolidine | 428.2 | E: 1.25 F: 1.67 | (500 MHz, DMSO-$d_6$) δ 12.02 (br. s., 1H), 8.40-8.19 (m, 1H), 7.56 (br. s., 1H), 7.52-7.08 (m, 4H), 6.93 (d, J = 6.7 Hz, 1H), 6.90-6.74 (m, 2H), 6.74-6.56 (m, 1H), 6.44-6.15 (m, 1H), 5.23-4.85 (m, 1H), 3.97-3.29 (m, 8H), 2.44-2.24 (m, 1H), 2.03-1.69 (m, 3H) |
| 83 | 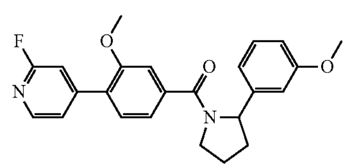 [SMILES: COc1cccc(C2CCCN2C(=O)c2ccc(-c3ccnc(F)c3)c(OC)c2)c1] | 2-fluoro-4-{2-methoxy-4-[2-(3-methoxyphenyl)pyrrolidine-1-carbonyl]phenyl}pyridine | 407.2 | E: 1.75 F: 1.75 | (500 MHz, DMSO-$d_6$) δ 8.35-8.20 (m, 1H), 7.55 (d, J = 6.7 Hz, 1H), 7.46-7.19 (m, 4H), 6.99-6.54 (m, 4H), 5.24-4.84 (m, 1H), 3.96-3.37 (m, 8H), 2.44-2.23 (m, 1H), 2.02-1.70 (m, 3H) |
| 84 | 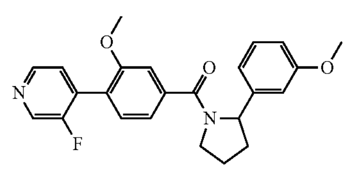 | 3-fluoro-4-{2-methoxy-4-[2-(3-methoxyphenyl)pyrrolidine-1-carbonyl]phenyl}pyridine | 407.2 | E: 1.40 F: 1.61 | (500 MHz, DMSO-$d_6$) δ 8.69-8.56 (m, 1H), 8.53-8.40 (m, 1H), 7.52-7.16 (m, 4H), 6.96-6.56 (m, 4H), 5.22-4.81 (m, 1H), 3.91-3.28 (m, 8H), 2.42-2.23 (m, 1H), 2.00-1.67 (m, 3H) |
| 85 | 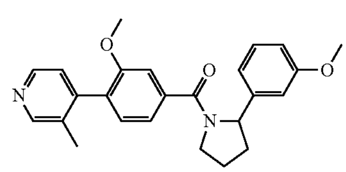 [SMILES: COc1cccc(C2CCCN2C(=O)c2ccc(-c3ccncc3C)c(OC)c2)c1] | 4-{2-methoxy-4-[2-(3-methoxyphenyl)pyrrolidine-1-carbonyl]phenyl}-3-methylpyridine | 403.2 | E: 1.17 F: 1.68 | (500 MHz, DMSO-$d_6$) δ 8.61-8.29 (m, 2H), 7.33-7.03 (m, 4H), 7.02-6.91 (m, 1H), 6.89 (br. s., 1H), 6.84-6.63 (m, 2H), 5.22-4.83 (m, 1H), 3.93-3.35 (m, 8H), 2.46-2.26 (m, 1H), 2.09, 1.97 (s, 2H), 1.94-1.71 (m, 3H) |
| 99 | 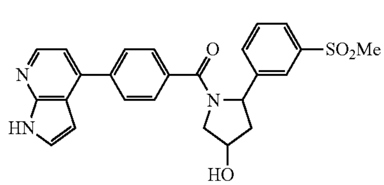 [SMILES: CS(=O)(=O)c1cccc(C2CC(O)CN2C(=O)c2ccc(-c3ccnc4[nH]ccc34)cc2)c1] | (5R)-5-(3-methanesulfonylphenyl)-1-(4-{1H-pyrrolo[2,3-b]pyridin-4-yl}benzoyl)pyrrolidin-3-ol | 462.1 | E: 0.66 F: 0.97 | (500 MHz, DMSO-$d_6$) δ 11.94 (br. s., 1H), 8.40-8.23 (m, 1H), 7.92-7.86 (m, 2H), 7.80 (d, J = 7.7 Hz, 3H), 7.67-7.55 (m, 2H), 7.35-7.18 (m, 2H), 7.15-6.98 (m, 1H), 6.73-6.47 (m, 1H), 5.43-5.16 (m, 1H), 4.50-4.24 (m, 1H), 4.12 (d, J = 8.4 Hz, 1H), 3.29-2.95 (m, 3H), 2.46-2.33 (m, 1H), 1.96-1.74 (m, 1H) |

Example 86: N-(Cyclopropylmethyl)-3-[(2R)-4-methoxy-1-[3-methoxy-4-(1H-pyrazol-4-yl)benzoyl]pyrrolidin-2-yl]benzamide

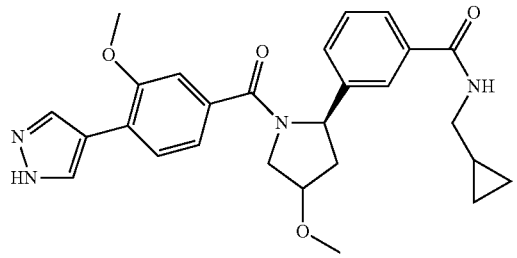 [SMILES: COc1cc(C(=O)N2CC(OC)C[C@@H]2c2cccc(C(=O)NCC3CC3)c2)ccc1-c1cn[nH]c1]

Example 86A: 3-((2R)-1-(4-Bromo-3-methoxybenzoyl)-4-hydroxypyrrolidin-2-yl)-N-(cyclopropylmethyl)benzamide

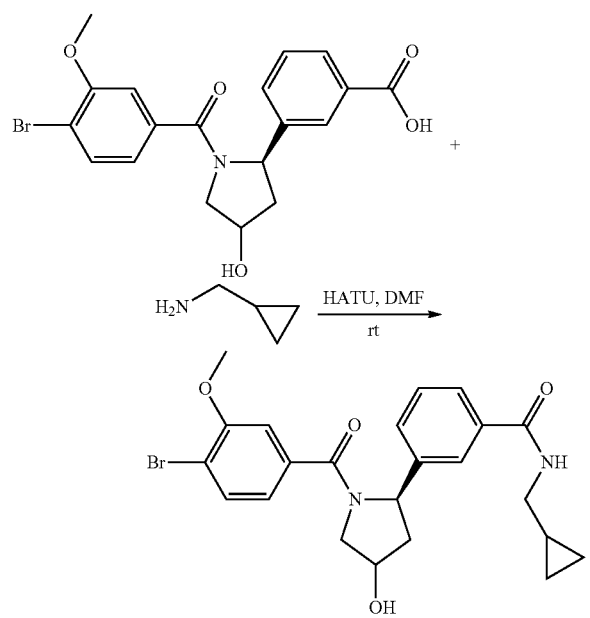

To a solution of Example 78A (200 mg, 0.476 mmol) in DMF (10 mL) were added cyclopropylmethanamine (50.8 mg, 0.714 mmol), DIEA (0.249 mL, 1.428 mmol) and HATU (199 mg, 0.523 mmol) at rt. The reaction was stirred under argon at rt for 3 h. The reaction mixture was diluted with EtOAc, washed with H$_2$O and brine. The organic phase was dried over sodium sulfate, filtered and concentrated. Purification by normal phase chromatography afforded Example 86A as an off-white solid (185 mg, 82%). LC-MS (ESI) m/z: 473.0/474.9[M+H]$^+$; $^1$H NMR (400 MHz, DMSO-d$_6$) δ 8.39-8.17 (m, 1H), 7.57 (s, 1H), 7.50-7.33 (m, 2H), 7.32-7.23 (m, 1H), 7.20-7.09 (m, 1H), 6.99 (s, 1H), 6.90 (d, J=7.9 Hz, 1H), 5.08-4.93 (m, 1H), 4.79 (d, J=2.6 Hz, 1H), 4.15-3.75 (m, 2H), 3.67 (s, 3H), 3.27 (br. s., 1H), 2.94-2.89 (m, 2H), 1.70-1.43 (m, 1H), 1.07-0.99 (m, 1H), 0.79 (d, J=6.8 Hz, 1H), 0.25-0.13 (m, 2H), 0.00 (d, J=4.0 Hz, 2H).

Example 86B: 3-((2R)-1-(4-Bromo-3-methoxybenzoyl)-4-methoxypyrrolidin-2-yl)-N-(cyclopropylmethyl)benzamide, and Example 86C: 3-((2R)-1-(4-Bromo-3-methoxybenzoyl)-4-methoxypyrrolidin-2-yl)-N-(cyclopropylmethyl)-N-methylbenzamide

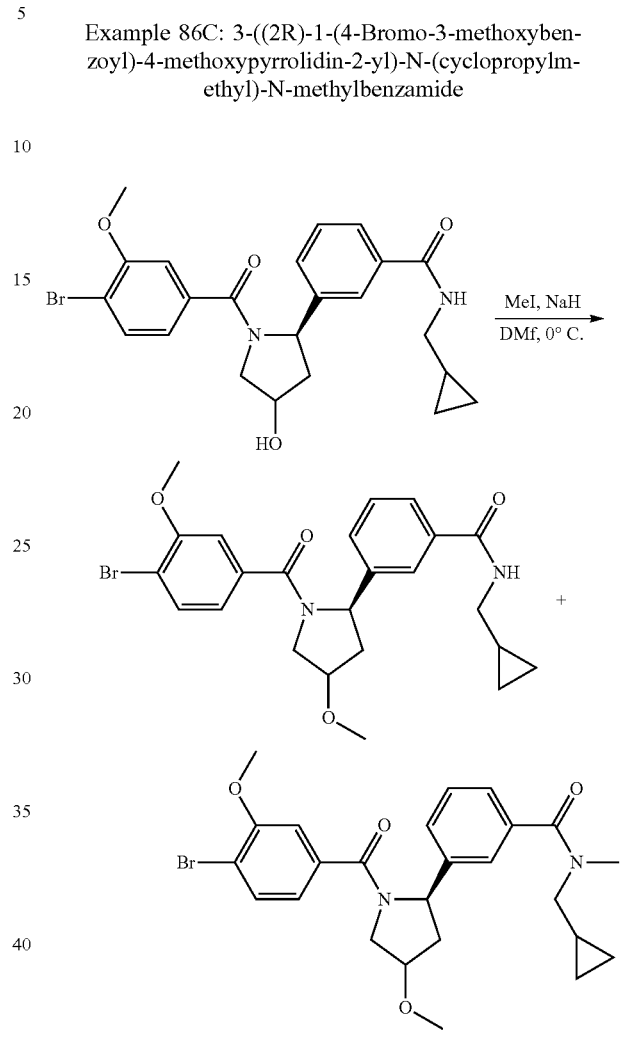

To a solution of Example 86A (30 mg, 0.063 mmol) in DMF (2 mL) were added NaH (7.60 mg, 0.190 mmol) and MeI (0.038 mL, 0.076 mmol) at 0° C. The reaction was stirred under argon at 0° C. for 1 h. The reaction was quenched with MeOH. Purification by reverse phase chromatography afforded Example 86B (10 mg, 32.4%) as a solid, and Example 86C (7 mg, 22%) as a solid. Example 86B: LC-MS(ESI) m/z: 487.0/489.0[M+H]$^+$; $^1$H NMR (400 MHz, CDCl$_3$) δ 7.92-7.74 (m, 1H), 7.67-7.31 (m, 4H), 7.21-6.37 (m, 3H), 5.38 (t, J=8.6 Hz, 1H), 4.33-3.55 (m, 6H), 3.45-3.18 (m, 5H), 2.84-2.44 (m, 1H), 2.27-2.02 (m, 1H), 1.09 (d, J=3.1 Hz, 1H), 0.59 (d, J=7.5 Hz, 2H), 0.31 (br. s., 2H). Example 86C: LC-MS(ESI) m/z: 503.1[M+H]$^+$; $^1$H NMR (400 MHz, CDCl$_3$) δ 7.61 (d, J=7.9 Hz, 1H), 7.40 (br. s., 3H), 7.28-6.71 (m, 3H), 5.49-4.96 (m, 1H), 4.31-3.34 (m, 9H), 3.31-2.92 (m, 5H), 2.78-2.43 (m, 1H), 2.24-1.86 (m, 1H), 1.20-0.81 (m, 1H), 0.75-0.25 (m, 3H), 0.22-0.09 (m, 1H).

Example 86

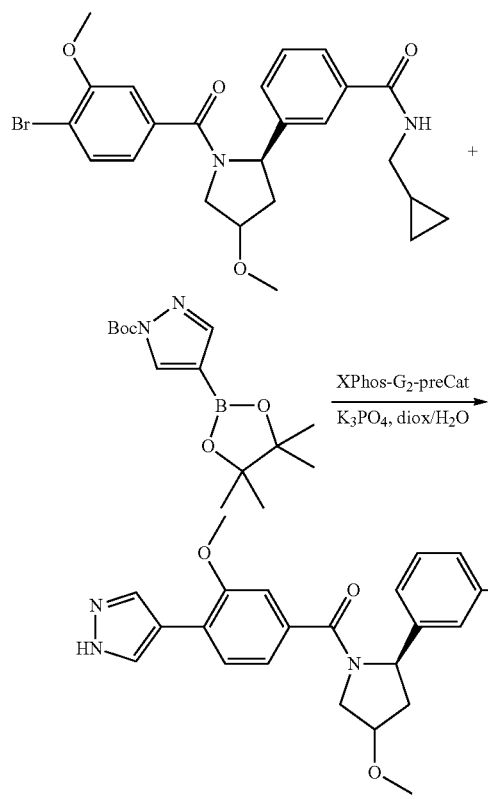

To a solution of Example 86B (10 mg, 0.021 mmol) in dioxane (1.5 mL) were added tert-butyl 4-(4,4,5,5-tetramethyl-1,3,2-dioxaborolan-2-yl)-1H-pyrazole-1-carboxylate (12.07 mg, 0.041 mmol), $K_3PO_4$ (0.3 mL, 0.300 mmol) and XPhos-G2-Pd-PreCat (1.614 mg, 2.052 μmol) at rt. The reaction was stirred under argon at 90° C. for 1.5 h. Solvent was removed. Purification by reverse chromatography afforded Example 86 (6.3 mg, 64.1%). LC-MS(ESI) m/z: 475.3[M+H]$^+$; $^1$H NMR (500 MHz, DMSO-$d_6$) δ 8.58 (br. s., 1H), 8.12 (s, 2H), 7.94-7.77 (m, 1H), 7.71 (t, J=6.9 Hz, 2H), 7.56 (d, J=7.4 Hz, 1H), 7.42 (t, J=7.4 Hz, 1H), 7.28-7.14 (m, 2H), 5.28-5.00 (m, 1H), 4.18-3.47 (m, 6H), 3.30-3.04 (m, 5H), 2.57 (d, J=7.4 Hz, 1H), 2.08-1.73 (m, 1H), 1.03 (br. s., 1H), 0.42 (d, J=7.4 Hz, 2H), 0.22 (d, J=4.0 Hz, 2H); Analytical HPLC RT=1.12 min (Method E), 1.16 min (Method F).

Example 87: N-(Cyclopropylmethyl)-3-[(2R)-4-methoxy-1-[3-methoxy-4-(1H-pyrazol-4-yl)benzoyl]pyrrolidin-2-yl]-N-methylbenzamide

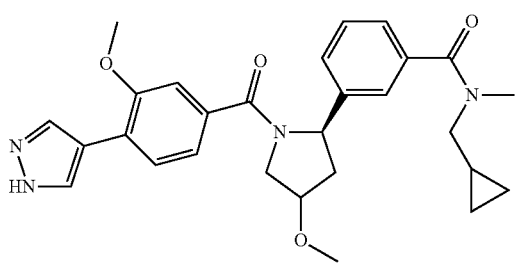 [SMILES: COc1cc(C(=O)N2CC(OC)C[C@@H]2c2cccc(C(=O)N(C)CC3CC3)c2)ccc1-c1cn[nH]c1]

Example 87 was prepared by following the same procedure as described in Example 86 by replacing Example 86B with 86C in 86D. LC-MS(ESI) m/z: 489.2[M+H]$^+$; $^1$H NMR (500 MHz, DMSO-$d_6$) δ 8.12 (br. s., 2H), 7.70 (d, J=7.4 Hz, 1H), 7.52-7.31 (m, 3H), 7.26-7.05 (m, 3H), 5.11 (br. s., 1H), 4.17-3.25 (m, 9H), 3.16 (s, 2H), 3.08-2.90 (m, 3H), 2.67-2.56 (m, 1H), 1.84 (br. s., 1H), 1.18-0.72 (m, 1H), 0.54-0.12 (m, 3H), -0.04 (br. s., 1H). Analytical HPLC RT=1.24 min (Method E), 1.25 min (Method F).

Example 88: N-(Cyclopropylmethyl)-3-[(2R,4R)-4-hydroxy-1-[3-methoxy-4-(1H-pyrazol-4-yl)benzoyl]-4-methylpyrrolidin-2-yl]benzamide

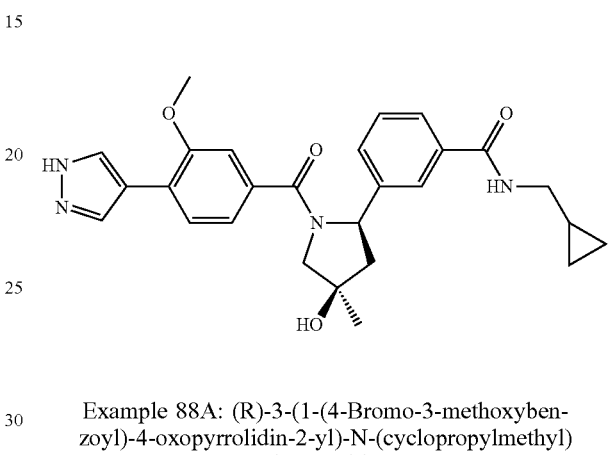

Example 88A: (R)-3-(1-(4-Bromo-3-methoxybenzoyl)-4-oxopyrrolidin-2-yl)-N-(cyclopropylmethyl)benzamide

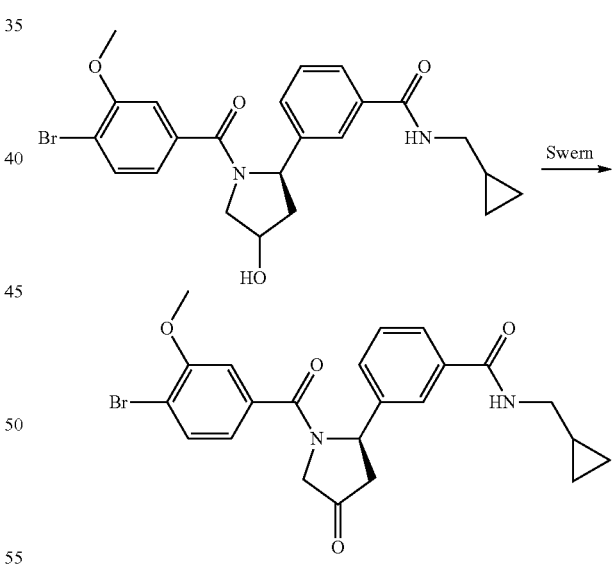

To a solution of oxalyl chloride (0.412 mL, 0.824 mmol) in DCM (5 mL) was added DMSO (0.117 mL, 1.648 mmol) at −78° C. The reaction was stirred under argon at −78° C. for 10 min. The solution of Example 86A (130 mg, 0.275 mmol) dissolved in DCM (2 mL). The reaction was stirred at −78° C. for 15 min and then at −50° C. for 30 min. The reaction was then treated with TEA (0.345 mL, 2.472 mmol) at the same temperature. The reaction was allowed to warm up to rt over 30 min. The reaction mixture was diluted with DCM, washed with sat $NH_4Cl$. The organic phase was dried over sodium sulfate, filtered and concentrated. Purification by normal phase chromatography afforded Example 88A as a light brown solid (97 mg, 74.9%). LC-MS(ESI) m/z: 471/473[M+H]+.

Example 88B: 3-((2R)-1-(4-Bromo-3-methoxybenzoyl)-4-hydroxy-4-methylpyrrolidin-2-yl)-N-(cyclopropylmethyl)benzamide

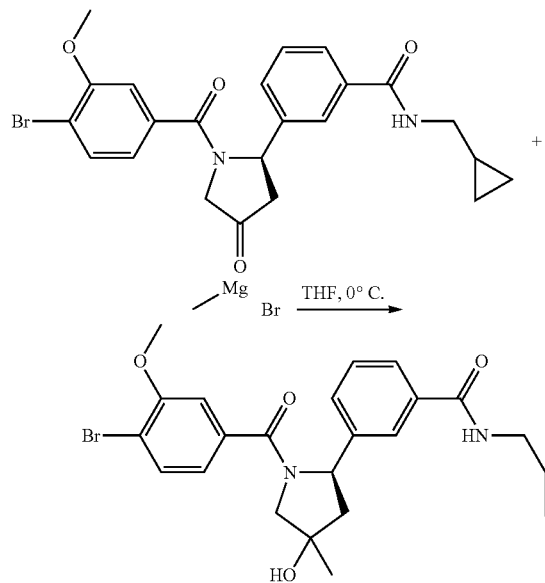

To a solution of Example 88A (62 mg, 0.132 mmol) in THF (4 mL) was added methylmagnesium bromide (3 M in ether, 0.110 ml, 0.330 mmol) at 0° C. The reaction was stirred under argon at 0° C. for 1 h. Another 1 eq of methylmagnesium bromide was added. After stirred at rt for 2 h. NH₄Cl solution was added to quench the reaction. Solvent was removed. Purification by reverse phase chromatography afforded Example 88B (8 mg, 12.48%). LC-MS (ESI) m/z: 487.0/489.0[M+H]+.

Example 88

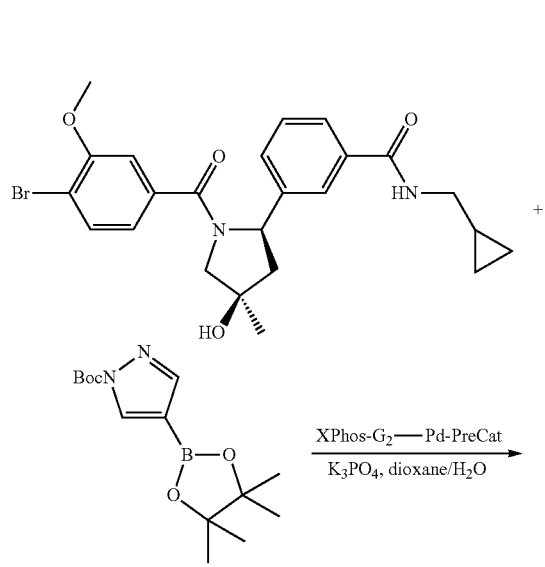

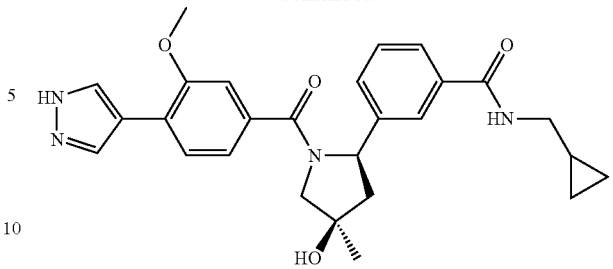

To a solution of Example 88B (8 mg, 0.016 mmol) in dioxane (1.5 mL) were added tert-butyl 4-(4,4,5,5-tetramethyl-1,3,2-dioxaborolan-2-yl)-1H-pyrazole-1-carboxylate (9.66 mg, 0.033 mmol), K₃PO₄ (1 M, 0.3 mL, 0.300 mmol) and XPhos-G2-Pd-PreCat (2.58 mg, 3.28 µmol) at rt. The reaction was stirred under argon at 60° C. for 1 h. Organic phase was separated and solvent was removed. To the residue was added DCM (1 mL) and TFA (0.5 mL), and it was stirred at rt for 30 min. The solvent was removed. Purification by reverse phase chromatography afforded Example 88 (1.5 mg, 18.68%). LC-MS(ESI) m/z: 475.2[M+H]+; ¹H NMR (500 MHz, DMSO-d₆) δ 8.59 (br. s., 1H), 8.02 (br. s., 4H), 7.83 (br. s., 1H), 7.69 (br. s., 2H), 7.54 (br. s., 1H), 7.41 (br. s., 1H), 5.13 (br. s., 1H), 3.89 (d, J=17.7 Hz, 2H), 3.69 (s, 3H), 3.16 (br. s., 2H), 2.36 (br. s., 1H), 1.90 (br. s., 1H), 1.20 (br. s., 3H), 1.03 (br. s., 1H), 0.41 (br. s., 2H), 0.21 (br. s., 2H); Analytical HPLC RT=1.11 min (Method E), 1.13 min (Method F).

Example 89: (5R)-5-(3-Methanesulfonylphenyl)-1-[3-methoxy-4-(1H-pyrazol-4-yl)benzoyl]pyrrolidin-3-yl acetate

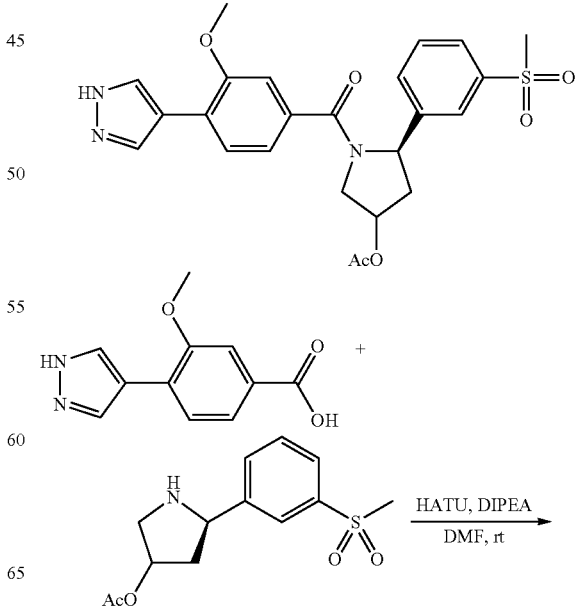

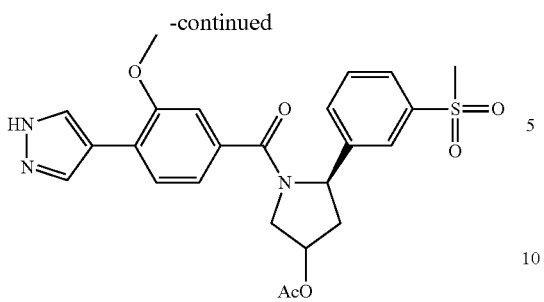

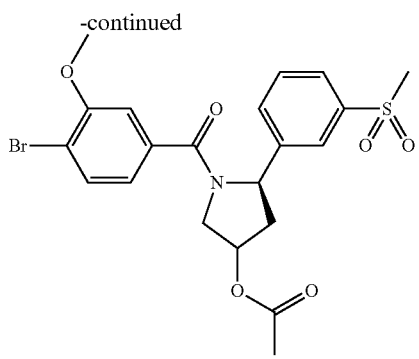

To a solution of Intermediate 1 (20 mg, 0.071 mmol) in DMF (1.5 mL) were added Intermediate 4 (20 mg, 0.071 mmol), DIPEA (0.062 mL, 0.353 mmol) and HATU (29.5 mg, 0.078 mmol) at rt. The reaction was stirred under argon at rt for 30 min. Purification by reverse phase chromatography afforded Example 89 (5.9 mg, 16.9%). LC-MS(ESI) m/z: 484.1[M+H]$^+$; $^1$H NMR (500 MHz, DMSO-d$_6$) δ 8.14 (br. s., 2H), 7.96 (d, J=4.4 Hz, 1H), 7.83 (br. s., 2H), 7.74 (d, J=7.7 Hz, 1H), 7.69-7.58 (m, 1H), 7.30-7.10 (m, 2H), 5.42-5.27 (m, 1H), 5.24 (br. s., 1H), 4.37 (d, J=10.1 Hz, 1H), 4.15-3.44 (m, 4H), 2.68-2.58 (m, 1H), 2.55 (s, 3H), 2.12 (br. s., 1H), 2.01 (s, 3H); Analytical HPLC RT=1.00 min (Method E), 1.05 min (Method F).

Example 90: (5R)-5-(3-Methanesulfonylphenyl)-1-[3-methoxy-4-(1H-pyrazol-4-yl)benzoyl]pyrrolidin-3-ol To a solution of Intermediate 4 (325 mg, 1.147 mmol) in DMF (10 mL) were added 4-bromo-3-methoxybenzoic acid (278 mg, 1.204 mmol), DIPEA (0.501 mL, 2.87 mmol) and HATU (480 mg, 1.262 mmol) at rt. The reaction was stirred under argon at rt for 2 h. The reaction mixture was diluted with EtOAc, washed with sat NaHCO$_3$ and brine. The organic phase was dried over sodium sulfate, filtered and concentrated. Purification by normal phase chromatography afforded Example 90A as a white solid (546 mg, 96%). LC-MS(ESI) m/z: 496.0/497.9[M+H]$^+$; $^1$H NMR (400 MHz, CD$_3$OD) δ 8.06-7.88 (m, 2H), 7.87-7.55 (m, 3H), 7.26-6.46 (m, 2H), 5.53-5.38 (m, 1H), 5.37-5.08 (m, 1H), 4.31-4.10 (m, 1H), 4.00-3.59 (m, 4H), 3.12 (s, 3H), 2.76-2.58 (m, 1H), 2.31-2.21 (m, 1H), 2.19-2.02 (m, 3H).

Example 90

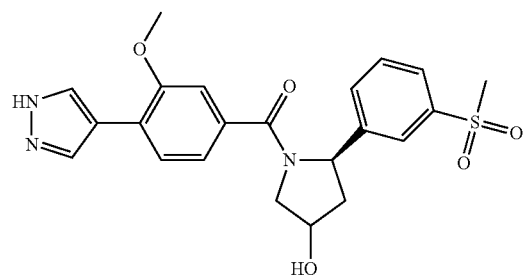 [SMILES: COc1cc(C(=O)N2CC(O)C[C@@H]2c2cccc(S(C)(=O)=O)c2)ccc1-c1cn[nH]c1]

Example 90A: (5R)-1-(4-Bromo-3-methoxybenzoyl)-5-(3-(methylsulfonyl)phenyl) pyrrolidin-3-yl acetate

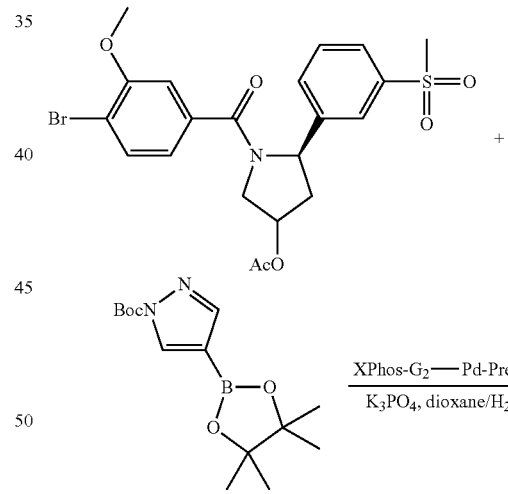

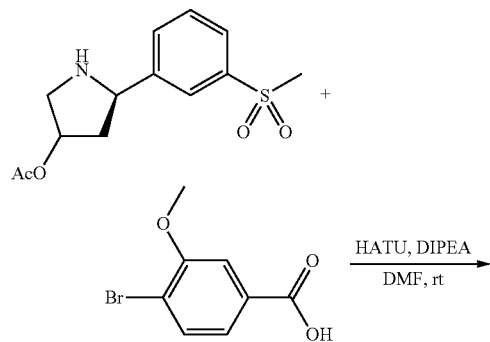

To a solution of Example 90A (28 mg, 0.056 mmol) in dioxane (2 mL) were added tert-butyl 4-(4,4,5,5-tetramethyl-1,3,2-dioxaborolan-2-yl)-1H-pyrazole-1-carboxylate (24.89 mg, 0.085 mmol), K₃PO₄ (0.282 mL, 0.282 mmol) and XPhos-G2-Pd-PreCat (4.44 mg, 5.64 µmol) at rt. The reaction was stirred under argon at 90° C. for 1 h. To the reaction was added 1.0 N NaOH solution, and the mixture was allowed to stir at 90° C. for 30 min. Solvent was removed. Purification by reverse phase chromatography afforded Example 90 (6.5 mg, 25.6%). LC-MS(ESI) m/z: 442.1 [M+H]⁺; ¹H NMR (500 MHz, DMSO-d₆) δ 8.13 (s, 2H), 7.98-7.88 (m, 1H), 7.79 (d, J=6.4 Hz, 2H), 7.73 (d, J=7.7 Hz, 1H), 7.67-7.56 (m, 1H), 7.29-7.12 (m, 2H), 5.37-5.16 (m, 1H), 4.31 (br. s., 1H), 4.19-3.59 (m, 5H), 3.28-2.97 (m, 3H), 2.41 (dd, J=13.1, 7.1 Hz, 1H), 1.89 (t, J=9.6 Hz, 1H); Analytical HPLC RT=0.72 min (Method E), 0.77 min (Method F).

Example 91: (5R)-5-(2-Fluorophenyl)-1-[3-methoxy-4-(1H-pyrazol-4-yl)benzoyl] pyrrolidin-3-yl acetate

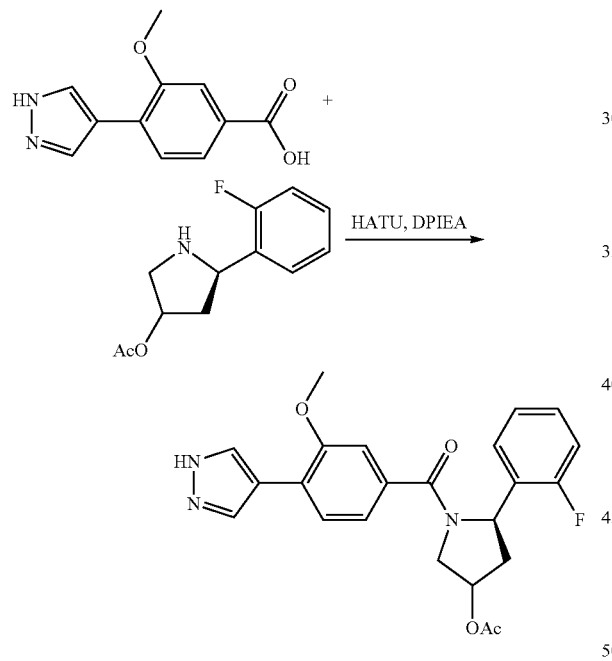

To a solution of Intermediate 5 (45 mg, 0.202 mmol) in DMF were added Intermediate 1 (44.0 mg, 0.202 mmol), DIPEA (106 µl, 0.605 mmol) and HATU (77 mg, 0.202 mmol) at rt. The reaction was stirred under argon at rt for 1 h. Purification by reverse phase chromatography afforded Example 91 (79.8 mg, 90% yield). LC-MS(ESI) m/z: 424.2 [M+H]⁺; ¹H NMR (500 MHz, DMSO-d₆) δ 8.69 (d, J=3.7 Hz, 1H), 8.47 (d, J=8.1 Hz, 1H), 8.12 (br. s., 2H), 7.78-7.51 (m, 1H), 7.46 (dd, J=8.2, 4.2 Hz, 1H), 7.37-7.10 (m, 3H), 5.41 (t, J=8.6 Hz, 1H), 4.28 (d, J=8.8 Hz, 1H), 3.97-3.58 (m, 4H), 3.45 (br. s., 1H), 2.80-2.64 (m, 1H), 2.55 (s, 3H), 2.17-2.04 (m, 1H). Analytical HPLC RT=1.30 min (Method E), 1.36 min (Method F).

Example 92: (3R,5R)-5-(2-Fluorophenyl)-1-[3-methoxy-4-(1H-pyrazol-4-yl)benzoyl] pyrrolidin-3-ol, and Example 93: (3S,5R)-5-(2-Fluorophenyl)-1-[3-methoxy-4-(1H-pyrazol-4-yl)benzoyl] pyrrolidin-3-ol

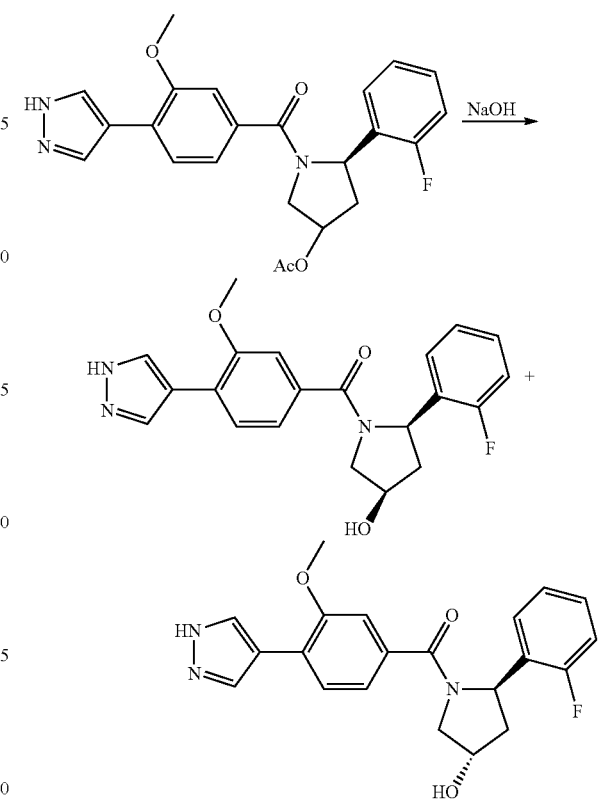

To a solution of Example 91 (50.8 mg, 0.12 mmol) in DMF (1.5 mL) was added sodium hydroxide (0.4 mL, 0.400 mmol) at rt. The reaction was stirred under argon at 50° C. for 30 min. Purification by reverse phase chromatography afforded Example 92 (19.9 mg, 43.5 5) and Example 93 (5.1 mg 11.0%).

Example 92

LC-MS(ESI) m/z: 382.1[M+H]⁺; ¹H NMR (500 MHz, DMSO-d₆) δ 8.12 (br. s., 2H), 7.72 (d, J=7.7 Hz, 1H), 7.56-7.42 (m, 1H), 7.33-7.03 (m, 5H), 5.49-5.22 (m, 1H), 4.44-4.23 (m, 1H), 4.04 (d, J=8.8 Hz, 1H), 3.93 (s, 3H), 3.63-3.45 (m, 1H), 2.37 (dd, J=12.8, 7.7 Hz, 1H), 2.05-1.73 (m, 1H); Analytical HPLC RT=1.00 min (Method E), 1.07 min (Method F).

Example 93

LC-MS(ESI) m/z: 382.2[M+H]⁺; ¹H NMR (500 MHz, DMSO-d₆) δ 8.13 (s, 2H), 7.72 (d, J=7.7 Hz, 1H), 7.50 (d, J=7.1 Hz, 1H), 7.33-7.08 (m, 5H), 5.40-5.09 (m, 1H), 4.52-4.17 (m, 1H), 4.10-3.85 (m, 3H), 3.79-3.40 (m, 2H), 2.60 (br. s., 1H), 1.73 (br. s., 1H); Analytical HPLC RT=0.97 min (Method E), 1.00 min (Method F).

Example 94: (3R,5R)-1-[3-(Difluoromethoxy)-4-(1H-pyrazol-4-yl)benzoyl]-5-(2-fluorophenyl)pyrrolidin-3-ol, and Example 95: (3S,5R)-1-[3-(Difluoromethoxy)-4-(1H-pyrazol-4-yl)benzoyl]-5-(2-fluorophenyl)pyrrolidin-3-ol Example 96: 5-[(2R,4R)-2-(2-Fluorophenyl)-4-hydroxypyrrolidine-1-carbonyl]-2-(1H-pyrazol-4-yl)benzonitrile, and Example 97: 5-[(2R)-2-(2-Fluorophenyl)-4-hydroxypyrrolidine-1-carbonyl]-2-(1H-pyrazol-4-yl)benzonitrile

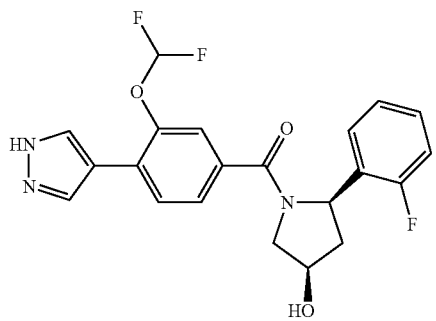

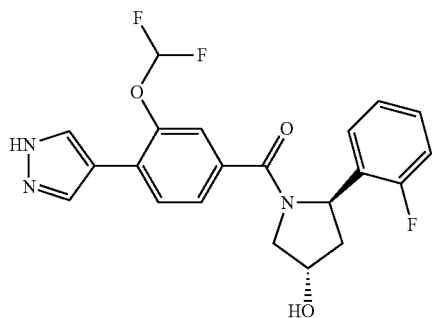

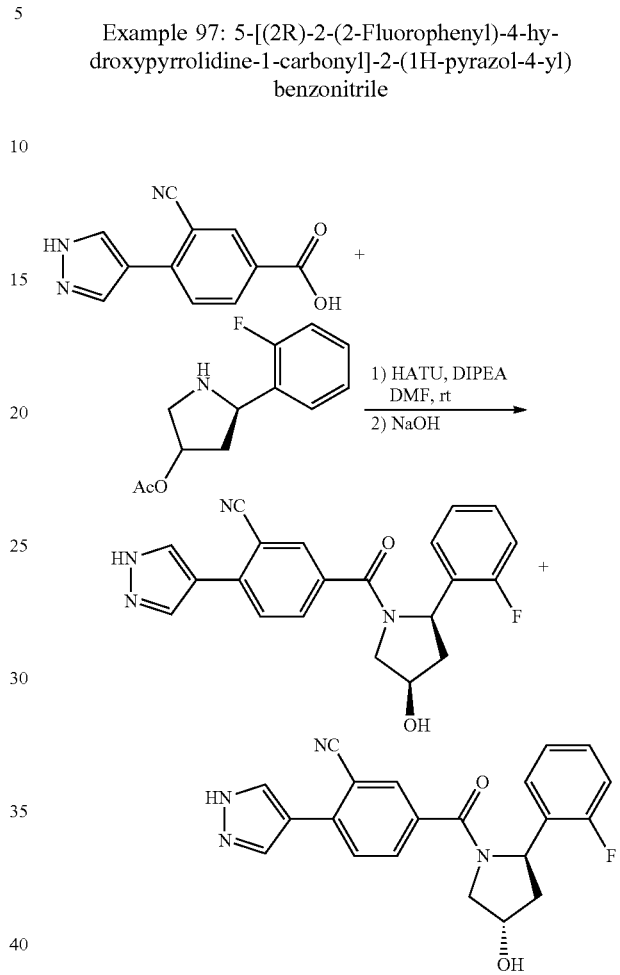

Examples 94 and 95 were prepared by following the similar procedure as described in Example 93, by replacing Intermediate 1 with Intermediate 6.

Examples 96 and 97 were prepared by following the similar procedure as described in Example 92 by replacing Intermediate 6 with Intermediate 7.

Example 94

LC-MS(ESI) m/z: 418.2[M+H]$^+$; $^1$H NMR (500 MHz, DMSO-d$_6$) δ 8.12 (br. s., 2H), 7.84 (d, J=8.1 Hz, 1H), 7.52 (d, J=8.1 Hz, 1H), 7.46 (d, J=5.7 Hz, 1H), 7.45-7.40 (m, 1H), 7.33-7.07 (m, 4H), 5.39 (t, J=8.8 Hz, 1H), 4.48-4.26 (m, 1H), 4.03 (d, J=8.4 Hz, 1H), 3.46 (d, J=11.1 Hz, 1H), 2.36 (dd, J=13.0, 7.2 Hz, 1H), 1.96-1.82 (m, 1H); Analytical HPLC RT=1.30 min (Method E), 1.30 min (Method F).

Example 96

LC-MS(ESI) m/z: 377.1 [M+H]$^+$; $^1$H NMR (500 MHz, DMSO-d$_6$) δ 8.44-8.24 (m, 1H), 8.18-8.07 (m, 2H), 7.94-7.82 (m, 2H), 7.55 (t, J=6.9 Hz, 1H), 7.34-7.25 (m, 1H), 7.22-7.11 (m, 2H), 5.48-5.33 (m, 1H), 5.30-5.10 (m, 1H), 4.47-4.25 (m, 1H), 4.08 (d, J=8.4 Hz, 1H), 3.41 (d, J=10.8 Hz, 1H), 2.44-2.29 (m, 1H), 2.03-1.76 (m, 1H); Analytical HPLC RT=1.03 min (Method E), 1.03 min (Method F).

Example 95

LC-MS(ESI) m/z: 418.1[M+H]$^+$; $^1$H NMR (500 MHz, DMSO-d$_6$) δ 8.12 (br. s., 2H), 7.85 (d, J=7.7 Hz, 1H), 7.59-7.32 (m, 3H), 7.31-6.87 (m, 4H), 5.39-5.13 (m, 1H), 4.51-4.22 (m, 1H), 3.78-3.69 (m, 1H), 3.68-3.58 (m, 1H), 2.67-2.57 (m, 1H), 1.87-1.67 (m, 1H); Analytical HPLC RT=1.12 min (Method E), 1.13 min (Method F).

Example 97

LC-MS(ESI) m/z: 377.2[M+H]$^+$; $^1$H NMR (500 MHz, DMSO-d$_6$) δ 8.50-8.23 (m, 1H), 8.12 (s, 1H), 7.93-7.80 (m, 1H), 7.63-7.02 (m, 6H), 5.35-5.21 (m, 1H), 4.65-4.43 (m, 1H), 4.42-4.21 (m, 1H), 3.69 (d, J=6.4 Hz, 1H), 2.68-2.57 (m, 1H), 2.29 (dd, J=13.8, 6.4 Hz, 1H); Analytical HPLC RT=0.99 min (Method E), 0.99 min (Method F).

Example 98: (3R,5R)-5-(2-Fluorophenyl)-1-[2-methoxy-4-(1H-pyrazol-4-yl)benzoyl] pyrrolidin-3-ol

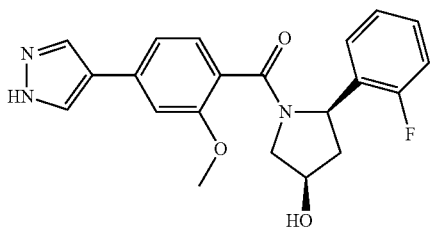 [SMILES: COc1cc(-c2cn[nH]c2)ccc1C(=O)N1C[C@H](O)C[C@@H]1c1ccccc1F]

Example 98 was prepared by following a similar procedure as described in Example 93, by replacing Intermediate 1 with Intermediate 2.

Example 98

LC-MS(ESI) m/z: 382.35[M+H]$^+$; $^1$H NMR (500 MHz, DMSO-d$_6$) δ 8.50-7.94 (m, 2H), 7.49 (t, J=7.6 Hz, 1H), 7.40-7.13 (m, 5H), 7.12-6.82 (m, 1H), 5.43 (t, J=8.1 Hz, 1H), 5.26-5.09 (m, 1H), 4.54-4.23 (m, 1H), 4.02 (s, 2H), 3.89-3.64 (m, 2H), 3.25 (d, J=11.0 Hz, 1H), 2.50-2.28 (m, 1H), 2.03-1.85 (m, 1H); Analytical HPLC RT=1.14 min (Method E), 1.16 min (Method F).

Example 100: 1-{5-[2-(3-Methoxyphenyl)pyrrolidine-1-carbonyl]-2-(1H-pyrazol-4-yl)phenyl}ethan-1-ol

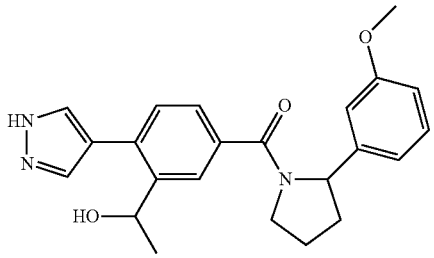 [SMILES: COc1cccc(C2CCCN2C(=O)c2ccc(-c3cn[nH]c3)c(C(C)O)c2)c1]

Example 100A: (4-Bromo-3-(1,3-dioxolan-2-yl)phenyl)(2-(3-methoxyphenyl)pyrrolidin-1-yl)methanone

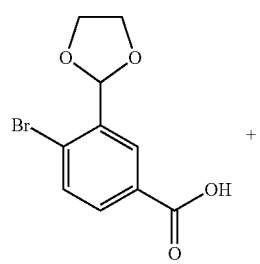

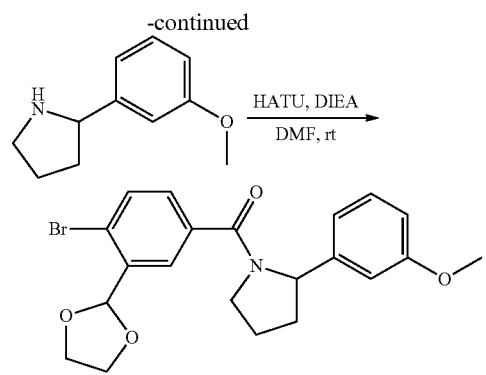

To a solution of 4-bromo-3-(1,3-dioxolan-2-yl)benzoic acid (120 mg, 0.439 mmol) in DMF (2 mL) were added 2-(3-methoxyphenyl)pyrrolidine (78 mg, 0.439 mmol), DIEA (0.230 mL, 1.318 mmol) and HATU (184 mg, 0.483 mmol) at rt. The reaction was stirred under argon at rt for 1 h. The reaction was diluted with EtOAc, washed with water and brine, dried over Na$_2$SO$_4$. Normal phase purification afforded Example 100A as a tan oil (180 mg, 95%). LC-MS (ESI) m/z: 431.9/433.9 [M+H]$^+$.

Example 100B: (3-(1,3-Dioxolan-2-yl)-4-(1H-pyrazol-4-yl)phenyl)(2-(3-methoxyphenyl) pyrrolidin-1-yl)methanone

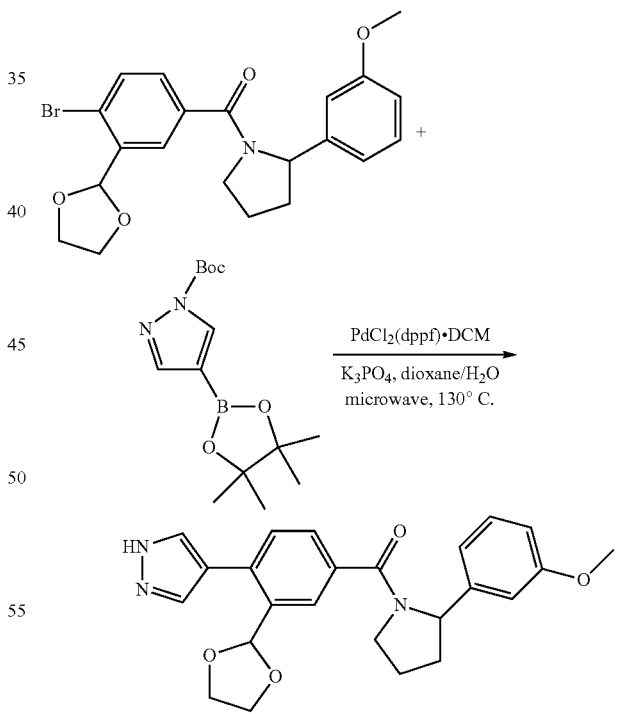

To a solution of Example 100A (165 mg, 0.382 mmol) in dioxane (3 mL) were added tert-butyl 4-(4,4,5,5-tetramethyl-1,3,2-dioxaborolan-2-yl)-1H-pyrazole-1-carboxylate (189 mg, 0.611 mmol), K$_3$PO$_4$ (186 mg, 0.878 mmol), PdCl$_2$(dppf) (31.2 mg, 0.038 mmol) and water (0.600 mL). The reaction was heated with microwave at 130° C. for 15 min. Solvent was removed, and normal phase purification afforded 100B as a white foam of solid (121 mg, 76%). LC-MS(ESI) m/z: 420.0 [M+H]+; 1H NMR (400 MHz, CDCl3) δ 8.10-6.70 (m, 9H), 5.85-5.70 (m, 1H), 4.25-3.55 (m, 10H), 2.45-1.75 (m, 4H).

Example 100C: 5-(2-(3-Methoxyphenyl)pyrrolidine-1-carbonyl)-2-(1H-pyrazol-4-yl)benzaldehyde

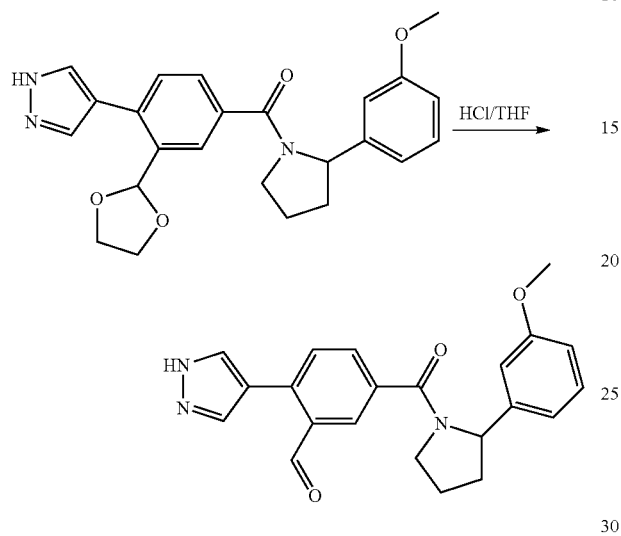

To a solution of Example 100B (121 mg, 0.288 mmol) in THF (5 mL) was added conc. HCl (0.494 mL, 3.46 mmol) at rt. The reaction was stirred under argon at rt for 2 h. The solvent was removed. The residue was dissolved in EtOAc, washed with 1.5 M aq. K2HPO4 and brine, dried over Na2SO4, concentrated and dried to afford Example 100C as foam of solid (92 mg, 85%). LC-MS(ESI) m/z: 376.0 [M+H]+; 1H NMR (400 MHz, CDCl3) δ 10.24-10.07 (m, 1H), 7.90-6.52 (m, 9H), 4.05-3.63 (m, 6H), 2.49-1.88 (m, 4H).

Example 100

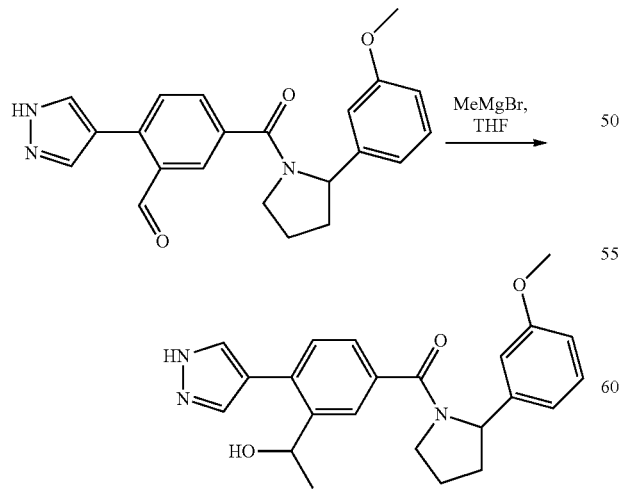

To a solution of Example 100C (87 mg, 0.232 mmol) in THF (4 mL) was added a solution of methylmagnesium bromide (3.0 M in diethyl ether, 0.541 mL, 1.622 mmol) in at 0° C. dropwise. The reaction was stirred under argon for 40 min, and then was quenched with MeOH/aq. NH4Cl. The solvents were removed. Reverse phase chromatography purification afforded Example 100. LC-MS(ESI) m/z: 392.5 [M+H]+; 1H NMR (500 MHz, DMSO-d6) δ 7.91-6.57 (m, 9H), 5.18-4.95 (m, 2H), 3.87-3.78 (m, 1H), 3.75 (s, 3H), 3.67 (br. s., 1H), 2.37 (d, J=6.4 Hz, 1H), 1.97-1.66 (m, 4H), 1.33 (d, J=6.1 Hz, 3H); Analytical HPLC RT=1.21 min (Method E), 1.20 min (Method F).

Example 101: (5R)-1-[3-Ethyl-4-(1H-pyrazol-4-yl)benzoyl]-5-(2-fluorophenyl) pyrrolidin-3-ol

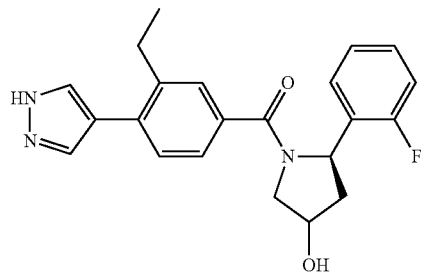

Example 101A: (5R)-1-(4-Chloro-3-ethylbenzoyl)-5-(2-fluorophenyl)pyrrolidin-3-yl acetate

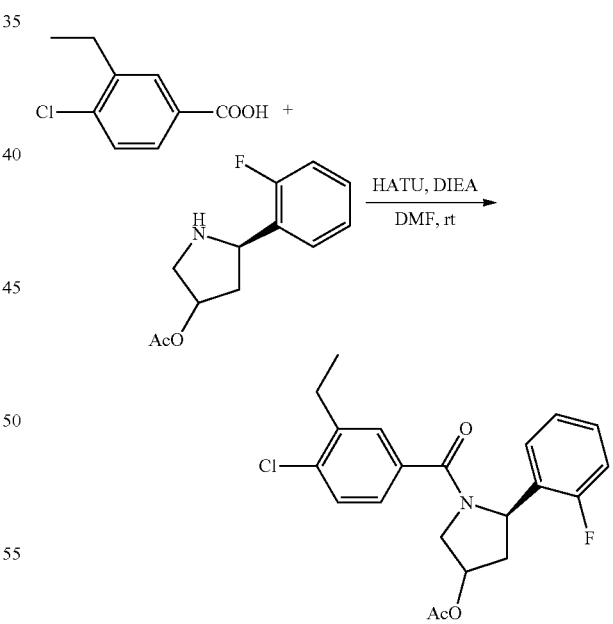

To a solution of Intermediate 5 (310 mg, 1.389 mmol) in DCM (3 mL) were added 4-chloro-3-ethylbenzoic acid (256 mg, 1.389 mmol), DIEA (0.606 mL, 3.47 mmol) and HATU (581 mg, 1.527 mmol) at rt. The reaction was stirred under argon at rt for 2 h. Purification by normal phase chromatography afforded Example 101A as a white solid (390 mg, 72.0%). LCMS(ESI) m/z: 390.1 [M+H]+; 1H NMR (400 MHz, CDCl3) δ 7.55-7.31 (m, 3H), 7.28-6.83 (m, 4H), 5.48-5.29 (m, 1H), 5.61-5.15 (m, 1H), 4.24-4.00 (m, 1H), 3.74 (d, J=12.3 Hz, 1H), 2.87-2.23 (m, 4H), 2.16 and 2.06 (s, 3H), 1.30-0.99 (m, 3H).

Example 101

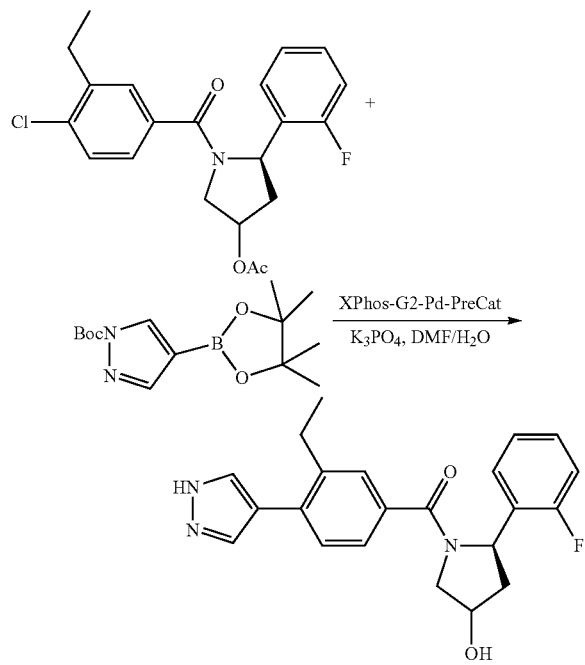

To a solution of Example 101A (33 mg, 0.085 mmol) in DMF (1.5 mL) and water (0.5 mL) were added tert-butyl 4-(4,4,5,5-tetramethyl-1,3,2-dioxaborolan-2-yl)-1H-pyrazole-1-carboxylate (37.3 mg, 0.127 mmol), $K_3PO_4$ (53.9 mg, 0.254 mmol) and XPhos-G2-PreCat (3.33 mg, 4.23 µmol) at rt. The reaction was stirred under argon at 90° C. for 1 h. The reaction was cooled to rt, and 0.5 mL NaOH (1 N) was added. After stirred at rt for 30 min, it was acidified with TFA. Purification by reverse phase chromatography afforded Example 101 (9.6 mg, 29.6%). LC-MS(ESI) m/z: 380.00[M+H]$^+$; $^1$H NMR (500 MHz, DMSO-d$_6$) δ 8.17-7.57 (m, 2H), 7.53-6.98 (m, 7H), 5.41 (t, J=8.7 Hz, 1H), 5.28-5.06 (m, 1H), 4.47-4.21 (m, 1H), 4.08-3.76 (m, 1H), 3.45 (d, J=11.3 Hz, 1H), 2.76 (q, J=7.5 Hz, 2H), 2.37 (dd, J=12.5, 7.9 Hz, 1H), 2.02-1.77 (m, 1H), 1.15 (t, J=7.5 Hz, 3H); Analytical HPLC RT=1.26 min (Method E), 1.31 min (Method F).

Example 102: 4-(4-{2-[3-(2,2-Difluoroethoxy)phenyl]pyrrolidine-1-carbonyl}-2-methoxyphenyl)-1H-pyrazole

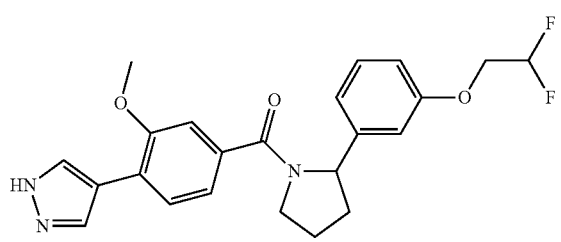 [SMILES: COc1cc(C(=O)N2CCCC2c2cccc(OCC(F)F)c2)ccc1-c1cn[nH]c1]

Example 102A: 3-(Pyrrolidin-2-yl)phenol

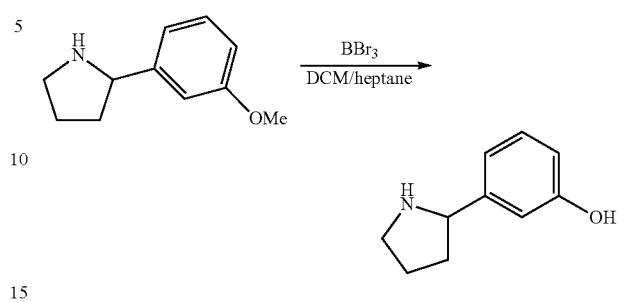

To a solution of 2-(3-methoxyphenyl)pyrrolidine (220 mg, 1.241 mmol) in DCM (5 mL) was added BBr$_3$ (1 M in heptane, 1.241 ml, 1.241 mmol) at 0° C. The reaction was stirred under argon at 0° C. for 1 h, and then it was warmed to rt. A tar solid formed. After sitting at rt for 2 h, MeOH was added to quench the reaction. The solvent was removed to afford Example 102A as foam of solid (200 mg, 100%). LC-MS(ESI) m/z: 164.0[M+H]$^+$.

Example 102B: (4-Bromo-3-methoxyphenyl)(2-(3-hydroxyphenyl)pyrrolidin-1-yl)methanone

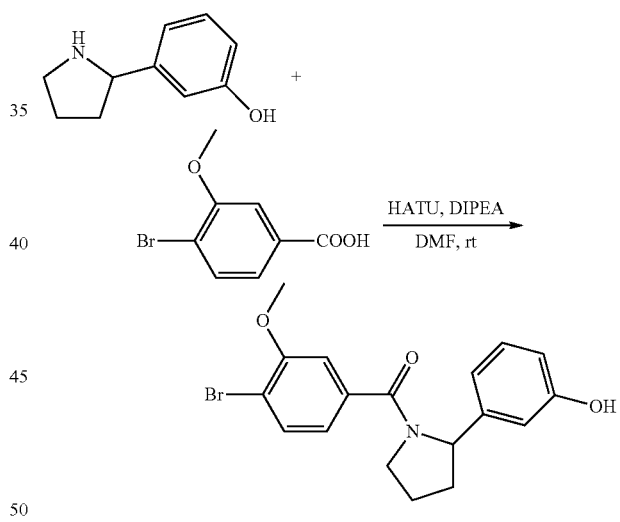

To a solution of Example 102A (180 mg, 1.1 mmol) in DMF (5 mL) were added 4-bromo-3-methoxybenzoic acid (254 mg, 1.10 mmol), DIPEA (0.576 mL, 3.30 mmol) and HATU (418 mg, 1.10 mmol) at rt. The reaction was stirred under argon at rt for 2 h. The reaction mixture was diluted with EtOAc, washed with 1M HCl, H$_2$O and brine. The organic phase was dried over sodium sulfate, filtered and concentrated. The crude product was purified by normal phase chromatography to afford Example 102B as a white solid (405 mg, 98%). LC-MS(ESI) m/z: 376.0/378.0[M+H]$^+$; $^1$H NMR (400 MHz, CDCl$_3$) δ 8.73-7.75 (m, 1H), 7.51-7.33 (m, 1H), 7.17-6.42 (m, 6H), 5.36-4.68 (m, 1H), 4.02-3.14 (m, 5H), 2.45-2.11 (m, 1H), 2.01-1.73 (m, 3H).

Example 102C: (4-Bromo-3-methoxyphenyl)(2-(3-(2,2-difluoroethoxy)phenyl) pyrrolidin-1-yl)methanone

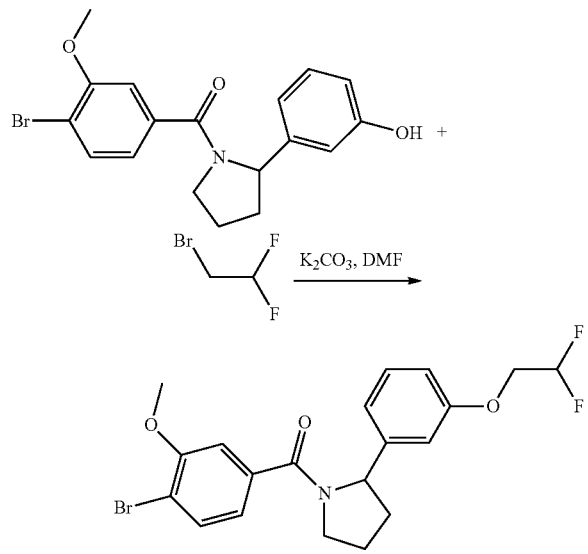

To a solution of Example 102B (20 mg, 0.053 mmol) in DMF (1 mL) were added K₂CO₃ (22.04 mg, 0.159 mmol) and 2-bromo-1,1-difluoroethane (23.11 mg, 0.159 mmol) at rt. The reaction was stirred under argon at 60° C. overnight. The reaction mixture was used in the next step without purification. LC-MS(ESI) m/z: 442.0[M+H]⁺.

Example 102

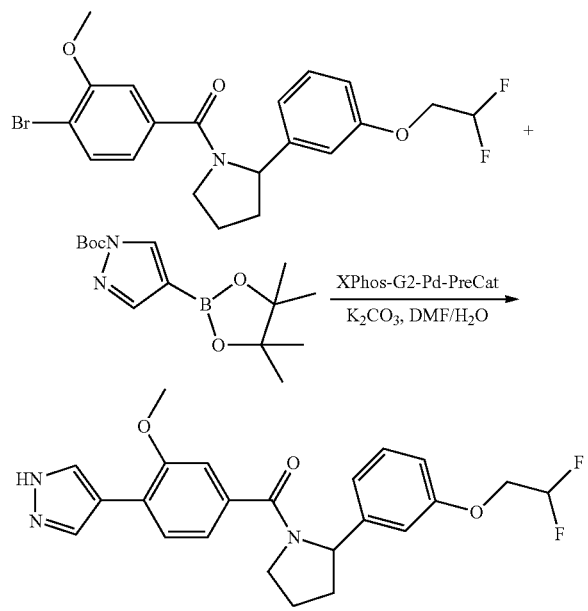

To the reaction solution of Example 102C in DMF (1 mL) were added water (0.3 mL), tert-butyl 4-(4,4,5,5-tetramethyl-1,3,2-dioxaborolan-2-yl)-1H-pyrazole-1-carboxylate (23.39 mg, 0.080 mmol) and XPhos-G2-Pd-PreCat (2.085 mg, 2.65 μmol) at rt. The reaction was stirred at 90° C. for 1 h. Purification by reverse phase chromatography afforded Example 102 (11.2 mg, 48.9%). LC-MS(ESI) m/z: 428.15 [M+H]⁺; ¹H NMR (500 MHz, DMSO-d₆) δ 8.23-7.96 (m, 2H), 7.78-7.46 (m, 1H), 7.37-7.11 (m, 2H), 7.03-6.65 (m, 4H), 6.54-6.15 (m, 1H), 5.24-4.83 (m, 1H), 4.48-4.11 (m, 2H), 4.01-3.42 (m, 5H), 2.43-2.21 (m, 1H), 1.80 (br. s., 3H); Analytical HPLC RT=1.54 min (Method E), 1.57 min (Method F).

Example 103: 3-(3-{1-[3-Methoxy-4-(1H-pyrazol-4-yl)benzoyl]pyrrolidin-2-yl}phenoxymethyl)-5-methyl-1,2-oxazole

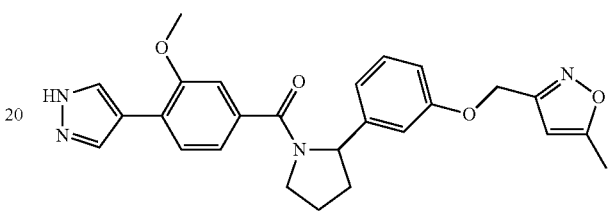

Example 103 was prepared by following a similar procedure as described in Example 103 by replacing 2-bromo-1,1-difluoroethane with 3-(bromomethyl)-5-methylisoxazole in Example 102A. LC-MS(ESI) m/z: 459.1 [M+H]⁺; ¹H NMR (500 MHz, DMSO-d₆) δ 8.33-7.87 (m, 2H), 7.80-7.45 (m, 1H), 7.31-7.09 (m, 2H), 7.02-6.58 (m, 4H), 6.39-6.15 (m, 1H), 5.26-4.82 (m, 3H), 4.02-3.65 (m, 2H), 3.50 (br. s., 3H), 2.38 (d, J=5.0 Hz, 3H), 2.34-2.17 (m, 1H), 1.97-1.61 (m, 3H).

Example 104: 4-(3-{1-[3-Methoxy-4-(1H-pyrazol-4-yl)benzoyl]pyrrolidin-2-yl}phenoxy)-1-methylpiperidine

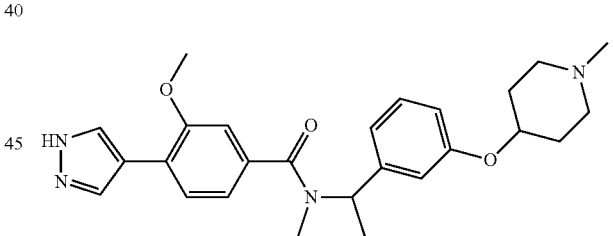

Example 104A: tert-Butyl 4-(3-(1-(4-bromo-3-methoxybenzoyl)pyrrolidin-2-yl)phenoxy)piperidine-1-carboxylate

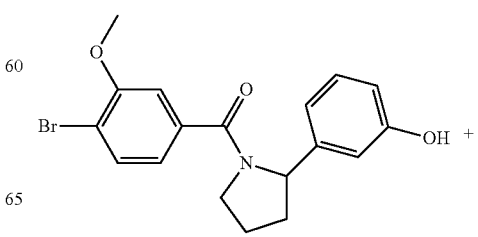

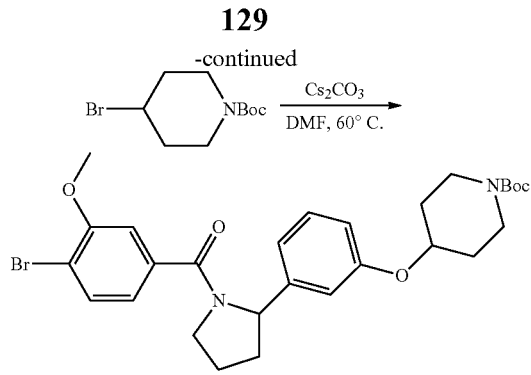

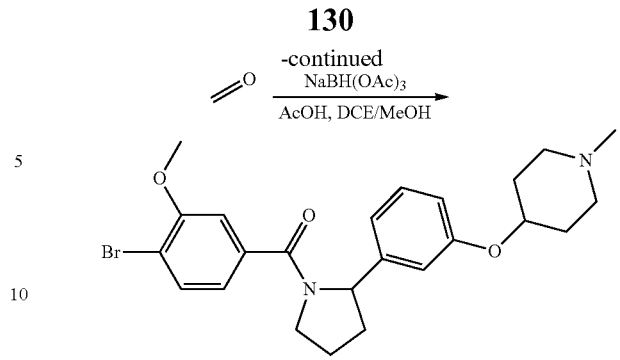

To a solution of Example 102B (22 mg, 0.058 mmol) in DMF (1.5 mL) were added Cs$_2$CO$_3$ (57.2 mg, 0.175 mmol) and 1-Boc-4-bromopiperidine (30.9 mg, 0.117 mmol) at rt. The reaction was stirred under argon at 90° C. overnight. The solvent was removed. The crude product was purified by normal phase chromatography to afford Example 104A (17 mg, 52%). LC-MS(ESI) m/z: 559.1/561.1[M+H]$^+$.

Example 104B: (4-Bromo-3-methoxyphenyl)(2-(3-(piperidin-4-yloxy)phenyl)pyrrolidin-1-yl)methanone

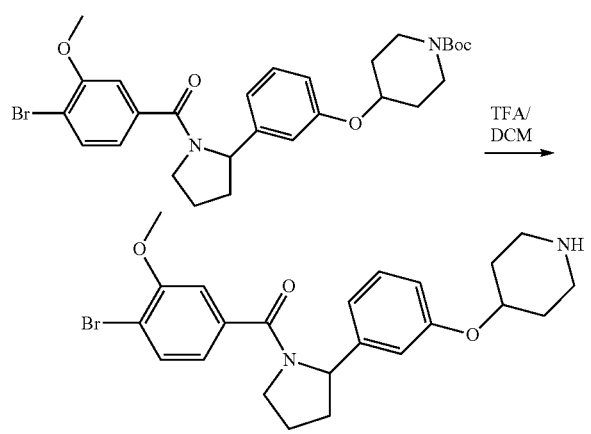

To a solution of Example 104A (17 mg, 0.030 mmol) in DCM (1 mL) was added TFA (0.5 mL) at rt. The reaction was stirred under N$_2$ at rt for 30 min. The solvent was removed. The crude product was used in the next step without further purification. LC-MS(ESI) m/z: 459.1/461.1 [M+H]$^+$.

Example 104C: (4-Bromo-3-methoxyphenyl)(2-(3-((1-methylpiperidin-4-yl)oxy)phenyl) pyrrolidin-1-yl)methanone

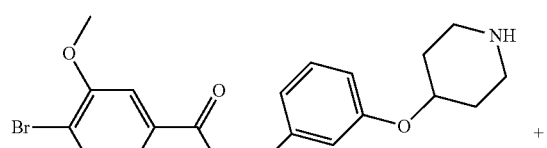

To a solution of Example 104B (13 mg, 0.028 mmol) in DCE/MeOH (1:1, 2 mL) were added paraformaldehyde (8.50 mg, 0.283 mmol), a drop of AcOH and NaBH(OAc)$_3$ (17.99 mg, 0.085 mmol) at rt. The reaction was stirred under N$_2$ at rt for overnight. The solvent was removed. The crude product was purified by reverse phase chromatography to afford Example 104C (12.3 mg, 74.0%). LC-MS(ESI) m/z: 473.1/475.1[M+H]$^+$; $^1$H NMR (400 MHz, CD$_3$OD) δ 7.68-7.39 (m, 1H), 7.33-7.08 (m, 2H), 7.03-6.70 (m, 3H), 6.64-6.48 (m, 1H), 5.16-4.42 (m, 2H), 4.00-3.77 (m, 3H), 3.70-3.53 (m, 1H), 3.52-3.33 (m, 4H), 3.15 (t, J=11.6 Hz, 1H), 2.91 (d, J=2.4 Hz, 3H), 2.55-1.76 (m, 8H).

Example 104

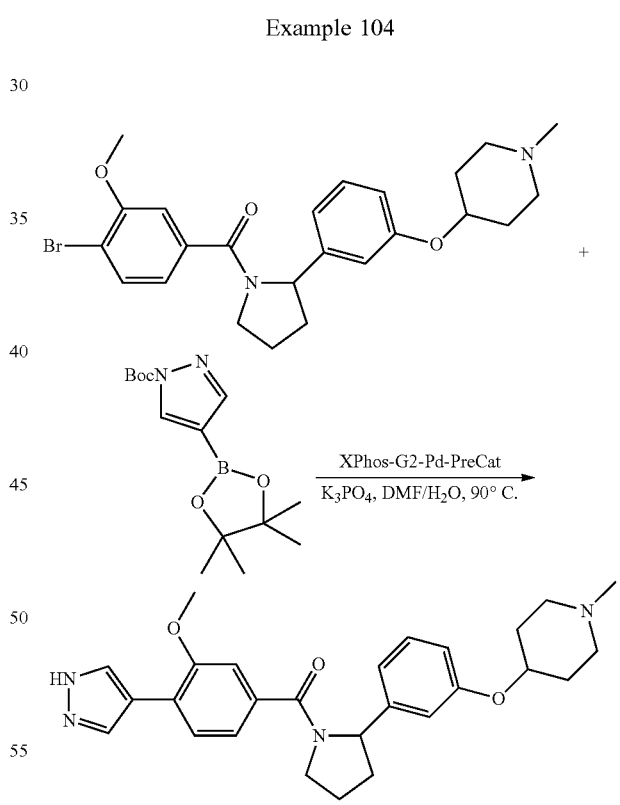

To a solution of Example 104C (13 mg, 0.022 mmol) in DMF (1 mL) were added tert-butyl 4-(4,4,5,5-tetramethyl-1,3,2-dioxaborolan-2-yl)-1H-pyrazole-1-carboxylate (13.02 mg, 0.044 mmol), K$_3$PO$_4$ (4.70 mg, 0.022 mmol), water (0.3 mL) and XPhos-G2-Pd-PreCat (1.741 mg, 2.213 μmol) at rt. The reaction was stirred under N$_2$ at 90° C. for 1 h. The reaction was acidified with TFA. Purification by reverse phase chromatography afforded Example 104 (6.3 mg, 60.6%). LC-MS(ESI) m/z: 461.30[M+H]$^+$; $^1$H NMR (500

MHz, DMSO-d$_6$) δ 8.25-7.95 (m, 2H), 7.80 (s, 1H), 7.74-7.44 (m, 1H), 7.30-7.13 (m, 2H), 6.96-6.54 (m, 4H), 5.23-4.83 (m, 1H), 4.52-4.16 (m, 1H), 4.02-3.37 (m, 5H), 2.68 (br. s., 1H), 2.43-2.10 (m, 6H), 1.92-1.48 (m, 7H); Analytical HPLC RT=1.13 min (Method E), 1.15 min (Method F).

Example 105: N-(3-{1-[3-Methoxy-4-(1H-pyrazol-4-yl)benzoyl]pyrrolidin-2-yl}phenyl)-1-methylpiperidin-4-amine

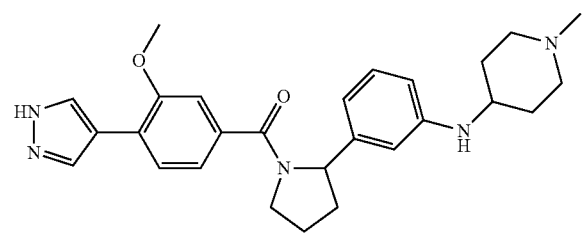 [SMILES: COc1cc(C(=O)N2CCCC2c2cccc(NC3CCN(C)CC3)c2)ccc1-c1cn[nH]c1]

Example 105A: tert-Butyl 2-(3-((1-methylpiperidin-4-yl)amino)phenyl)pyrrolidine-1-carboxylate

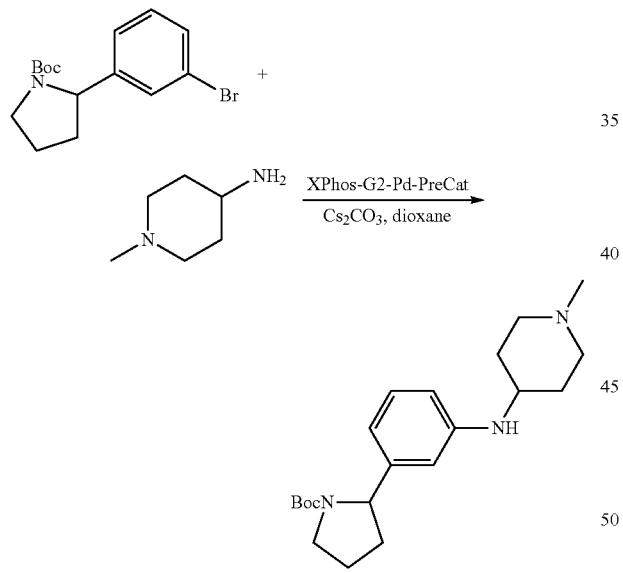

To a solution of Example 71A (20 mg, 0.061 mmol) in dioxane (1.5 mL) were added 1-methylpiperidin-4-amine (14.00 mg, 0.123 mmol), Cs$_2$CO$_3$ (59.9 mg, 0.184 mmol) and XPhos-G2-Pd-PreCat (4.82 mg, 6.13 μmol) at rt. The reaction was purged with argon, and then was stirred under argon at 100° C. for 4 h. The solvent was removed. The crude product was purified by reverse phase chromatography to afford Example 105A as a solid (14 mg, 38.9%). LC-MS(ESI) m/z: 360.2[M+H]$^+$; $^1$H NMR (400 MHz, CD$_3$OD) δ 7.41-7.05 (m, 1H), 6.95-6.33 (m, 3H), 4.87-4.65 (m, 1H), 3.82-3.33 (m, 5H), 3.25-3.02 (m, 2H), 2.94-2.83 (m, 3H), 2.43-1.64 (m, 8H), 1.45 and 1.19 (two singlets, 9H).

Example 105B: (3-Methoxy-4-(1H-pyrazol-4-yl)phenyl)(2-(3-((1-methylpiperidin-4-yl)amino)phenyl)pyrrolidin-1-yl)methanone

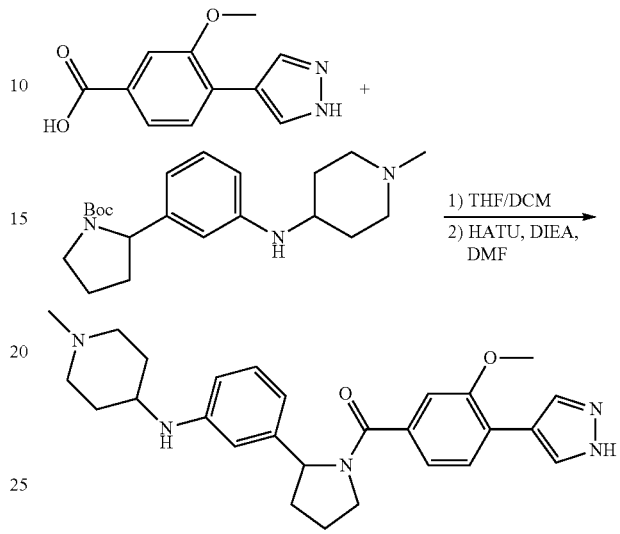

To a solution of Example 105A (20 mg, 0.034 mmol) in DCM (2 mL) was added TFA (1 mL). After stirred at rt for 30 min. The solvent was removed. To the residue were added Intermediate 1 (7.43 mg, 0.034 mmol), DIEA (0.030 mL, 0.170 mmol) and HATU (15.53 mg, 0.041 mmol) at rt. The reaction was stirred under N$_2$ at rt for 1 h. Purification by reverse phase chromatography afforded Example 105 (6.8 mg, 43%). LC-MS(ESI) m/z: 460.4[M+H]$^+$; $^1$H NMR (500 MHz, DMSO-d$_6$) δ 8.33-7.89 (m, 2H), 7.77-7.47 (m, 1H), 7.24-6.52 (m, 4H), 6.50-6.29 (m, 2H), 5.15-4.74 (m, 1H), 3.97-3.74 (m, 1H), 3.72-3.52 (m, 1H), 3.50-3.28 (m, 4H), 3.22-2.88 (m, 4H), 2.77 (d, J=11.8 Hz, 3H), 2.34-1.44 (m, 8H); Analytical HPLC RT=0.84 min (Method E), 1.01 min (Method F).

Example 106: (3S,5R)-5-(2-Fluorophenyl)-1-[3-methoxy-4-(1H-pyrazol-4-yl)benzoyl] pyrrolidin-3-amine, and Example 107: (3R,5R)-5-(2-Fluorophenyl)-1-[3-methoxy-4-(1H-pyrazol-4-yl)benzoyl] pyrrolidin-3-amine

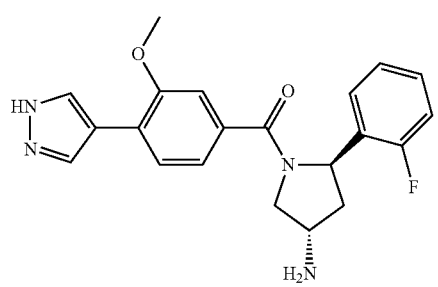

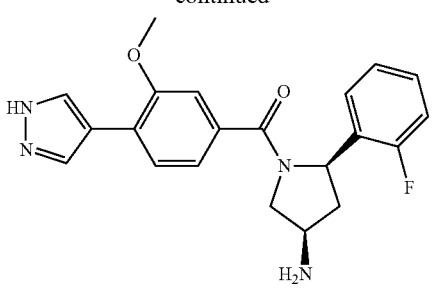

Example 106A: (5R)-1-(4-Bromo-3-methoxyben-zoyl)-5-(2-fluorophenyl)pyrrolidin-3-yl acetate

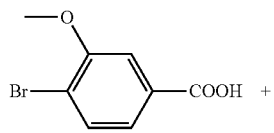

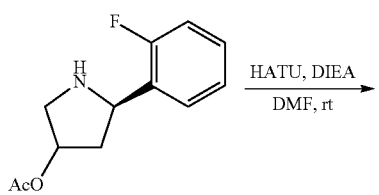

To a solution of Intermediate 5 (330 mg, 1.478 mmol) in DCM (3 mL) were added 4-bromo-3-methoxybenzoic acid (342 mg, 1.478 mmol), DIEA (0.645 mL, 3.70 mmol) and HATU (618 mg, 1.626 mmol) at rt. The reaction was stirred under argon at rt for 2 h. The crude product was purified by normal phase chromatography to afford Example 106A as a white solid (469 mg, 72.7%). LC-MS(ESI) m/z: 436.0/438.0 [M+H]$^+$; $^1$H NMR (400 MHz, CDCl$_3$) δ 7.58 (d, J=7.9 Hz, 1H), 7.47-7.32 (m, 1H), 7.28-6.96 (m, 4H), 6.93-6.47 (m, 1H), 5.61-5.14 (m, 2H), 4.13-4.01 (m, 1H), 3.93 (s, 2H), 3.76 (d, J=12.1 Hz, 1H), 3.58 (s, 1H), 2.74-2.48 (m, 1H), 2.42-2.23 (m, 1H), 2.09-2.00 (m, 3H).

Example 106B: (4-Bromo-3-methoxyphenyl)((2R)-2-(2-fluorophenyl)-4-hydroxypyrrolidin-1-yl)methanone

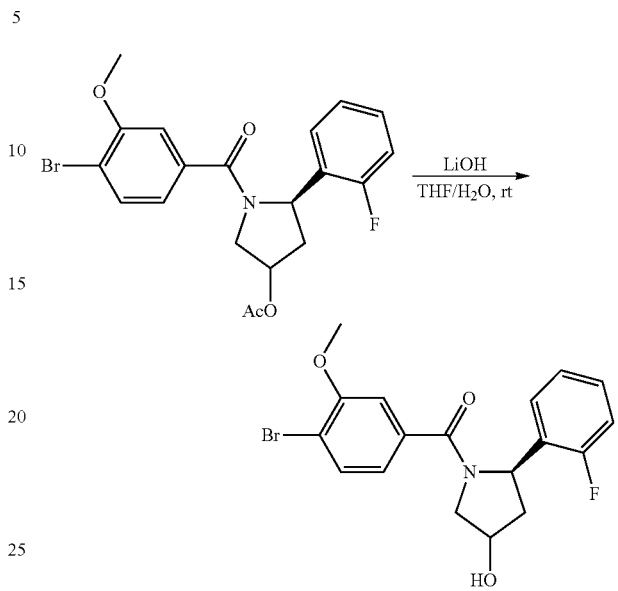

To a solution of Example 106A (469 mg, 1.075 mmol) in THF (5 mL) and water (2 mL) was added LiOH (51.5 mg, 2.150 mmol) at rt. The reaction was stirred under argon at rt for overnight. The reaction was acidified with 1.0 N HCl, and was diluted with EtOAc, washed with H$_2$O and brine. The organic phase was dried over sodium sulfate, filtered and concentrated to afford Example 106B as a white solid (420 mg, 100%). LC-MS(ESI) m/z: 394.0/396.0[M+H]$^+$.

Example 106C: (5R)-1-(4-Bromo-3-methoxyben-zoyl)-5-(2-fluorophenyl)pyrrolidin-3-yl methanesul-fonate

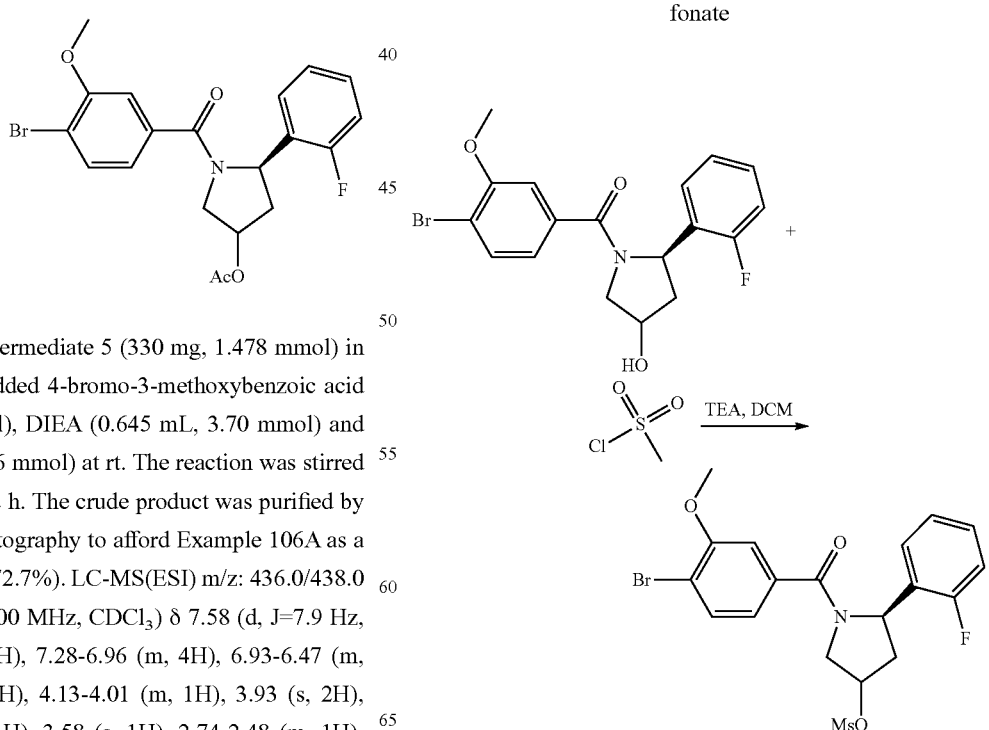

To a solution of Example 106B (200 mg, 0.507 mmol) in DCM (5 mL) were added TEA (0.141 mL, 1.015 mmol) and MsCl (0.047 mL, 0.609 mmol) at 0° C. The reaction was stirred under $N_2$ at 0° C. for 1.5 h. The solvent was removed to afford a crude product used without purification. LC-MS (ESI) m/z: 471.9/473.9[M+H]$^+$.

Example 106D: ((2R)-4-Azido-2-(2-fluorophenyl) pyrrolidin-1-yl)(4-bromo-3-methoxyphenyl)methanone

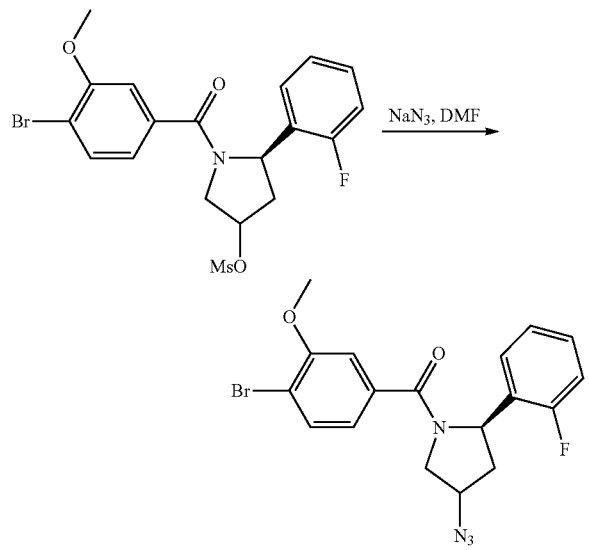

To a solution of Example 106C (59.5 mg, 0.126 mmol) in DMF (1 mL) were added $NaN_3$ (24.57 mg, 0.378 mmol) at rt. The reaction was stirred under $N_2$ at 60° C. overnight. The reaction mixture was diluted with EtOAc, washed with $H_2O$ and brine. The organic phase was dried over sodium sulfate, filtered and concentrated. The crude product was purified by normal phase chromatography to afford Example 106D as a solid (43 mg, 81%). LC-MS(ESI) m/z: 419.0/421.0[M+H]$^+$; $^1$H NMR (400 MHz, CDCl$_3$) δ 7.69-6.70 (m, 7H), 5.59-5.07 (m, 1H), 4.54-4.23 (m, 1H), 4.19-4.00 (m, 1H), 3.94 (br. s., 2H), 3.82-3.66 (m, 1H), 3.62-3.41 (m, 1H), 2.88-2.50 (m, 1H), 2.37-2.00 (m, 1H).

Example 106E: ((2R)-4-Azido-2-(2-fluorophenyl) pyrrolidin-1-yl)(3-methoxy-4-(1H-pyrazol-4-yl)phenyl)methanone

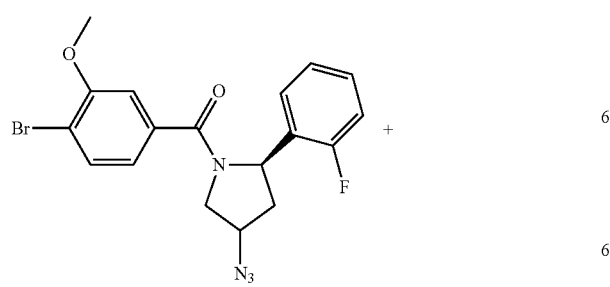

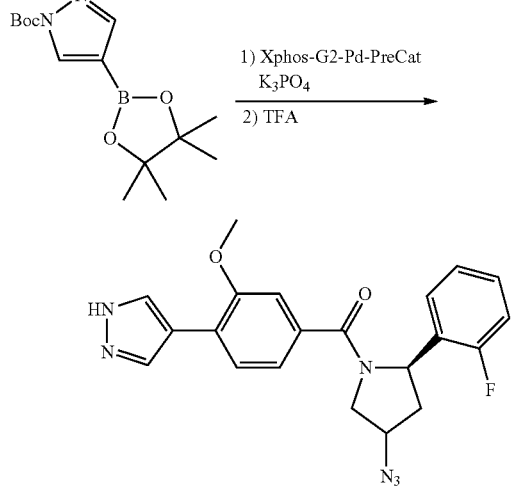

To a solution of Example 106D (43 mg, 0.103 mmol) in dioxane (5 mL) and $H_2O$ (1 mL) were added tert-butyl 4-(4,4,5,5-tetramethyl-1,3,2-dioxaborolan-2-yl)-1H-pyrazole-1-carboxylate (45.3 mg, 0.154 mmol), $K_3PO_4$ (65.3 mg, 0.308 mmol) and XPhos-G2-Pd-PreCat (8.07 mg, 10.26 μmol) at rt. The reaction was stirred under $N_2$ at rt for 1.5 h. The reaction mixture was diluted with DCM, washed with $H_2O$ and brine. The organic phase was dried over sodium sulfate, filtered and concentrated. The crude product was dissolved in DCM (1 mL), and TFA (0.5 mL) was added. After stirred at rt for 30 min, the solvent was removed to afford a crude product of Example 106E (42 mg, 100%). LC-MS(ESI) m/z: 407.0[M+H]$^+$.

Example 106 and Example 107

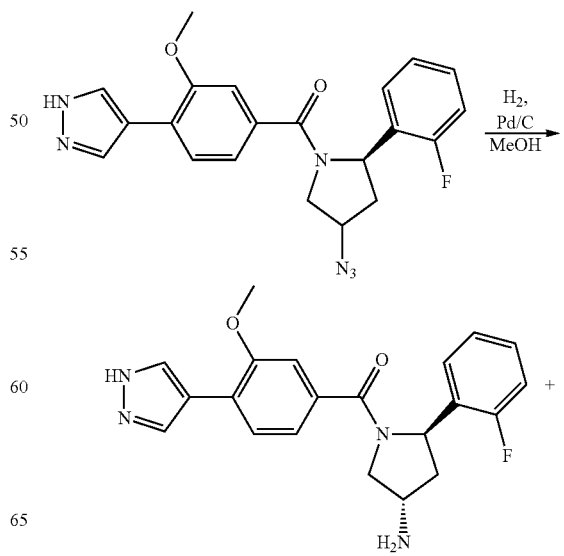

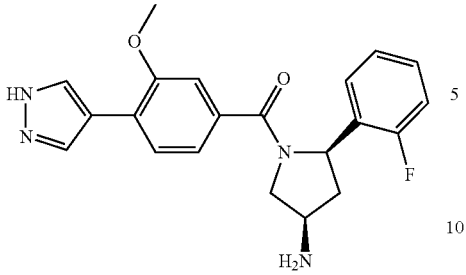

A solution of Example 106E (42 mg, 0.103 mmol) in MeOH (3 mL) was added catalytic amount of 10% Pd/C. The reaction was stirred under a hydrogen balloon for 1 h. The catalyst was filtered, and the solvent was removed from filtrate. Purification by reverse phase chromatography afforded Example 106 (18.4 mg, 47.0%), and Example 107 (1.5 mg, 3.8%).

Example 106

LC-MS(ESI) m/z: 381.05[M+H]$^+$; $^1$H NMR (500 MHz, DMSO-d$_6$) δ 8.19 (br. s., 2H), 7.81 (br. s., 1H), 7.56 (br. s., 1H), 7.45-6.97 (m, 5H), 5.40 (d, J=7.9 Hz, 1H), 3.99 (br. s., 3H), 3.66 (d, J=13.4 Hz, 3H), 2.86 (br. s., 1H), 1.98 (d, J=9.8 Hz, 1H); Analytical HPLC RT=0.91 min (Method E), 0.98 min (Method F).

Example 107

LC-MS(ESI) m/z: 381.05[M+H]$^+$; $^1$H NMR (500 MHz, DMSO-d$_6$) δ 8.20-7.94 (m, 2H), 7.71 (d, J=7.9 Hz, 1H), 7.45-6.70 (m, 6H), 5.57-5.18 (m, 1H), 4.08-3.79 (m, 2H), 3.72-3.43 (m, 3H), 3.36 (d, J=10.4 Hz, 1H), 2.23 (d, J=9.5 Hz, 1H), 1.96 (br. s., 1H); Analytical HPLC RT=0.99 min (Method E), 1.07 min (Method F).

Example 108: (5R)-5-(1H-Indazol-6-yl)-1-[3-methoxy-4-(1H-pyrazol-4-yl)benzoyl] pyrrolidin-3-ol, and Example 109: (5R)-5-(3-Iodo-1H-indazol-6-yl)-1-[3-methoxy-4-(1H-pyrazol-4-yl)benzoyl]pyrrolidin-3-ol

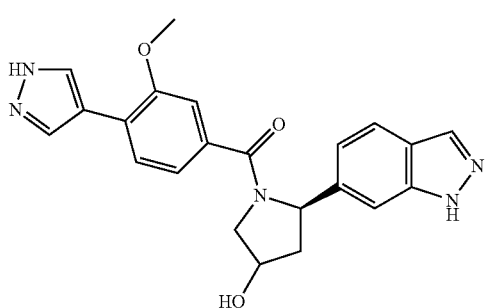

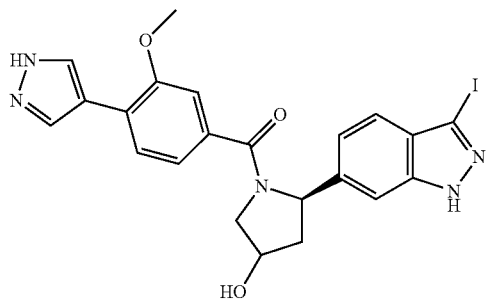

Example 108A: (5R)-5-(1H-Indazol-6-yl)pyrrolidin-3-yl acetate, and

Example 108B: (5R)-5-(3-Iodo-1H-indazol-6-yl) pyrrolidin-3-yl acetate

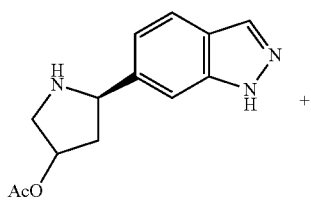

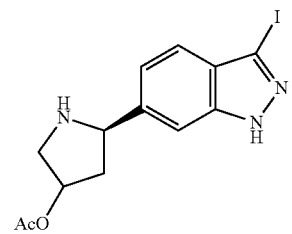

By following a similar procedure as described in Intermediate 3 by replacing 3-formylbenzoate with 1H-indazole-6-carbaldehyde in step 3A, Example 108A and 108B were obtained as a mixture, which was used without separation. LC-MS of Example 108A (ESI) m/z: 246.1 [M+H]$^+$; LC-MS of Example 108B (ESI) m/z: 372.0[M+H]$^+$.

Example 108C, Example 108 and Example 109

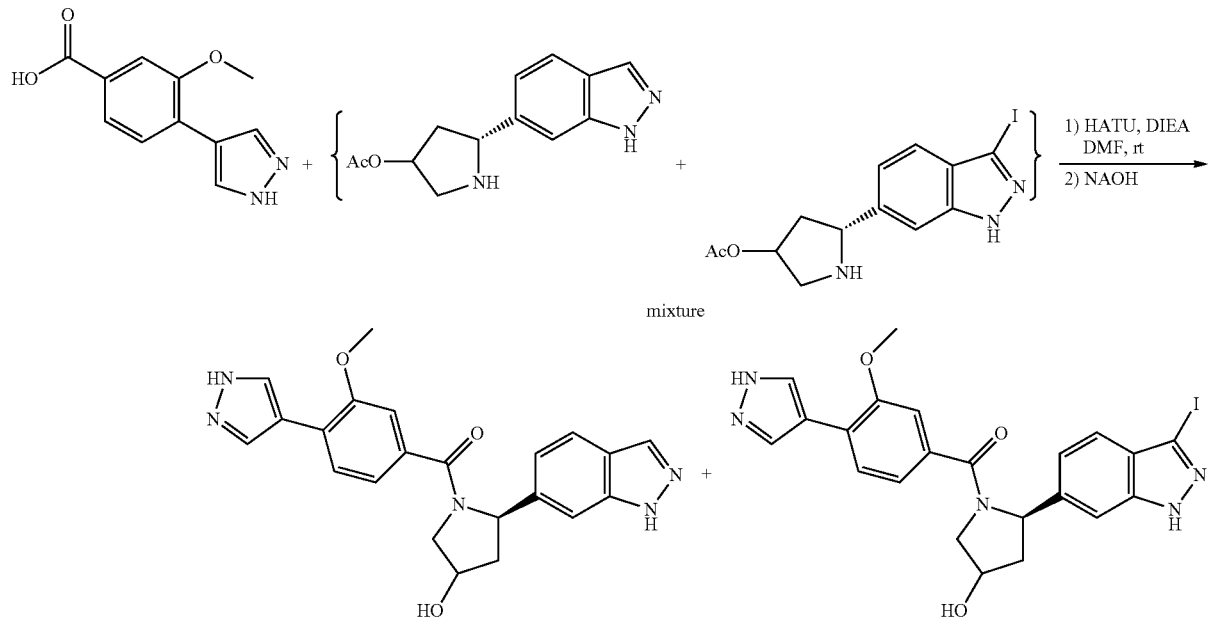

To a solution of a mixture of Examples 108A and 108B (30 mg, ~0.122 mmol) in DMF (2 mL) were added Intermediate 1 (26.7 mg, 0.122 mmol), DIEA (0.043 mL, 0.245 mmol) and HATU (46.5 mg, 0.122 mmol) at rt. The reaction was stirred under $N_2$ at rt for 1 h. To the reaction was added NaOH (1 N, 0.5 mL). The reaction was stirred for another 30 min. The reaction was neutralized with HCl. The crude product was purified by reverse phase chromatography to afford Example 108 (14.5 mg, 28.5%), and Example 109 (4.8 mg, 7.3%).

Example 108

LC-MS(ESI) m/z: 404.1[M+H]$^+$; $^1$H NMR (400 MHz, CD$_3$OD) δ 8.87-8.12 (m, 3H), 8.06-7.61 (m, 3H), 7.42-6.83 (m, 3H), 5.89-5.11 (m, 2H), 4.52-4.14 (m, 2H), 4.12-3.82 (m, 3H), 2.66-2.07 (m, 2H); Analytical HPLC RT=4.27 min (Method A), 4.70 min (Method B).

Example 109

LC-MS(ESI) m/z: 530.0[M+H]$^+$; $^1$H NMR (400 MHz, CD$_3$OD) δ 8.32-7.99 (m, 2H), 7.81-6.78 (m, 6H), 5.83-5.17 (m, 2H), 4.67-4.11 (m, 2H), 4.02 (s, 3H), 2.67-2.08 (m, 2H); Analytical HPLC RT=5.52 min (Method A), 5.94 min (Method B).

Example 110: (2R)-1-[3-Methoxy-4-(1H-pyrazol-4-yl)benzoyl]-N-phenylpyrrolidine-2-carboxamide

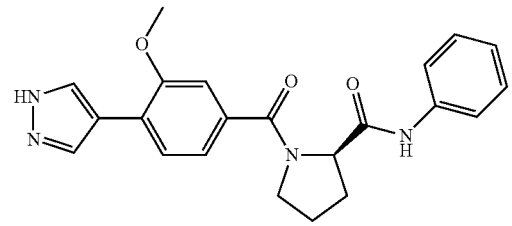 [SMILES: COc1cc(C(=O)N2CCC[C@@H]2C(=O)Nc2ccccc2)ccc1-c1cn[nH]c1]

Example 110A: (R)-1-(3-Methoxy-4-(1H-pyrazol-4-yl)benzoyl)pyrrolidine-2-carboxylic acid

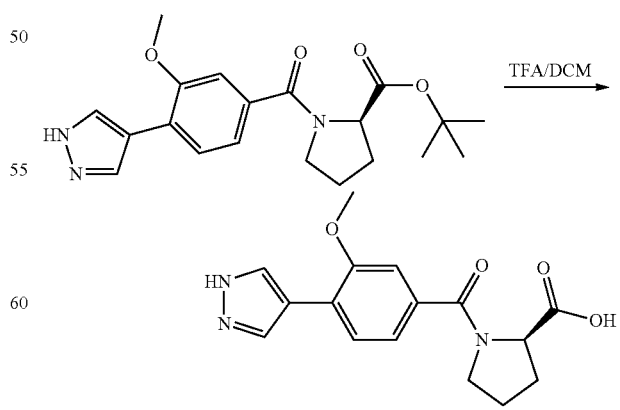

To a solution of Example 24 (151 mg, 0.407 mmol) in DCM (3 mL) was added TFA (2 mL, 26.0 mmol) at rt. The reaction was stirred under N₂ at rt for 2 h. The solvent was removed to afford Example 110A (125 mg, 98%) as a white solid. LC-MS(ESI) m/z: 316.0[M+H]⁺.

Example 110B, Example 110

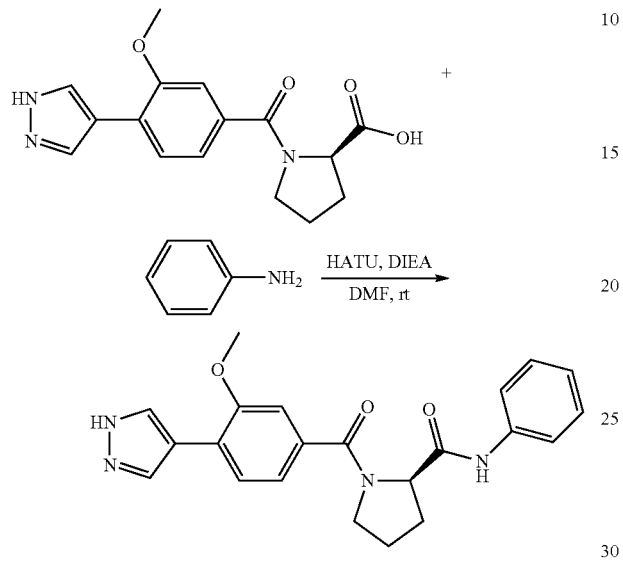

To a solution of Example 110A (20 mg, 0.063 mmol) in DMF (1 mL) were added aniline (11.81 mg, 0.127 mmol), DIEA (0.055 mL, 0.317 mmol) and HATU (26.5 mg, 0.070 mmol) at rt. The reaction was stirred under N₂ at rt for 1 h. Purification by reverse phase chromatography afforded Example 110 (12.2 mg, 49.3%). LC-MS(ESI) m/z: 391.40 [M+H]⁺; ¹H NMR (500 MHz, DMSO-d₆) δ 10.24-9.76 (m, 1H), 8.21-7.93 (m, 2H), 7.73-7.33 (m, 3H), 7.33-6.89 (m, 5H), 4.67-4.32 (m, 1H), 3.92-3.51 (m, 5H), 2.28 (d, J=5.8 Hz, 1H), 2.00-1.75 (m, 3H); Analytical HPLC RT=1.21 min (Method E), 1.25 min (Method F).

Example 111: 1-[(2R)-1-[3-Methoxy-4-(1H-pyrazol-4-yl)benzoyl]pyrrolidine-2-carbonyl]-2,3-dihydro-1H-indole

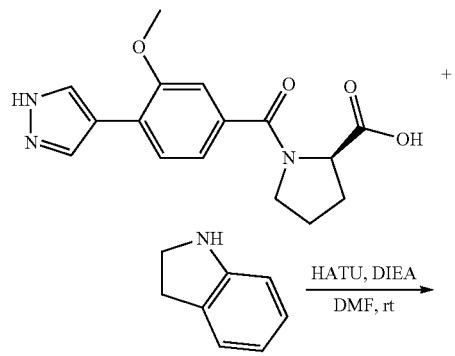

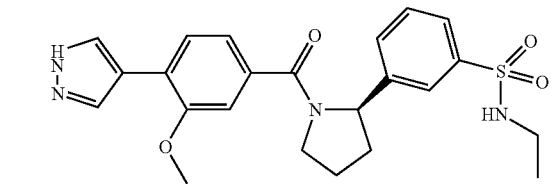 [SMILES: CCNS(=O)(=O)c1cccc([C@H]2CCCN2C(=O)c2ccc(-c3cn[nH]c3)c(OC)c2)c1]

Example 111 was prepared by following the same procedure as described in Example 110, by replacing aniline with indoline. LC-MS(ESI) m/z: 417.15[M+H]⁺; ¹H NMR (500 MHz, DMSO-d₆) δ 8.20-7.88 (m, 3H), 7.76-7.51 (m, 1H), 7.30-6.89 (m, 5H), 4.91-4.61 (m, 1H), 4.41-4.17 (m, 1H), 3.91 (s, 2H), 3.72-3.55 (m, 4H), 3.36-2.94 (m, 2H), 2.39 (br. s., 1H), 2.03-1.90 (m, 3H); Analytical HPLC RT=1.34 min (Method E), 1.38 min (Method F).

Example 112: N-Ethyl-3-[(2R)-1-[3-methoxy-4-(1H-pyrazol-4-yl)benzoyl]pyrrolidin-2-yl]benzene-1-sulfonamide

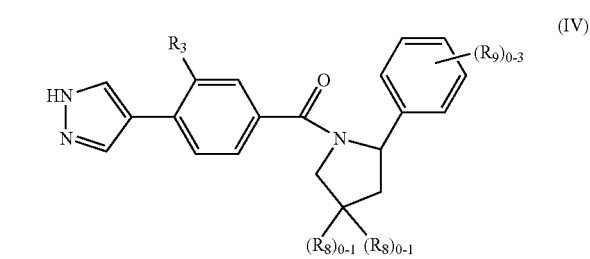

Example 112 was prepared by following the procedure as described in Example 31, by replacing 1-bromo-3-(methylsulfonyl)benzene with 3-bromo-N-ethylbenzenesulfonamide in Example 31A. LC-MS(ESI) m/z: 455.2[M+H]⁺; ¹H NMR (500 MHz, DMSO-d₆) δ 8.22-7.96 (m, 2H), 7.80-7.30 (m, 6H), 7.24-6.58 (m, 2H), 5.19, 5.10 (s, 1H), 4.01-3.36 (m, 5H), 2.84-2.73 (m, 1H), 2.63 (br. s., 1H), 1.90 (s, 3H), 1.76 (d, J=5.8 Hz, 1H), 1.01-0.80 (m, 3H); Analytical HPLC RT=1.29 min (Method E), 1.30 min (Method F).

What is claimed is:

1. A compound of formula (IV):

$$\text{(IV)}$$

or an enantiomer, a diastereomer, a stereoisomer, or a pharmaceutically acceptable salt thereof,
wherein:
$R_3$ is independently selected from CN, $C_{1-4}$ alkyl substituted with 0-3 $R_e$, and $-OR_b$;
$R_8$ is independently selected from F, $C_{1-4}$ alkyl substituted with 0-3 $R_e$, $-(CH_2)_rOR_b$, $-(CH_2)_rC(=O)R_b$, $-NR_aR_a$, $-C(=O)NR_aR_a$, and $-C(=O)OR_b$;

$R_9$ is independently selected from F, Cl, Br, $C_{1-4}$ alkyl, nitro, —S(O)$_p$R$_c$, —S(O)$_p$NR$_a$R$_a$, —OR$_b$, —NR$_a$R$_a$, —C(=O)OR$_b$, —(CH$_2$)$_r$C(=O)R$_b$, —C(=O)NR$_a$R$_a$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

R$_a$, at each occurrence, is independently selected from H, CN, $C_{1-6}$ alkyl substituted with 0-5 R$_e$, —(CH$_2$)$_r$—$C_{3-6}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, $C_{1-6}$ alkyl substituted with 0-5 R$_e$, $C_{2-6}$ alkenyl substituted with 0-5 R$_e$, $C_{2-6}$ alkynyl substituted with 0-5 R$_e$, —(CH$_2$)$_r$—$C_{3-10}$carbocyclyl substituted with 0-5 R$_e$, and —(CH$_2$)$_r$-heterocyclyl substituted with 0-5 R$_e$;

R$_c$, at each occurrence, is independently selected from $C_{1-6}$ alkyl substituted with 0-5 R$_e$, $C_{2-6}$alkenyl substituted with 0-5 R$_e$, $C_{2-6}$alkynyl substituted with 0-5 R$_e$, $C_{3-6}$carbocyclyl, and heterocyclyl;

R$_e$, at each occurrence, is independently selected from $C_{1-6}$ alkyl substituted with 0-5 R$_f$, $C_{2-6}$ alkenyl, $C_{2-6}$ alkynyl, —(CH$_2$)$_r$—$C_{3-6}$ cycloalkyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

R$_f$, at each occurrence, is independently selected from H, F, Cl, Br, CN, OH, $C_{1-5}$ alkyl, $C_{3-6}$ cycloalkyl, and phenyl, or R$_f$ and R$_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4;

provided that R$_3$ is not OPh.

2. The compound of claim 1, or an enantiomer, a diastereomer, a stereoisomer, or a pharmaceutically acceptable salt thereof, wherein:

R$_9$ is independently selected from F, Cl, Br, $C_{1-4}$ alkyl, nitro, —S(O)$_p$R$_c$, —S(O)$_p$NR$_a$R$_a$, —OR$_b$, —NR$_a$R$_a$, —C(=O)OR$_b$, —(CH$_2$)$_r$C(=O)R$_b$, —C(=O)NR$_a$R$_a$, —(CH$_2$)$_r$-cycloalkyl, —(CH$_2$)$_r$-heterocyclyl, —(CH$_2$)$_r$-aryl, and —(CH$_2$)$_r$-heteroaryl selected from

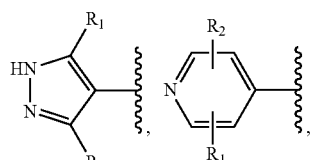

and 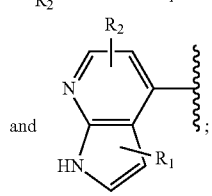;

R$_e$, at each occurrence, is independently selected from $C_{1-6}$ alkyl substituted with 0-5 R$_f$, $C_{2-6}$ alkenyl, $C_{2-6}$ alkynyl, —(CH$_2$)$_r$—$C_{3-6}$ cycloalkyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$; and R$_e$' is independently selected from H and $C_{1-4}$ alkyl substituted with 0-5 R$_f$.

3. The compound of claim 2 or an enantiomer, a diastereomer, a stereoisomer, or a pharmaceutically acceptable salt thereof, wherein:

R$_9$ is —C(=O)NR$_a$R$_a$;

R$_a$, at each occurrence, is independently selected from H, CN, $C_{1-6}$ alkyl substituted with 0-5 R$_e$, —(CH$_2$)$_r$—$C_{3-6}$cycloalkyl substituted with 0-5 R$_e$, —(CH$_2$)$_r$-aryl substituted with 0-5 R$_e$, and —(CH$_2$)$_r$-heterocyclyl independently selected from

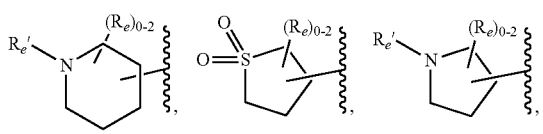

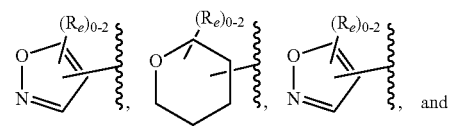, and

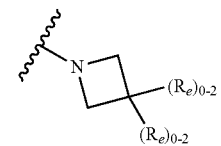

R$_b$, at each occurrence, is independently selected from H, $C_{1-6}$ alkyl substituted with 0-5 R$_e$, $C_{2-6}$ alkenyl substituted with 0-5 R$_e$, $C_{2-6}$ alkynyl substituted with 0-5 R$_e$, —(CH$_2$)$_r$—$C_{3-10}$carbocyclyl substituted with 0-5 R$_e$, and —(CH$_2$)$_r$-heterocyclyl substituted with 0-5 R$_e$;

R$_c$, at each occurrence, is independently selected from $C_{1-6}$ alkyl substituted with 0-5 R$_e$, $C_{2-6}$alkenyl substituted with 0-5 R$_e$, $C_{2-6}$alkynyl substituted with 0-5 R$_e$, $C_{3-6}$carbocyclyl, and heterocyclyl;

R$_e$, at each occurrence, is independently selected from $C_{1-6}$ alkyl substituted with 0-5 R$_f$, $C_{2-6}$ alkenyl, $C_{2-6}$ alkynyl, —(CH$_2$)$_r$—$C_{3-6}$ cycloalkyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

R$_e$' is independently selected from H and $C_{1-4}$ alkyl substituted with 0-5 R$_f$;

R$_f$, at each occurrence, is independently selected from H, F, Cl, Br, CN, OH, $C_{1-5}$ alkyl, $C_{3-6}$ cycloalkyl, and phenyl, or R$_f$ and R$_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

4. A compound of formula (V):

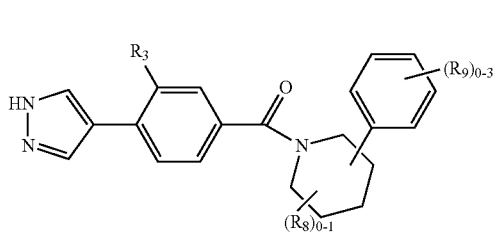

or an enantiomer, a diastereomer, a stereoisomer, or a pharmaceutically acceptable salt thereof, wherein:

$R_3$ is independently selected from CN, $C_{1-4}$ alkyl substituted with 0-3 $R_e$, and $-OR_b$;

$R_8$ is independently selected from F, $C_{1-4}$ alkyl substituted with 0-3 $R_e$, $-(CH_2)_rOR_b$, $-(CH_2)_rC(=O)R_b$, $-NR_aR_a$, $-C(=O)NR_aR_a$, and $-C(=O)OR_b$;

$R_9$ is independently selected from F, Cl, Br, $C_{1-4}$ alkyl, nitro, $-S(O)_pR_c$, $-S(O)_pNR_aR_a$, $-OR_b$, $-NR_aR_a$, $-C(=O)OR_b$, $-(CH_2)_rC(=O)R_b$, $-C(=O)NR_aR_a$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, $-(CH_2)_r-C_{3-6}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, F, Cl, Br, CN, $NO_2$, $=O$, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4; provided that $R_3$ is not OPh.

5. A compound of formula (VI):

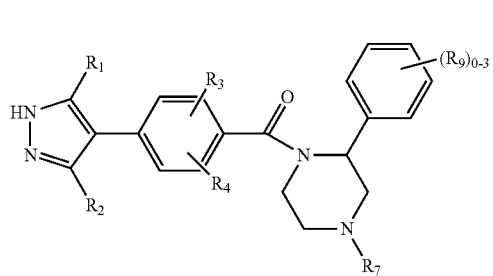

or an enantiomer, a diastereomer, a stereoisomer, or a pharmaceutically acceptable salt thereof, wherein:

$R_1$ is independently selected from H, F, Cl, Br, OH, CN, $NR_aR_a$, $-OC_{1-4}$ alkyl substituted with 0-3 $R_e$, and $C_{1-4}$ alkyl substituted with 0-3 $R_e$;

$R_2$ is independently selected from H, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rCN$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;

$R_3$ is independently selected from F, $C_{1-4}$alkyl substituted with 0-3 $R_e$, $-OR_b$ and $S(O)_2R_c$;

$R_4$ is independently selected from H, F, methyl, and ethyl;

$R_7$ is independently selected from H, $C_{1-4}$alkyl substituted with 0-4 $R_e$, $-C(=O)R_b$, $-C(=O)NR_aR_a$, $-C(=O)(CH_2)_rNR_aR_a$, and $-C(=O)OR_b$;

$R_9$ is independently selected from F, Cl, Br, $C_{1-4}$ alkyl, $S(O)_pR_c$, $-OR_b$, $-(CHR_d)_rC(=O)OR_b$, $-(CHR_d)_rC(=O)R_b$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, F, Cl, Br, CN, $NO_2$, $=O$, $CO_2H$, $-(CH_2)_rOR_f$ and $-(CH_2)_rNR_fR_f$;

$R_f$, at each occurrence, is independently selected from H, F, Cl, Br, CN, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4; provided that $R_3$ is not OPh.

6. A compound selected from:
4-[2-methoxy-4-(2-phenylpyrrolidine-1-carbonyl)phenyl]-1H-pyrazole (1);
4-[2-methoxy-4-(3-phenylpyrrolidine-1-carbonyl)phenyl]-1H-pyrazole (2);
[(2S)-1-[3-methoxy-4-(1H-pyrazol-4-yl)benzoyl]pyrrolidin-2-yl]methanol (3);
4-{2-methoxy-4-[2-(3-methoxyphenyl)pyrrolidine-1-carbonyl]phenyl}—1H-pyrazole (4);
N-(2,3-dihydro-1H-inden-1-yl)-3-methoxy-4-(1H-pyrazol-4-yl)benzamide (5);
4-{2-methoxy-4-[2-(2-methoxyphenyl)pyrrolidine-1-carbonyl]phenyl}—1H-pyrazole (6);
1-[3-methoxy-4-(1H-pyrazol-4-yl)benzoyl]-3-phenylpiperidine (7);
2-(2-fluorophenyl)-1-[3-methoxy-4-(1H-pyrazol-4-yl)benzoyl]piperidine (8);
1-[3-methoxy-4-(1H-pyrazol-4-yl)benzoyl]-2-(3-methoxyphenyl)piperidine (9);
4-{4-[2-(4-chlorophenyl)pyrrolidine-1-carbonyl]-2-methoxyphenyl}-1H-pyrazole (10);
4-{2-methoxy-4-[2-(3-methoxyphenyl)pyrrolidine-1-carbonyl]phenyl}-1H-pyrazole (11);
4-{2-methoxy-4-[2-(3-methoxyphenyl)pyrrolidine-1-carbonyl]phenyl}—1H-pyrazole (12);
1-[3-methoxy-4-(1H-pyrazol-4-yl)benzoyl]-2,3-dihydro-1H-indole (13);
4-[4-(2-benzylpyrrolidine-1-carbonyl)-2-methoxyphenyl]—1H-pyrazole (14);
4-{4-[2-(3-bromophenyl)pyrrolidine-1-carbonyl]-2-methoxyphenyl}-1H-pyrazole (15);
3-{1-[3-methoxy-4-(1H-pyrazol-4-yl)benzoyl]pyrrolidin-2-yl}benzene-1-sulfonamide (16);
3-{1-[3-methoxy-4-(1H-pyrazol-4-yl)benzoyl]pyrrolidin-2-yl}benzene-1-sulfonamide (17);
3-{1-[3-methoxy-4-(1H-pyrazol-4-yl)benzoyl]pyrrolidin-2-yl}benzene-1-sulfonamide (18);
4-{4-[2-(4-fluorophenyl)pyrrolidine-1-carbonyl]-2-methoxyphenyl}-1H-pyrazole (19);
4-{4-[2-(2-fluorophenyl)pyrrolidine-1-carbonyl]-2-methoxyphenyl}-1H-pyrazole (20);
3-{1-[3-methoxy-4-(1H-pyrazol-4-yl)benzoyl]pyrrolidin-2-yl}phenol (21);
4-(2-methoxy-4-{2-[4-(trifluoromethyl)phenyl]pyrrolidine-1-carbonyl}phenyl)-1H-pyrazole (22);
4-{2-methoxy-4-[2-(4-methylphenyl)pyrrolidine-1-carbonyl]phenyl}-1H-pyrazole (23);
tert-butyl (2R)-1-[3-methoxy-4-(1H-pyrazol-4-yl)benzoyl]pyrrolidine-2-carboxylate (24);
4-{2-methoxy-4-[2-(4-methoxyphenyl)pyrrolidine-1-carbonyl]phenyl}-1H-pyrazole (25);
4-[2-methoxy-4-(2-phenylpyrrolidine-1-carbonyl)phenyl]-1H-pyrazole (26);
4-{2-methoxy-4-[2-(3-methylphenyl)pyrrolidine-1-carbonyl]phenyl}—1H-pyrazole (27);
4-{4-[2-(2-chlorophenyl)pyrrolidine-1-carbonyl]-2-methoxyphenyl}-1H-pyrazole (28);
4-{2-methoxy-4-[2-(naphthalen-2-yl)pyrrolidine-1-carbonyl]phenyl}—1H-pyrazole (29);
4-{4-[2-(2H-1,3-benzodioxol-5-yl)pyrrolidine-1-carbonyl]-2-methoxyphenyl}-1H-pyrazole (30);
4-{4-[(2R)-2-(3-methanesulfonylphenyl)pyrrolidine-1-carbonyl]-2-methoxyphenyl}-1H-pyrazole (31);
methyl 3-[(2R)-1-[3-methoxy-4-(1H-pyrazol-4-yl)benzoyl]pyrrolidin-2-yl]benzoate (32);
3-[(2R)-1-[3-methoxy-4-(1H-pyrazol-4-yl)benzoyl]pyrrolidin-2-yl]benzoic acid (33);
4-{4-[(2R)-2-(3-methanesulfonylphenyl)pyrrolidine-1-carbonyl]-2-methoxyphenyl}-1H-pyrazole (34);
N-ethyl-3-(1-(3-methoxy-4-(1H-pyrazol-4-yl)benzoyl)pyrrolidin-2-yl)benzamide (35);
3-{1-[3-methoxy-4-(1H-pyrazol-4-yl)benzoyl]pyrrolidin-2-yl}-N-(1-methylpiperidin-4-yl)benzamide (36);
3-{1-[3-methoxy-4-(1H-pyrazol-4-yl)benzoyl]pyrrolidin-2-yl}-N-(1-methylpiperidin-4-yl)benzamide (37);
3-{1-[3-methoxy-4-(1H-pyrazol-4-yl)benzoyl]pyrrolidin-2-yl}-N-(1-methylpiperidin-4-yl)benzamide (38);
N-(2-hydroxy-2-methylpropyl)-3-[(2R)-1-[3-methoxy-4-(1H-pyrazol-4-yl)benzoyl]pyrrolidin-2-yl]benzamide (39);
3-[(2R)-1-[3-methoxy-4-(1H-pyrazol-4-yl)benzoyl]pyrrolidin-2-yl]-N,N-dimethylbenzamide (40);
N-(1,1-dioxo-1λ$^6$-thiolan-3-yl)-3-[(2R)-1-[3-methoxy-4-(1H-pyrazol-4-yl)benzoyl]pyrrolidin-2-yl]benzamide (41);
N-cyclopropyl-3-[(2R)-1-[3-methoxy-4-(1H-pyrazol-4-yl)benzoyl]pyrrolidin-2-yl]benzamide (42);
methyl 3-[(2R)-4-(acetyloxy)-1-[3-methoxy-4-(1H-pyrazol-4-yl)benzoyl]pyrrolidin-2-yl]benzoate (43);
3-[(2R)-4-hydroxy-1-[3-methoxy-4-(1H-pyrazol-4-yl)benzoyl]pyrrolidin-2-yl]benzoic acid (44);
N-ethyl-3-[(2R)-4-hydroxy-1-[3-methoxy-4-(1H-pyrazol-4-yl)benzoyl]pyrrolidin-2-yl]benzamide (45);
3-[(2R)-4-hydroxy-1-[3-methoxy-4-(1H-pyrazol-4-yl)benzoyl]pyrrolidin-2-yl]-N-methylbenzamide (46);
3-[(2R)-4-hydroxy-1-[3-methoxy-4-(1H-pyrazol-4-yl)benzoyl]pyrrolidin-2-yl]-N-(2-hydroxy-2-methylpropyl)benzamide (47);
N-cyclopropyl-3-[(2R)-4-hydroxy-1-[3-methoxy-4-(1H-pyrazol-4-yl)benzoyl]pyrrolidin-2-yl]benzamide (48);
N-{[(2 S)-1-ethylpyrrolidin-2-yl]methyl}-3-[(2R)-4-hydroxy-1-[3-methoxy-4-(1H-pyrazol-4-yl)benzoyl]pyrrolidin-2-yl]benzamide (49);
3-[(2R)-4-hydroxy-1-[3-methoxy-4-(1H-pyrazol-4-yl)benzoyl]pyrrolidin-2-yl]-N-(2-methoxyethyl)benzamide (50);
N-(cyclopropylmethyl)-3-[(2R)-4-hydroxy-1-[3-methoxy-4-(1H-pyrazol-4-yl)benzoyl]pyrrolidin-2-yl]benzamide (51);
3-[(2R)-4-hydroxy-1-[3-methoxy-4-(1H-pyrazol-4-yl)benzoyl]pyrrolidin-2-yl]-N-(propan-2-yl)benzamide (52);
3-[(2R)-4-hydroxy-1-[3-methoxy-4-(1H-pyrazol-4-yl)benzoyl]pyrrolidin-2-yl]-N—(1-methylcyclobutyl)benzamide (53);
N-cyclobutyl-3-[(2R)-4-hydroxy-1-[3-methoxy-4-(1H-pyrazol-4-yl)benzoyl]pyrrolidin-2-yl]benzamide (54);
3-[(2R)-4-hydroxy-1-[3-methoxy-4-(1H-pyrazol-4-yl)benzoyl]pyrrolidin-2-yl]-N-(1,3-oxazol-2-ylmethyl)benzamide (55);
3-[(2R)-4-hydroxy-1-[3-methoxy-4-(1H-pyrazol-4-yl)benzoyl]pyrrolidin-2-yl]-N-(oxan-4-yl)benzamide (56);

3-[(2R)-4-hydroxy-1-[3-methoxy-4-(1H-pyrazol-4-yl)
benzoyl]pyrrolidin-2-yl]-N-(1-methylcyclopropyl)benzamide (57);
3-[(2R)-4-hydroxy-1-[3-methoxy-4-(1H-pyrazol-4-yl)
benzoyl]pyrrolidin-2-yl]-N— [(3-methyl-1,2-oxazol-5-yl)methyl]benzamide (58);
3-[(2R)-4-hydroxy-1-[3-methoxy-4-(1H-pyrazol-4-yl)
benzoyl]pyrrolidin-2-yl]-N— [(5-methyl-1,2-oxazol-3-yl)methyl]benzamide (59);
N-(2,2-difluoroethyl)-3-[(2R)-4-hydroxy-1-[3-methoxy-4-(1H-pyrazol-4-yl)benzoyl]pyrrolidin-2-yl]benzamide (60);
1-{3-[(2R)-4-hydroxy-1-[3-methoxy-4-(1H-pyrazol-4-yl)
benzoyl]pyrrolidin-2-yl]benzoyl}azetidine-3-carbonitrile (61);
(5R)-1-[3-methoxy-4-(1H-pyrazol-4-yl)benzoyl]-5-[3-(3-methoxyazetidine-1-carbonyl)phenyl]pyrrolidin-3-ol (62);
N-{[2-fluoro-4-(trifluoromethyl)phenyl]methyl}-3-[(2R)-4-hydroxy-1-[3-methoxy-4-(1H-pyrazol-4-yl)
benzoyl]pyrrolidin-2-yl]benzamide (63);
(5R)-5-[3-(3-fluoroazetidine-1-carbonyl)phenyl]-1-[3-methoxy-4-(1H-pyrazol-4-yl)benzoyl]pyrrolidin-3-ol (64);
(5R)-5-[3-(3,3-difluoroazetidine-1-carbonyl)phenyl]—1-[3-methoxy-4-(1H-pyrazol-4-yl)benzoyl]pyrrolidin-3-ol (65);
N-{[3-fluoro-5-(trifluoromethyl)phenyl]methyl}-3-[(2R)-4-hydroxy-1-[3-methoxy-4-(1H-pyrazol-4-yl)
benzoyl]pyrrolidin-2-yl]benzamide (66);
(5R)-5-[3-(azetidine-1-carbonyl)phenyl]—1-[3-methoxy-4-(1H-pyrazol-4-yl)benzoyl]pyrrolidin-3-ol (67);
1-[3-methoxy-4-(1H-pyrazol-4-yl)benzoyl]-2-phenylpiperazine (68);
3-methoxy-N—[(3 S,4R)-4-phenylpyrrolidin-3-yl]-4-(1H-pyrazol-4-yl)benzamide (69);
trans-(+)-3-methoxy-N-(4-phenylpyrrolidin-3-yl)-4-(1H-pyrazol-4-yl)benzamide (70);
4-(2-methoxy-4-{2-[3-(1H-pyrazol-4-yl)phenyl]pyrrolidine-1-carbonyl}phenyl)-1H-pyrazole (71);
4-(3-methoxy-4-{2-[3-(1H-pyrazol-4-yl)phenyl]pyrrolidine-1-carbonyl}phenyl)-1H-pyrazole (72);
5-(3-{1-[3-methoxy-4-(1H-pyrazol-4-yl)benzoyl]pyrrolidin-2-yl}phenyl)-1-methyl-1H-pyrazole (73);
1-[4-(3-{1-[3-methoxy-4-(1H-pyrazol-4-yl)benzoyl]pyrrolidin-2-yl}phenyl)-1H-pyrazol-1-yl]-2-methylpropan-2-ol (74);
4-(3-{1-[3-methoxy-4-(1H-pyrazol-4-yl)benzoyl]pyrrolidin-2-yl}phenyl)-3,5-dimethyl-1,2-oxazole (75);
4-(4-{2-[3-(furan-3-yl)phenyl]pyrrolidine-1-carbonyl}-2-methoxyphenyl)-1H-pyrazole (76);
4-(2-methoxy-4-{2-[3-(1H-pyrazol-5-yl)phenyl]pyrrolidine-1-carbonyl}phenyl)-1H-pyrazole (77);
N-cyclopropyl-3-[(2R)-4-fluoro-1-[3-methoxy-4-(1H-pyrazol-4-yl)benzoyl]pyrrolidin-2-yl]benzamide (78);
N-cyclopropyl-3-[(2R)-4,4-difluoro-1-[3-methoxy-4-(pyridin-4-yl)benzoyl]pyrrolidin-2-yl]benzamide (79);
N-cyclopropyl-3-[(2R)-4,4-difluoro-1-[3-methoxy-4-(1H-pyrazol-4-yl)benzoyl]pyrrolidin-2-yl]benzamide (80);
4-{2-methoxy-4-[2-(3-methoxyphenyl)pyrrolidine-1-carbonyl]phenyl}pyridin-2-amine (81);
1-(3-methoxy-4-{1H-pyrrolo[2,3-b]pyridin-4-yl}benzoyl)-2-(3-methoxyphenyl) pyrrolidine (82);
2-fluoro-4-{2-methoxy-4-[2-(3-methoxyphenyl)pyrrolidine-1-carbonyl]phenyl}pyridine (83);
3-fluoro-4-{2-methoxy-4-[2-(3-methoxyphenyl)pyrrolidine-1-carbonyl]phenyl}pyridine (84);
4-{2-methoxy-4-[2-(3-methoxyphenyl)pyrrolidine-1-carbonyl]phenyl}-3-methylpyridine (85);
(5R)-5-(3-methanesulfonylphenyl)-1-(4-{1H-pyrrolo[2,3-b]pyridin-4-yl}benzoyl) pyrrolidin-3-ol (99);
N-(cyclopropylmethyl)-3-[(2R)-4-methoxy-1-[3-methoxy-4-(1H-pyrazol-4-yl)benzoyl]pyrrolidin-2-yl]benzamide (86);
N-(cyclopropylmethyl)-3-[(2R)-4-methoxy-1-[3-methoxy-4-(1H-pyrazol-4-yl)benzoyl]pyrrolidin-2-yl]-N-methylbenzamide (87);
N-(cyclopropylmethyl)-3-[(2R,4R)-4-hydroxy-1-[3-methoxy-4-(1H-pyrazol-4-yl)benzoyl]-4-methylpyrrolidin-2-yl]benzamide (88);
(5R)-5-(3-methanesulfonylphenyl)-1-[3-methoxy-4-(1H-pyrazol-4-yl)benzoyl]pyrrolidin-3-yl acetate (89);
(5R)-5-(3-methanesulfonylphenyl)-1-[3-methoxy-4-(1H-pyrazol-4-yl)benzoyl]pyrrolidin-3-ol (90);
(5R)-5-(2-fluorophenyl)-1-[3-methoxy-4-(1H-pyrazol-4-yl)benzoyl]pyrrolidin-3-yl acetate (91);
(3R,5R)-5-(2-fluorophenyl)-1-[3-methoxy-4-(1H-pyrazol-4-yl)benzoyl]pyrrolidin-3-ol (92);
(3 S,5R)-5-(2-fluorophenyl)-1-[3-methoxy-4-(1H-pyrazol-4-yl)benzoyl]pyrrolidin-3-ol (93);
(3R,5R)-1-[3-(difluoromethoxy)-4-(1H-pyrazol-4-yl)
benzoyl]-5-(2-fluorophenyl) pyrrolidin-3-ol (94);
(3 S,5R)-1-[3-(difluoromethoxy)-4-(1H-pyrazol-4-yl)
benzoyl]-5-(2-fluorophenyl) pyrrolidin-3-ol (95);
5-[(2R,4R)-2-(2-fluorophenyl)-4-hydroxypyrrolidine-1-carbonyl]-2-(1H-pyrazol-4-yl)benzonitrile (96);
5-[(2R)-2-(2-fluorophenyl)-4-hydroxypyrrolidine-1-carbonyl]-2-(1H-pyrazol-4-yl)benzonitrile (97);
(3R,5R)-5-(2-fluorophenyl)-1-[2-methoxy-4-(1H-pyrazol-4-yl)benzoyl]pyrrolidin-3-ol (98);
1-{5-[2-(3-methoxyphenyl)pyrrolidine-1-carbonyl]-2-(1H-pyrazol-4-yl)phenyl}ethan-1-ol (100);
(5R)-1-[3-ethyl-4-(1H-pyrazol-4-yl)benzoyl]-5-(2-fluorophenyl)pyrrolidin-3-ol (101);
4-(4-{2-[3-(2,2-difluoroethoxy)phenyl]pyrrolidine-1-carbonyl}-2-methoxyphenyl)-1H-pyrazole (102);
3-(3-{1-[3-methoxy-4-(1H-pyrazol-4-yl)benzoyl]pyrrolidin-2-yl}phenoxymethyl)-5-methyl-1,2-oxazole (103);
4-(3-{1-[3-methoxy-4-(1H-pyrazol-4-yl)benzoyl]pyrrolidin-2-yl}phenoxy)-1-methylpiperidine (104);
N-(3-{1-[3-methoxy-4-(1H-pyrazol-4-yl)benzoyl]pyrrolidin-2-yl}phenyl)-1-methylpiperidin-4-amine (105);
(3 S,5R)-5-(2-fluorophenyl)-1-[3-methoxy-4-(1H-pyrazol-4-yl)benzoyl]pyrrolidin-3-amine (106);
(3R,5R)-5-(2-fluorophenyl)-1-[3-methoxy-4-(1H-pyrazol-4-yl)benzoyl]pyrrolidin-3-amine (107);
(5R)-5-(1H-indazol-6-yl)-1-[3-methoxy-4-(1H-pyrazol-4-yl)benzoyl]pyrrolidin-3-ol (108);
(5R)-5-(3-iodo-1H-indazol-6-yl)-1-[3-methoxy-4-(1H-pyrazol-4-yl)benzoyl]pyrrolidin-3-ol (109);
(2R)-1-[3-methoxy-4-(1H-pyrazol-4-yl)benzoyl]-N-phenylpyrrolidine-2-carboxamide (110);
1-[(2R)-1-[3-methoxy-4-(1H-pyrazol-4-yl)benzoyl]pyrrolidine-2-carbonyl]-2,3-dihydro-1H-indole (111); and
N-ethyl-3-[(2R)-1-[3-methoxy-4-(1H-pyrazol-4-yl)benzoyl]pyrrolidin-2-yl]benzene-1-sulfonamide (112).

7. A pharmaceutical composition comprising one or more compounds according to claim 6 and a pharmaceutically acceptable carrier or diluent.

* * * * *